US008470528B2

(12) United States Patent
Pasqualini et al.

(10) Patent No.: US 8,470,528 B2
(45) Date of Patent: Jun. 25, 2013

(54) METHODS AND COMPOSITIONS RELATED TO ADENOASSOCIATED VIRUS-PHAGE PARTICLES

(75) Inventors: Renata Pasqualini, Houston, TX (US); Wadih Arap, Houston, TX (US); Juri Gelovani, Missouri City, TX (US); Frank C. Marini, III, Houston, TX (US); Amin Hajitou, Houston, TX (US); Mian Alauddin, Houston, TX (US); Martin Trepel, Freiburg (DE)

(73) Assignee: The Board of Regents of the University of Texas System, Austin, TX (US)

(*) Notice: Subject to any disclaimer, the term of this patent is extended or adjusted under 35 U.S.C. 154(b) by 134 days.

(21) Appl. No.: 12/771,390

(22) Filed: Apr. 30, 2010

(65) Prior Publication Data

US 2010/0254896 A1    Oct. 7, 2010

Related U.S. Application Data

(63) Continuation of application No. 11/733,148, filed on Apr. 9, 2007, now abandoned.

(60) Provisional application No. 60/744,492, filed on Apr. 7, 2006.

(51) Int. Cl.
*C12Q 1/70* (2006.01)
*G01N 33/53* (2006.01)
*A61K 51/00* (2006.01)
*A61K 49/00* (2006.01)
*A61B 5/055* (2006.01)

(52) U.S. Cl.
USPC .......... 435/5; 435/7.72; 435/7.8; 424/1.11; 424/1.17; 424/9.3; 424/9.341

(58) Field of Classification Search
USPC ........... 424/1.11, 1.17, 9.3, 9.341; 435/5, 435/7.72, 7.8
See application file for complete search history.

(56) References Cited

U.S. PATENT DOCUMENTS

| | | | |
|---|---|---|---|
| 4,797,368 A | 1/1989 | Carter et al. | 435/320.1 |
| 5,432,260 A | 7/1995 | Stahl | 530/322 |
| 5,643,756 A | 7/1997 | Kayman et al. | 435/69.7 |
| 5,693,509 A | 12/1997 | Cotten et al. | 435/456 |
| 5,871,727 A | 2/1999 | Curiel | 424/93.2 |
| 6,448,083 B1 | 9/2002 | Larocca et al. | 435/456 |
| 7,045,155 B2 | 5/2006 | Toyohara et al. | 424/1.85 |
| 2001/0046498 A1 | 11/2001 | Ruoslahti et al. | 424/178.1 |
| 2002/0068272 A1* | 6/2002 | Larocca et al. | |
| 2002/0122806 A1* | 9/2002 | Chinnaiyan et al. | |
| 2003/0033616 A1 | 2/2003 | Star-Lack et al. | 800/3 |
| 2003/0113320 A1 | 6/2003 | Ruoslahti et al. | 424/143.1 |
| 2003/0152578 A1 | 8/2003 | Ruoslahti et al. | 424/178.1 |
| 2004/0048243 A1 | 3/2004 | Arap et al. | 435/5 |
| 2004/0071689 A1 | 4/2004 | Ruoslahti et al. | 424/130.1 |
| 2004/0096441 A9 | 5/2004 | Ruoslahti et al. | 424/143.1 |
| 2004/0131623 A9 | 7/2004 | Ruoslahti et al. | 424/178.1 |
| 2004/0170955 A1 | 9/2004 | Arap et al. | 435/5 |
| 2005/0003466 A1 | 1/2005 | Arap et al. | 435/7.23 |
| 2005/0037417 A1 | 2/2005 | Ruoslahti et al. | 435/6 |
| 2005/0074747 A1 | 4/2005 | Arap et al. | 435/5 |
| 2005/0074812 A1 | 4/2005 | Ruoslahti et al. | 435/7.1 |
| 2005/0187161 A1 | 8/2005 | Kontoyiannis et al. | 514/14 |
| 2005/0191294 A1 | 9/2005 | Arap et al. | 424/143.1 |
| 2006/0094672 A1 | 5/2006 | Pasqualini et al. | 514/44 |
| 2006/0223141 A1* | 10/2006 | Carey et al. | |
| 2006/0239968 A1* | 10/2006 | Arap et al. | |

FOREIGN PATENT DOCUMENTS

| | | |
|---|---|---|
| WO | WO 96/10038 | 4/1996 |
| WO | WO 98/07408 | 2/1998 |
| WO | WO 2005/033321 | 4/2005 |
| WO | WO 2005/065418 | 7/2005 |

OTHER PUBLICATIONS

Arap et al., "Cell surface expression of the stress response chaperone GRP78 enables tumor targeting by circulating ligands," *Cancer Cell*, 6:275-284, 2004.
Blasberg and Tjuvajev, "Molecular-genetic imaging: current and future perspectives," *J. Clin. Invest.*, 111:1620-1629, 2003.
Castro et al., "Gene therapy for Parkinson's disease: recent achievements and remaining challenges," *Histl. Histopathol.*, 16:1225-38, 2001.
Chen et al., "Design and validation of a bifunctional ligand display system for receptor targeting," *Chem. Biol.*, 11:1081-1091, 2004.
Davis, "The many faces of epidermal growth factor repeats," *The New Biologist*, 2:410-9, 1990.
De and Gambhir, "Noninvasive imaging of protein-protein interactions from live cells and living subjects using bioluminescence resonance energy transfer," *FASEB J.*, 19:2017-2019, 2005.
Deonarain, "Ligand-targeted receptor-mediated vectors for gene therapy," *Expert. Opin. Ther. Pat.*, 8:53-69, 1998.
Eck and Wilson, In: Chapter 5: Gene-based therapy, Goodman & Gilman's The Pharmacological Basis of Therapeutics, 9th Ed., McGraw Hill, New York, pp. 77-101, 1996.
Górecki, "Prospects and problems of gene therapy: an update," *Expert. Opin. Emerging Drugs*, 6:187-98, 2001.
Gross and Piwnica-Worms, "Monitoring proteasome activity in cellulo and in living animals by bioluminescent imaging: technical considerations for design and use of genetically encoded reporters," *Methods Enzymol.*, 399:512-530, 2005.
Gross and Piwnica-Worms, "Spying on cancer: molecular imaging in vivo with genetically encoded reporters," *Cancer Cell*, 7:5-15, 2005.
Hajitou et al., "A Hybrid Vector for Ligand-Directed Tumor Targeting and Molecular Imaging," *Cell*, 125:385-398, 2006.
Hajitou et al., "Down-regulation of vascular endothelial growth factor by tissue inhibitor of metalloproteinase-2: effect on in vivo mammary tumor growth and angiogenesis," *Cancer Res.*, 61:3450-3457, 2001.
Hajitou et al., "Vascular targeting: recent advances and therapeutic perspectives," *Trends Cardiovasc. Med.*, 16:80-88, 2006.

(Continued)

*Primary Examiner* — Shin-Lin Chen
(74) *Attorney, Agent, or Firm* — Parker Highlander PLLC

(57) ABSTRACT

Embodiments of the invention are generally directed to compositions and methods of delivering one or more transgene to a target cell, such as a tumor cell, in a site-specific manner to achieve enhanced expression and to constructs and compositions useful in such applications. In certain aspects, expression from a therapeutic nucleic acid may be assessed prior to administration of a treatment or diagnostic procedure to or on a subject.

27 Claims, 34 Drawing Sheets

OTHER PUBLICATIONS

Hwu et al., "Functional and Molecular Characterization of Tumor-Infiltrating Lymphocytes Transduced with Tumor Necrosis Factor-alpha cDNA for the Gene Therapy of Cancer in Humans," *J Immunol.,* 151:4104-4115, 1993.

International Search Report and Written Opinion, issued in Int. App. No. PCT/US2007/66265, dated Aug. 14, 2008.

Ivanenkov et al., "Targeted delivery of multivalent phage display vectors into mammalian cells," *Biochim. Biophys. Acta,* 1448:463-472, 1999.

Kang et al., "Comparison of [14C]FMAU, [3H]FEAU, [14C]FIAU, and [3H]PCV for monitoring reporter gene expression of wild type and mutant herpes simplex virus type 1 thymidine kinase in cell culture," *Mol. Imaging Biol.,* 7:296-303, 2005.

Kaye et al., "A single amino acid substitute results in a retinoblastoma protein defective in a phosphorylation and oncoprotein binding," *Proc. Natl. Acad. Sci. USA,* 87:6922-6, 1990.

Kodama et al., "The features and shortcomings for gene delivery of current non-viral carriers," *Curr. Med.Chem.,* 13:2155-61, 2006.

Larocca et al., "Gene transfer to mammalian cells using genetically targeted filamentous bacteriophage," *FASEB J.,* 13:727-734, 1999.

Lebkowski et al., "Adeno-associated virus: a vector system for efficient introduction and integration of DNA into a variety of mammalian cell types," *Mol. Cell. Biol.,* 8:3988-3996, 1988.

Lowenstein and Castro, "Progress and challenges in viral vector-mediated gene transfer to the brain," *Curr. Opin. Mol. Ther.,* 4:359-71, 2002.

Luker et al., "Kinetics of regulated protein-protein interactions revealed with firefly luciferase complementation imaging in cells and living animals," *PNAS,* 101:12288-12293, 2004.

Marchio et al., "Aminopeptidase A is a functional target in angiogenic blood vessels," *Cancer Cell,* 5:151-162, 2004.

Massoud and Gambhir, "Molecular imaging in living subjects: seeing fundamental biological processes in a new light," *Genes Dev.,* 17:545-580, 2003.

McCarty et al., "Integration of adeno-associated virus (AAV) and recombinant AAV vectors," *Annu. Rev. Genet.,* 38:819-845, 2004.

Mizuguchi and Hayakawa, "Targeted adenovirus vectors," *Hum. Gene Ther.,* 15:1034-1044, 2004.

Muller et al., "Random peptide libraries displayed on adeno-associated virus to select for targeted gene therapy vectors," *Nature Biotechnol.,* 21:1040-1046, 2003.

Office Action, issued in U.S. Appl. No. 11/733,148, mailed Oct. 1, 2008.

Office Action, issued in U.S. Appl. No. 11/733,148, mailed Jan. 30, 2009.

Office Action, issued in U.S. Appl. No. 11/733,148, mailed Nov. 17, 2009.

Office Communication, issued in related International Application No. PCT/US07/66265, dated Jun. 11, 2008.

Piersanti et al., "Mammalian cell transduction and internalization properties of lambda phages displaying the full-length adenoviral penton base or its central domain," *J. Mol. Med.,* 82:467-476, 2004.

Poul and Marks, "Targeted gene delivery to mammalian cells by filamentous bacteriophage," *J. Mol. Biol.,* 288:203-211, 1999.

Shayakhmetov et al., "Adenovirus binding to blood factors results in liver cell infection and hepatotoxicity," *J. Virol.,* 79:7478-7491, 2005.

Skolnick and Fetrow, "From genes to protein structure and function: novel applications of computational approaches in the genomic era," *Trends in Biotech.,* 18:34-9, 2000.

Souza et al., "Networks of gold nanoparticles and bacteriophage as biological sensors and cell-targeting agents," *PNAS,* 103:1215-1220, 2006.

Tai and Laforest, "Instrumentation aspects of animal PET," *Annu. Rev. Biomed. Eng.,* 7:255-285, 2005.

Tjuvajev and Blasberg, "In vivo imaging of molecular-genetic targets for cancer therapy," *Cancer Cell,* 3:327-332, 2003.

Uhrbom et al., "Dissecting tumor maintenance requirements using bioluminescence imaging of cell proliferation in a mouse glioma model," *Nature Med.,* 10:1257-1260, 2004.

Verma and Somia, "Gene therapy—promises, problems and prospects," *Nature,* 389:239-42, 1997.

Walensky et al., "Activation of Apoptosis in Vivo by a Hydrocarbon-Stapled BH3 Helix," *Science,* 305:1411-1413, 2004.

White et al., "Targeted Gene Delivery to Vascular Tissue In Vivo by Tropism-Modified Adeno-Associated Virus Vectors," *Circulation,* 109:513-519, 2004.

"A hybrid phage-AAV vector for gene delivery and imaging," *Cancer Biology & Therapy,* 5(5):459-460, 2006.

Extended European Search Report issued in European Application No. 07760348.8, mailed Nov. 4, 2010.

Goncalves, "Adeno-associated virus: from defective virus to effective vector," *Virology J.,* 2(1): 43, 2005.

Koivunen et al., "Identification of receptor ligands with phage display peptide libraries," *J. Nuc. Med.,* 40(5): 883-888, 1999.

Office Communication issued in European Patent Application No. 07760348.8, dated Mar. 16, 2012.

Work et al., "Vascular bed-targeted in vivo gene delivery using tropism-modified adeno-associated viruses," *Molecular Therapy,* 13(4):683-693, 2006.

*New Medicine in Japan,* English language summary, 30:125-127, 2003.

Office Action issued in Japanese Application No. 2009-504507, mailed Jul. 25, 2012, and English language translation thereof.

\* cited by examiner

FIG. 3A
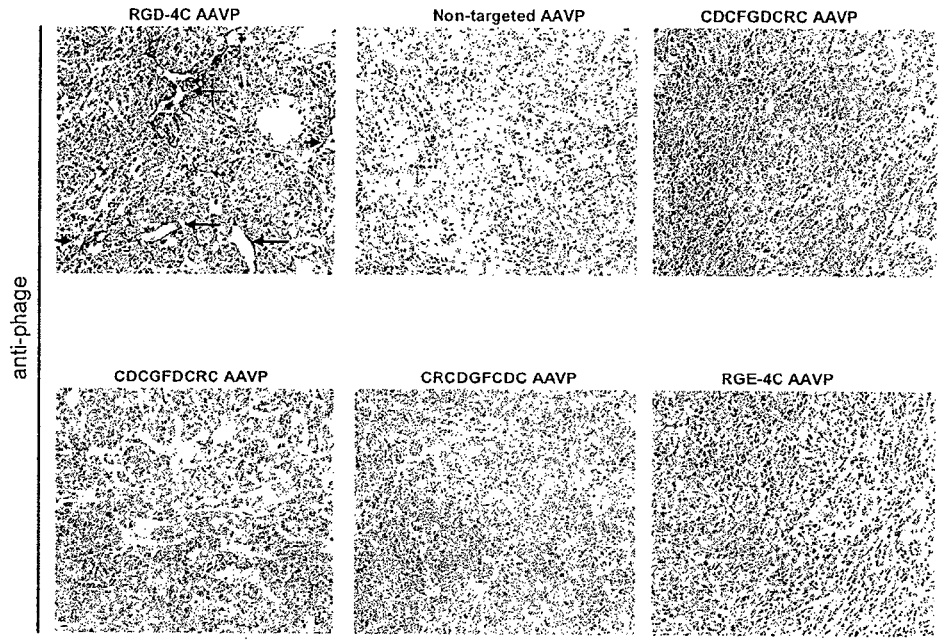
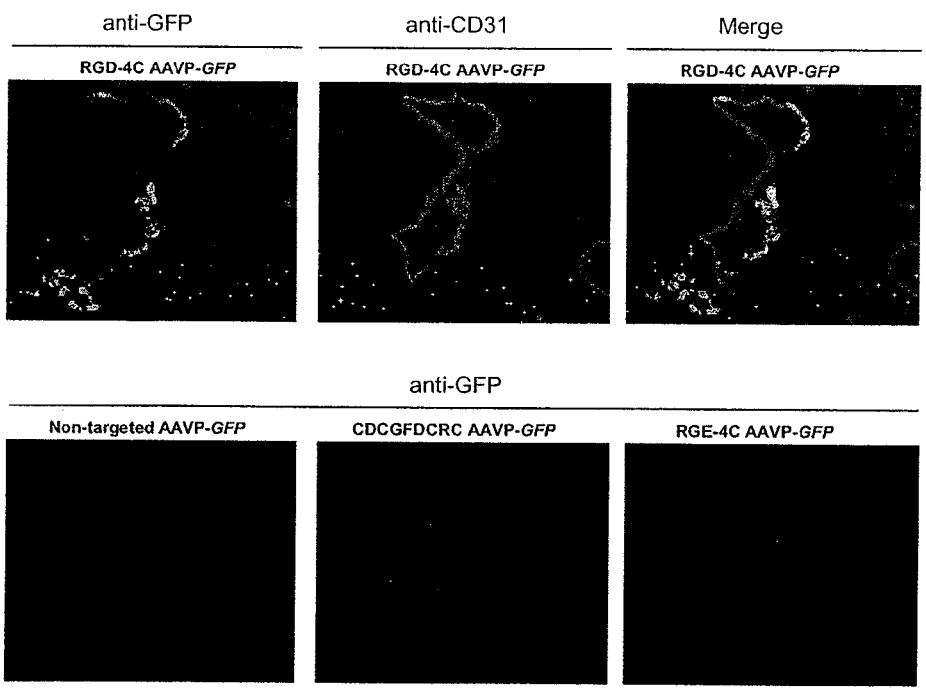
FIG. 3B

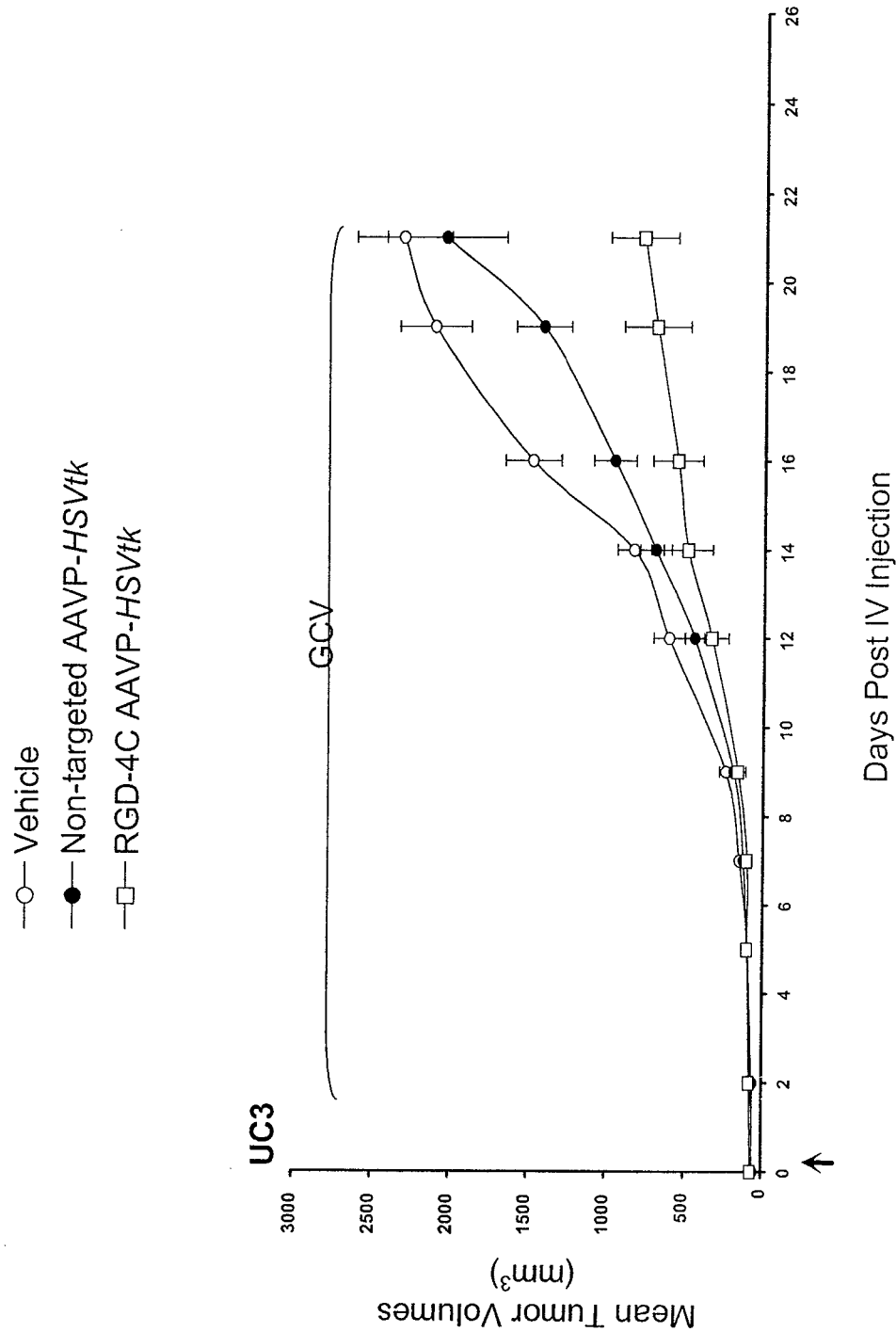

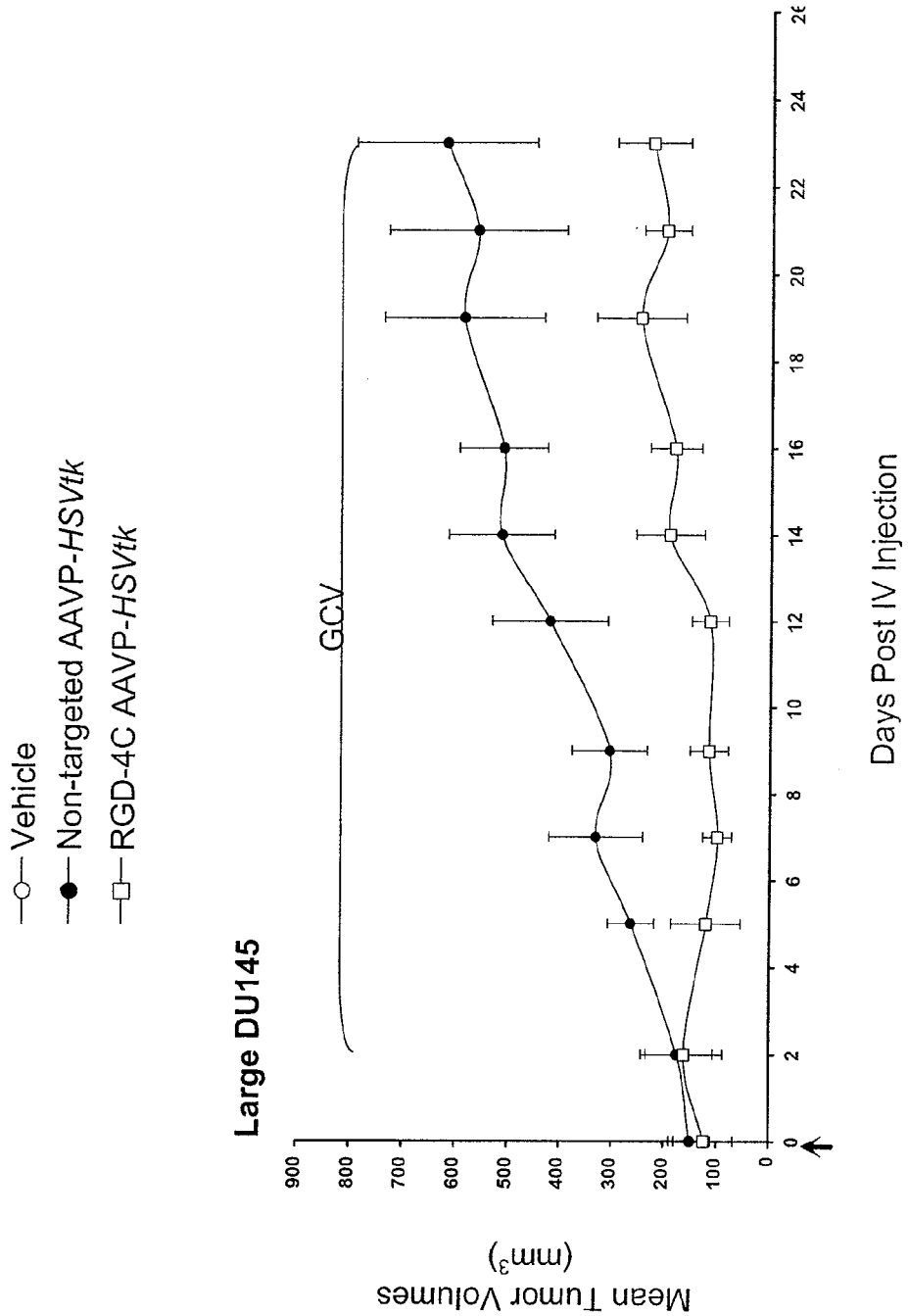

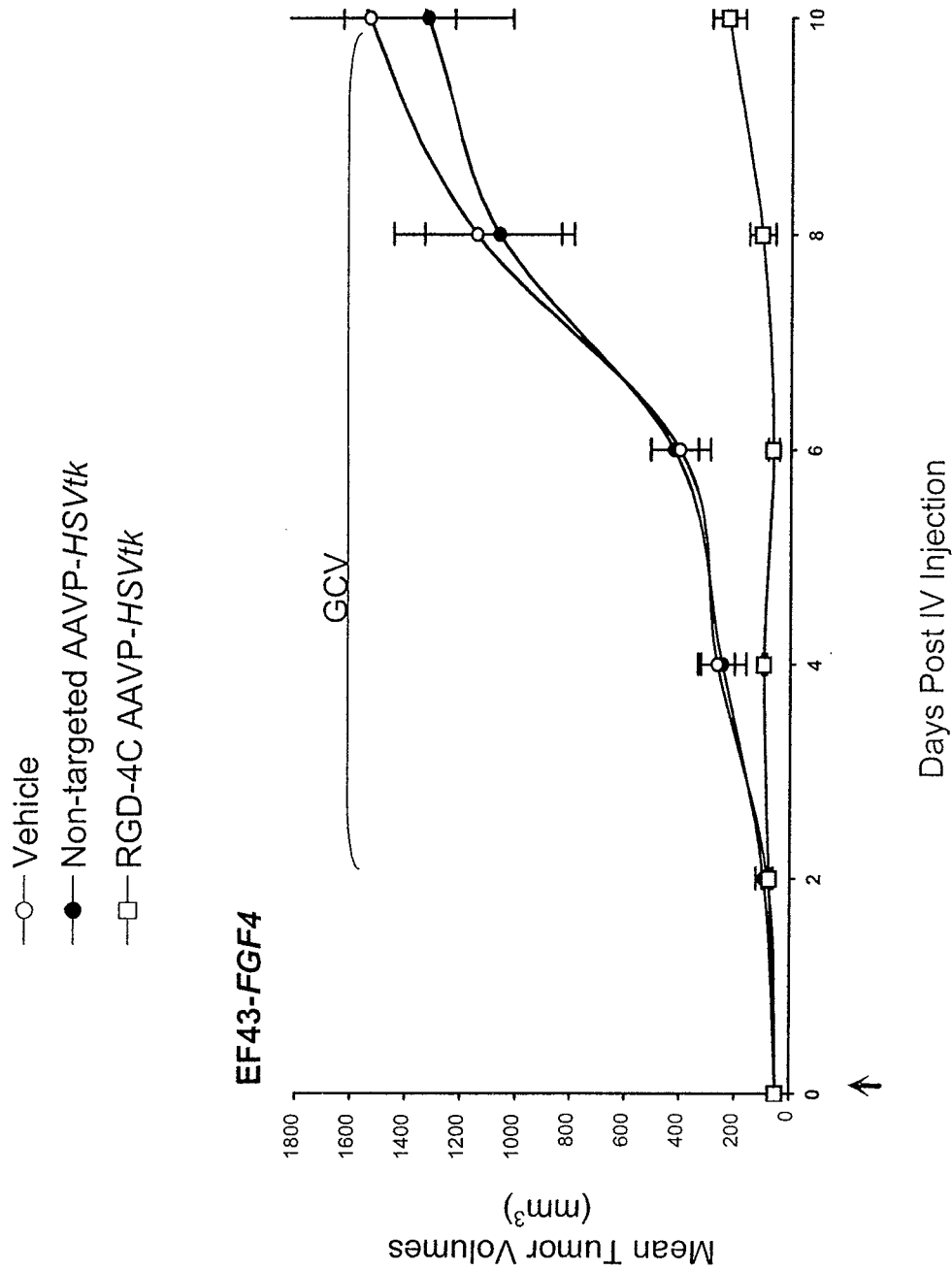

SEQUENCE LISTING

```
<160> NUMBER OF SEQ ID NOS: 9

<210> SEQ ID NO 1
<211> LENGTH: 9
<212> TYPE: PRT
<213> ORGANISM: Artificial
```

```
<220> FEATURE:
<223> OTHER INFORMATION: Synthetic peptide

<400> SEQUENCE: 1

Cys Arg Thr Ile Gly Pro Ser Val Cys
1               5

<210> SEQ ID NO 2
<211> LENGTH: 9
<212> TYPE: PRT
<213> ORGANISM: Artificial
<220> FEATURE:
<223> OTHER INFORMATION: Synthetic peptide

<400> SEQUENCE: 2

Cys Asp Cys Arg Gly Asp Cys Phe Cys
1               5

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

Cys Asp Cys Phe Gly Asp Cys Arg Cys
1               5

<210> SEQ ID NO 4
<211> LENGTH: 9
<212> TYPE: PRT
<213> ORGANISM: Artificial
<220> FEATURE:
<223> OTHER INFORMATION: Synthetic peptide

<400> SEQUENCE: 4

Cys Asp Cys Gly Phe Asp Cys Arg Cys
1               5

<210> SEQ ID NO 5
<211> LENGTH: 9
<212> TYPE: PRT
<213> ORGANISM: Artificial
<220> FEATURE:
<223> OTHER INFORMATION: Synthetic peptide

<400> SEQUENCE: 5

Cys Arg Cys Asp Gly Phe Cys Asp Cys
1               5

<210> SEQ ID NO 6
<211> LENGTH: 5
<212> TYPE: PRT
<213> ORGANISM: Artificial
<220> FEATURE:
<223> OTHER INFORMATION: Synthetic peptide

<400> SEQUENCE: 6

Arg Gly Asp Phe Val
1               5

<210> SEQ ID NO 7
<211> LENGTH: 132
<212> TYPE: DNA
<213> ORGANISM: Artificial
<220> FEATURE:
<223> OTHER INFORMATION: Synthetic primer
```

```
<400> SEQUENCE: 7
atttgcggcc gctttaccac catggagaca gacacactcc tgctatgggt actgctgctc    60
tgggttccag gttccactgg tgacgcggcc cagccggcca ggcgcgccgt aatgtctaag   120
ccaatagatg tt                                                       132

<210> SEQ ID NO 8
<211> LENGTH: 25
<212> TYPE: DNA
<213> ORGANISM: Artificial
<220> FEATURE:
<223> OTHER INFORMATION: Synthetic primer

<400> SEQUENCE: 8
atttgcggcc gctttaccac catgg                                          25

<210> SEQ ID NO 9
<211> LENGTH: 32
<212> TYPE: DNA
<213> ORGANISM: Artificial
<220> FEATURE:
<223> OTHER INFORMATION: Synthetic primer

<400> SEQUENCE: 9
cccaagcttg ggttatttga ttccactgtt gc                                  32
```

METHODS AND COMPOSITIONS RELATED TO ADENOASSOCIATED VIRUS-PHAGE PARTICLES

This present application is a continuation of application Ser. No. 11/733,148, filed Apr. 9, 2007, now abandoned which claims priority to U.S. Provisional Patent application Ser. No. 60/744,492 filed Apr. 7, 2006, the entire contents of each of which are incorporated herein by reference in its entirety.

The United States Government owns rights in this invention pursuant to a grant from the National Institutes of Health (NIH).

BACKGROUND OF THE INVENTION

I. Field of the Invention

Embodiments of this invention are directed generally to biology and medicine. In particular the invention is directed to field of gene therapy using AAVP in combination with imaging for providing therapy to a subject.

II. Background

A limitation of many biological-based therapies has been an inability to achieve controlled and effective delivery of biologically active molecules to tumor cells or their surrounding matrix. The aim of employing gene-based therapy is to achieve effective delivery of biological products, as a result of gene expression, to their site of action within the cell. Gene-based therapy can also provide control over the level, timing, and duration of action of these biologically active products by including specific promoter/activator elements in the genetic material transferred resulting in more effective therapeutic intervention. Methods are being developed for controlled gene delivery to various somatic tissues and tumors using novel formulations of DNA, and for controlling gene expression using cell specific, replication activated, and drug-controlled expression systems.

In one approach, gene therapy attempts to target cells in a specific manner. Thus, a therapeutic gene is linked in some fashion to a targeting molecule in order to deliver the gene into a target cell or tissue. Current methods typically involve linking up a targeting molecule such as a ligand or antibody that recognizes an internalizing receptor to either naked DNA or a mammalian cell virus containing the desired gene. When naked DNA is used it must be condensed in vitro into a compact geometry for entry into cells. A polycation such as polylysine is commonly used to neutralize the charge on DNA and condense it into toroid structures. This condensation process, however, is poorly understood and difficult to control, thus, making the manufacturing of homogeneous gene therapy drugs extremely challenging.

Bacteriophage (phage), such as lambda and filamentous phage, have occasionally been used in efforts to transfer DNA into mammalian cells. In general, transduction of lambda was found to be a relatively rare event and the expression of the reporter gene was weak. In an effort to enhance transduction efficiency, methods utilizing calcium phosphate or liposomes (which do not specifically target a cell surface receptor) were used in conjunction with lambda. Gene transfer has been observed via lambda phage using calcium phosphate coprecipitation, or via filamentous phage using DEAE-dextran or lipopolyamine. However, these methods of introducing DNA into mammalian cells are not practical for gene therapy applications, as the transfection efficiency tends to be low, non-specific, and transfection is not only cumbersome, but is promiscuous regarding cell type.

Currently, eukaryotic viruses unquestionably provide superior transgene delivery and transduction (Kootstra and Verma, 2003; Machida, 2003) but ligand-directed targeting of such vectors generally requires ablation of their native tropism for mammalian cell membrane receptors (Miller et al., 2003; Mizuguchi and Hayakawa, 2004; White et al., 2004). In contrast, prokaryotic viruses such as bacteriophage (phage) are generally considered poor vehicles for mammalian cell transduction. However, despite their inherent shortcomings as "eukaryotic" viruses, phage particles have no tropism for mammalian cells (Zacher et al., 1980; Barrow and Soothill, 1997; Barbas et al., 2001) and have even been adapted to transduce such cells (Ivanenkov et al., 1999; Larocca et al., 1999; Poul and Marks, 1999; Piersanti et al., 2004) albeit at low efficiency.

More reliable means of targeting vectors to specific cells (or receptors) and of guaranteeing a therapeutically useful degree of gene delivery and expression are thus required, if vectors useful in therapeutic applications are to be achieved.

SUMMARY OF THE INVENTION

Embodiments of the invention are generally directed to compositions and methods of delivering one or more transgene to a target cell, such as a tumor cell, in a site-specific manner to achieve enhanced expression and to constructs and compositions useful in such applications. In certain aspects, expression from a therapeutic nucleic acid may be assessed prior to administration of a treatment or diagnostic procedure to or on a subject. In a further aspect, the determination or evaluation of expression in the region or location needed for therapeutic benefit is assessed and any unnecessary or marginal beneficial treatment can be with held in lieu of alternative treatments.

Without being bound by any particular theory or mechanism, the present disclosure is based on the observation that transgene expression may be increased when the transgene is integrated into a genome with a multiplicity greater than one. Of particular interest is the ability of certain chimeric AAVP particles to transduce cells with more than one copy of the transgene, often as a concatamer. Transduced cells also may be monitored by the expression of a reporter gene carried by the chimeric AAVP particles. Any transgene may be included in and expressed from an AAVP particle of this disclosure.

Certain embodiments of the invention include methods and compositions for detecting gene transfer to and/or gene expression in a target tissue of a subject comprising one or more of the following steps:

(a) One step that may be used in the present methods includes delivering to the target tissue of a subject an AAVP vector containing a reporter gene, which may or may not be naturally present in the host subject. Typically, the reporter gene will not be expressed in location or region to be imaged and/or treated. In certain aspects, the reporter gene is a wild-type, a mutant, or a genetically engineered kinase. In a further aspect the kinase is a thymidine kinase. In still a further aspect, the kinase is a herpes simplex virus-thymidine kinase gene or human thymidine kinase type 2. Typically, the transfer vector or AAVP is introduced to cells of the target tissue, and the reporter gene is expressed in the cells of the target tissue, thereby generating a reporter gene product (protein) which accumulates only in the cells effectively transfected by the AAVP vector.

(b) Another step that may be used is administering to the host subject a labeled reporter substrate where cells expressing a reporter gene product metabolize the labeled reporter substrate to produce a labeled reporter metabolite wherein the labeled reporter substrate comprises a radiolabeled nucleoside analogue.

(c) Yet another step that may be used in the present methods includes non-invasively imaging a target tissue or cells containing a labeled metabolite of the reporter substrate. In certain aspects, the subject is subjected to imaging after clearance of residual reporter substrate not metabolized by the reporter gene product from the host subject thereby detecting gene transfer to and expression in the target tissue. In a further aspect the subject or subjects tissues are subjected to imaging after 1, 2, 3, 4, 5, 6, 7, 8, 9, 10, or more minutes, hours, days, or weeks, depending on the metabolism of clearance of non-metabolized reporter substrate.

The methods can further comprise waiting for a period of time after step (b) sufficient to allow about, at least, or at most 60, 65, 67, 70, 75, 77, 80, 85, 87, 90, 95, 97% or more, including all values and ranges there between of non-metabolized (reporter substrate not metabolized by the expression product) by the reporter gene product to clear from the subject. The non-metabolized substrate may include non-specific label derived from residual reporter substrate not metabolized. AAVP vector can be introduced to the cells of the target tissue by in vitro or in vivo transfection (or transduction). In certain aspects, AAVP is administered intravenously, intratumorally, intrarterially, intrapleurally, intrabronchially, and/or orally.

In certain aspects, a reporter substrate is labeled with a radioisotope suitable for imaging by positron emission tomography, gamma camera, or single-photon emission computed tomography. The reporter substrate and/or metabolite of the reporter substrate are compounds containing a stable-isotope nuclide including but not limited to $^2H$, $^{13}C$, $^{15}N$ and $^{19}F$. In a further aspect, the labeled reporter metabolite is imaged by positron emission tomography. In still further aspects, the labeled reporter metabolite is imaged by gamma camera or single-photon emission computed tomography. In yet still further aspects, the labeled reporter substrate metabolite is imaged by magnetic resonance imaging.

An AAVP vector may incorporate a reporter gene and suitable transcription promoter and enhancer elements, ensuring tissue-specific, tissue-selective, or transcription factor-specific, or signal transduction-specific transcriptional activation of reporter and therapeutic gene co-expression. In certain aspects, the organ, tissue, cells or a cell is transfected with a reporter gene operably coupled to transcription regulatory elements such as promoter and/or enhancer elements ex vivo (in vitro) prior to administration of the cells or a cell to a subject. A labeled 2'-fluoro-nucleoside analogue includes, but is not limited to 5-[$^{123}$I]-2'-fluoro-5-iodo-1β-D-arabinofuranosyl-uracil; 5-[$^{124}$I]-2'-fluoro-5-iodo-1β-D-arabinofuranosyl-uracil, 5-[$^{131}$I]-2'-fluoro-5-fluoro-1β-D-arabinofuranosyl-uracil; 2-[$^{131}$I]-2'-fluoro-5-methyl-1-β-D-arabinofuranosyl-uracil; 5-([$^{11}$C]-methyl)-2'-fluoro-5-methyl-1-β-D-arabinofuranosyl-uracil; 2-[$^{11}$C]-2'-fluoro-5-ethyl-1-β-D-arabinofuranosyl-uracil; 5-([$^{11}$C]-ethyl)-2'-fluoro-5-ethyl-1-β-D-arabinofuranosyl-uracil; 5-(2-[$^{18}$F]-ethyl)-2'-fluoro-5-(2-fluoro-ethyl)-1-β-D-arabinofuranosyl-uracil, 5-[$^{123}$I]-2'-fluoro-5-iodovinyl-1-β-D-arabinofuranosyl-uracil; 5-[$^{124}$I]-2'-fluoro-5-iodovinyl-1-β-D-arabinofuranosyl-uracil; 5-[$^{131}$I]-2'-fluoro-5-iodovinyl-1-β-D-arabinofuranosyl-uracil; 5-[$^{123}$I]-2'-fluoro-5-iodo-1-β-D-ribofuranosyl-uracil; 5-[$^{124}$I]-2'-fluoro-5-iodo-1-β-D-ribofuranosyl-uracil; 5-[$^{131}$I]-2'-fluoro-5-iodo-1-β-D-ribofuranosyl-uracil; 5-[$^{123}$I]-2'-fluoro-5-iodovinyl-1-β-D-ribofuranosyl-uracil; 5-[$^{124}$I]-2'-fluoro-5-iodovinyl-1-β-D-ribofuranosyl-uracil; 5-[$^{131}$I]-2'-fluoro-5-iodovinyl-1-β-D-ribofuranosyl-uracil; or 9-4-[$^{18}$F]fluoro-3-(hydroxymethyl)butyl]guanine.

The imaging data can embody, but is not limited to imaging obtained with magnetic resonance imaging (MRI), nuclear medicine, positron emission tomography (PET), computerized tomography (CT), ultrasonography (US), optical imaging, infrared imaging, in vivo microscopy and x-ray radiography. Imaging can be coupled with medical devices, drugs or compounds, contrast agents or other agents or stimuli that may be used to elicit additional information from the imaging. Images are obtained using these modalities of the lesion, tissue, specimen, system, organism, subject or patient and can be static or dynamic images both in time and/or space.

The imaging can be matched to the tissue, specimen, system, organism, or patient from which the large scale biological data is obtained. Imaging information is extracted from each image, imaging study or studies or examinations, and can consists of quantitative or qualitative imaging features that may embody but are not limited to differences in morphology, composition, structure, physiology, gene expression, or function of a lesion, a tissue, specimen, system, organism, or patient. Examples of imaging information include but are not limited to imaging features that may be extracted from multi-phase contrast enhanced dynamic CT, functional imaging, magnetic resonance spectroscopy, diffusion tensor imaging, diffusion or perfusion based imaging as well as targeted imaging encapsulated by nuclear medicine or PET. For an example see U.S. Patent Publication 20030033616 and 20060223141, which are incorporated herein by reference in its entirety.

In certain embodiments, the invention includes methods of treating a subject comprising one or more of the following steps:

(a) administering a therapeutic AAVP encoding a reporter to a subject having, suspected of having or at risk of developing a pathologic or disease condition; and (b) evaluating in situ expression of the therapeutic AAVP in a tissue or cell targeted for treatment by detecting the encoded reporter or reporter activity.

In certain aspects, the methods can further comprise administering a cancer treatment to the subject based on expression of a therapeutically sufficient level of a therapeutic gene expressed by the AAVP nucleic acid in the target organ, tissue or cell. In a further aspect, second therapeutic AAVP can be administered if the expression of the first therapeutic AAVP is not expressed at a therapeutically effective level. The second therapeutic AAVP may comprise a second targeting ligand or a combination or ligands. Also, the second AAVP can comprise a second control element for expression in target organ, tissue, cells, or cell. Evaluation of AAVP expression can be by non-invasive detection of the reporter or an activity of the reporter (e.g., detection of labeled substrate metabolized by a reporter protein). In certain aspects, the reporter is a therapeutic protein. In a further aspect, the therapeutic protein is a prodrug converting enzyme. In still a further aspects, the reporter is an enzyme, and particularly a kinase. In certain embodiments the kinase is thymidine kinase, e.g., a HSV-tk or a human tk2. Typically, the kinase modifies or metabolizes a detectably labeled compound or labeled substrate. In certain aspects the substrate or compound comprises a detectable label that is detectable by fluorescence, chemiluminescence, surface enhanced raman spectroscopy (SERS), magnetic resonance imaging (MRI), computer tomography (CT), or positron emission tomography (PET) imaging. In certain aspects, the detectably labeled compound is a nucleoside analog. The detectably label compound may include, but is not limited to fluorodeoxyglucose (FDG); 2'-fluoro-2'deoxy-1beta-D-arabinofuranosyl-5-ethyl-uracil (FEAU); 5-[$^{123}$I]-2'-fluoro-5-iodo-1β-D-arabinofuranosyl-uracil; 5-[$^{124}$I]-2'-fluoro-5-iodo-1β-D-arabinofuranosyl-uracil; 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil; 2-[$^{11}$I]- and 5-([$^{11}$C]-methyl)-2'-fluoro-5-methyl-1-β-D-arabinofuranosyl-uracil; 2-[$^{11}$C]-2'-fluoro-5-ethyl-1-β-D-arabinofuranosyl-uracil; 5-([$^{11}$C]-ethyl)-2'-fluoro-5-ethyl-1-β-D-arabinofuranosyl-uracil; 5-(2-[$^{18}$F]-ethyl)-2'-fluoro-5-(2-fluoro-ethyl)-1-β-D-arabinofuranosyl-uracil, 5-[$^{123}$I]-2'-fluoro-5-iodovinyl-1-β-D-arabinofuranosyl-uracil; 5-[$^{124}$I]-2'-fluoro-5-iodovinyl-1-β-D-arabinofuranosyl-uracil; 5-[$^{131}$I]-2'-fluoro-5-iodovinyl-1-β-D-arabinofuranosyl-uracil; 5-[$^{123}$I]-2'-fluoro-5-iodo-1-β-D-ribofuranosyl-uracil; 5-[$^{124}$I]-2'-fluoro-5-iodo-1-β-D-ribofuranosyl-uracil; 5-[$^{131}$I]-2'-fluoro-5-iodo-1-β-D-ribofuranosyl-uracil; 5-[$^{123}$I]-2'-fluoro-5-iodovinyl-1-β-D-ribofuranosyl-uracil; 5-[$^{124}$I]-2'-fluoro-5-iodovinyl-1-β-D-ribofuranosyl-uracil; 5-[$^{131}$I]-2'-fluoro-5-iodovinyl-1-β-D-ribofuranosyl-uracil; or 9-4-[$^{18}$F]fluoro-3-(hydroxymethyl)butyl]guanine.

In a further aspect the labeled substrate or compound can be labeled with $^{18}$F, $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{109}$Cd, $^{47}$Ca, $^{11}$C, $^{13}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{153}$Gd, $^{66}$Ga, $^{67}$Ga, $^{68}$Ga, $^{72}$Ga, $^{198}$Au, $^{2}$H, $^{3}$H, $^{166}$Ho, $^{111}$In, $^{113}$In, $^{115}$In, $^{123}$I, $^{125}$I, $^{131}$I, $^{189}$Ir, $^{191}$Ir, $^{192}$Ir, $^{194}$Ir, $^{19}$F, $^{52}$Fe, $^{55}$Fe, $^{59}$Fe, $^{177}$Lu, $^{15}$O, $^{191}$Os, $^{109}$Pd, $^{32}$P, $^{33}$P, $^{42}$K, $^{226}$Ra, $^{186}$Re, $^{188}$Re, $^{82}$Rb, $^{153}$Sm, $^{46}$Sc, $^{47}$Sc, $^{72}$Se, $^{75}$Se, $^{105}$Ag, $^{15}$N, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{116}$Yb, $^{169}$Yb, $^{175}$Yb, $^{88}$Y, $^{90}$Y, $^{62}$Zn, or $^{65}$Zn. In particular aspects the detectable label is $^{131}$I, $^{125}$I, $^{123}$I, $^{111}$I, $^{99m}$Tc, $^{90}$Y, $^{186}$Re, $^{188}$Re, $^{32}$P, $^{153}$Sm, $^{67}$Ga, $^{201}$Tl, $^{77}$Br, or $^{18}$F label.

An AAVP of the invention may comprise a moiety that selectively targets a tissue or cell targeted for treatment. In certain aspects, the moiety is encoded by or coupled to a capsid protein and/or a recombinant capsid protein of an AAVP. In certain aspects, a capsid protein comprises a targeting peptide. A targeting peptide can be a cyclic peptide, a bicyclic, and/or a linear peptide. The targeting peptide selectively binds a cell expressing an integrin on the cell surface. An integrin can be a αvβ3 or αvβ5 integrin. In a further aspect, peptide comprises an RGD motif. In still a further aspect, the peptide can selectively binds a cell expressing a transferrin receptor, such a peptide can include an amino acid sequence comprising CRTIGPSVC.

In certain aspects, a subject can have, is suspected of having, or at risk of developing a hyperproliferative disease. Hyperproliferative disease include, but are not limited to fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder cancer, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma. In a particular aspect the hyperproliferative disease is glioma.

In a further embodiment, a reporter and/or therapeutic gene is operatively coupled to a tissue or cell selective promoter, or a tissue or cell specific promoter. In certain aspects, evaluating expression comprises administering a labeled compound or substrate that is metabolized by a cell expressing the AAVP nucleic acid and typically not metabolized to a significant extend by non-target tissues.

A therapeutic AAVP may also encode a second therapeutic gene. The second therapeutic gene can be, but is not limited to a tumor suppressor, an inhibitory RNA, an inhibitory DNA, or a prodrug converting enzyme.

In still further embodiments, compositions of the invention can include a therapeutic AAVP nucleic acid comprising a nucleic acid segment comprising an inhibitory RNA or inhibitory DNA. The inhibitory RNA can be a siRNA, a miRNA, or an antisense RNA or DNA. In certain aspects an AAVP nucleic acid is comprised in a phage particle. In a further aspect the particle comprises a targeting ligand as described herein.

Certain embodiments include compositions and methods for modulating the expression of a gene comprising administering an AAVP nucleic acid or particle comprising such.

In accordance with the present invention, a selected gene or polypeptide may refer to any protein, polypeptide, or peptide. A therapeutic gene or polypeptide is a gene or polypeptide which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, Bax, Bak, Bik, Bim, Bid, Bad, Harakiri, Fas-L, mda-7, fus, interferon α, interferon β, interferon γ, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidase, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, -glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, -L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. Some specific example embodiments of the disclosure may be understood by referring, in part, to the following description and the accompanying drawings.

FIG. 1B is an image showing RGD-4C AAVP carrying reporter genes indicating ligand-directed internalization. FIG. 1C shows targeted gene transfer mediated by RGD-4C AAVP-β-galactosidase to KS 1767 cells. FIG. 1D shows inhibition of transduction by the synthetic RGD-4C peptide, but not by an unrelated control peptide; nonspecific transduction levels were determined by using non-targeted AAVP. An anti-β-gal antibody was used for staining and gene expression was detected by immunofluorescence. FIG. 1E shows the rescue of recombinant AAV from cells infected with RGD-4C AAVP. Human 293 cells were incubated with targeted RGD-4C AAVP-GFP ($10^6$ transducing units/cell) or negative controls (targeted non-chimera RGD-4C phage-GFP, nontargeted AAVP-GFP). Four days after infection, cells were transfected with an AAV rep- and cap-expressing plasmid and superinfected with wild-type adenovirus type 5 (Ad). Cells were harvested 72 h post-adenoviral infection and supernatants were then used to infect new 293 cells. GFP expression was analyzed by flow cytometry 48 h later. Mean increases in recombinant AAV-GFP produced over background after rescue from each construct are shown.

FIG. 2B shows Southern blot analysis of the persistence of transgene cassette in clonal cell lines transduced with RGD-4C AAVP-GFPneo or RGD-4C phage-GFPneo. Total cellular DNA from non-transduced 293 parental cells or each of the transduced cell clones (#1-9 for each group) was double-digested with AflII-XhoI (one restriction digestion site per each enzyme within the construct DNA flanking the transgene cassette). FIG. 2C shows analysis of potential head-to-tail concatemers of the transgene cassette by Southern blot. Total cellular DNA was digested with Xho-I (single restriction digestion site within the transgene cassette next to the 3' ITR) prior to Southern blotting.

FIGS. 3A-3B FIG. 3A shows immunohistochemical staining against phage in KS 1767-derived xenografts after systemic administration (intravenously through the tail vein) of RGD-4C AAVP ($5\times10^{10}$ TU) or negative controls (non-targeted AAVP, scrambled RGD-4C AAVP, or RGE-4C AAVP) into deeply anesthetized nude mice bearing KS1767-derived tumor xenografts. AAVP constructs were allowed to circulate for 5 min, followed by perfusion and surgical removal of tumors. A polyclonal antibody against phage was used for staining on paraffin-embedded tumor sections. Arrows point to phage staining in tumor blood vessels. FIG. 3B shows immunofluorescence analysis of GFP expression in KS1767-derived xenografts at day 7 after systemic administration of either RGD 4C AAVP-GFP or negative controls (non-targeted, scrambled or mutant) as indicated.

FIG. 4B shows multi-tracer PET imaging in tumor-bearing mice after systemic delivery of targeted RGD-4C AAVP-HSVtk. Nude mice bearing DU145-derived tumor xenografts (n=9 tumor-bearing mice per each cohort) received a systemic single-dose ($5\times10^{11}$ TU, intravenous) RGD-4C AAVP-HSVtk or non-targeted AAVP-HSVtk. PET images with [$^{18}$F]-FDG and [$^{18}$F]-FEAU obtained before and after GCV treatment are presented. T, tumor; H, heart; BR, brain; BL, bladder. Calibration scales are provided in panels. Overimposition of PET images and photographic images of representative tumor-bearing mice was performed to simplify the interpretation of [$^{18}$F]-FDG and [$^{18}$F]-FEAU biodistribution. FIG. 4C shows growth curves of individual tumor-xenografts after AAVP administration. FIG. 4D shows temporal dynamics of HSVtk gene expression as assessed by repetitive PET imaging with [$^{18}$F]-FEAU at different days post AAVP administration. FIG. 4E shows changes in tumor viability before and after GCV therapy as assessed with [$^{18}$F]-FDG PET.

FIGS. 5A-5G FIG. 5A is a graph showing the plotted mean tumor volumes±standard deviations (SD) over time. Cohorts of immunodeficient nude mice with established human xenografts (size-matched at approximately 50 mm$^2$) derived from KS 1767 cells were used. The mice received a single systemic administration ($5\times10^{10}$ TU, intravenous) of either RGD-4C AAVP-HSVtk or controls (non-targeted AAVP-HSVtk, RGD-4C AAVP-GFP, or vehicle alone). Gancyclovir (GCV) was administered to mice from post-treatment day 2 until the end of the experiments. All mice received GCV except for an additional control group treated with RGD-4C AAVP-HSVtk but without GCV afterwards. FIG. 5B is a graph showing the plotted mean tumor volumes±standard deviations (SD) over time. Cohorts of immunodeficient nude mice with established human xenografts (size-matched at approximately 50 mm$^2$) derived from bladder UC3 carcinoma cells. The mice received a single systemic administration ($5\times10^{10}$ TU, intravenous) of either RGD-4C AAVP-HSVtk or controls (non-targeted AAVP-HSVtk, RGD-4C AAVP-GFP, or vehicle alone). Gancyclovir (GCV) was administered to mice from post-treatment day 2 until the end of the experiments. All mice received GCV except for an additional control group treated with RGD-4C AAVP-HSVtk but without GCV afterwards. FIG. 5C is a graph showing the plotted mean tumor volumes±standard deviations (SD) over time. Cohorts of immunodeficient nude mice with established human xenografts (size-matched at approximately 50 mm$^2$) derived from prostate DU145 carcinoma cells. The mice received a single systemic administration ($5\times10^{10}$ TU, intravenous) of either RGD-4C AAVP-HSVtk or controls (non-targeted AAVP-HSVtk, RGD-4C AAVP-GFP, or vehicle alone). Gancyclovir (GCV) was administered to mice from post-treatment day 2 until the end of the experiments. All mice received GCV except for an additional control group treated with RGD-4C AAVP-HSVtk but without GCV afterwards. Shown are the plotted mean tumor volumes±standard deviations (SD) over time. FIG. 5D is a graph showing growth inhibition of large DU145-derived xenografts (at approximately 150 mm$^2$) by a single systemic dose ($5\times10^{10}$ TU, intravenous) of RGD-4C AAVP-HSVtk. FIG. 5E is a graph showing inhibition of tumor growth of EF43-FGF4 mouse mammary carcinoma (size-matched at approximately 50 mm$^2$) in immunocompetent BALB/c mice by a single intravenous dose ($5\times10^{10}$ TU) of RGD-4C AAVP-HSVtk. FIG. 5F is a graph showing long-term efficiency of RGD-4C AAVP-HSVtk and GCV by repeated doses of AAVP ($5\times10^{10}$ TU each, intravenous) to immunocompetent BALB/c mice bearing isogenic EF43-FGF4 tumors. Therapy results were consistently observed in independent experiments with tumor-bearing mice cohorts (n=10 mice per treatment group). Arrows indicate times of AAVP administration. FIG. 5G is a graph showing the effect of the humoral immune response against phage on therapy with RGD-4C AAVP-HSVtk. BALB/c immunocompetent mice (n=7 mice per group) were first "vaccinated" by receiving three systemic doses of RGD-4C AAVP-GFP ($10^{10}$ TU per week for three weeks, intravenous). Mice were then implanted with EF43-FGF4 cells. When tumors were established (size-matched at approximately 50 mm$^2$), tumor-bearing mice received one systemic single-dose of RGD-4C AAVP-HSVtk or non-targeted AAVP-HSVtk followed by GCV maintenance (started at day 2 post administration of the AAVP). Serum samples were collected from mice pre- and post-vaccination was started and again at the end of vaccination scheme before AAVP administration in order to confirm the presence of high titers (up to approximately 1:10,000) of circulating anti-phage IgG by ELISA. Vaccination did not appear to affect the anti-tumor effects, despite the anti-phage antibodies presence.

FIG. 6B is histopathologic analysis of EF43-FGF4 treated tumors. EF43-FGF4 tumors were recovered, sectioned, and stained. Non-targeted AAVP-HSVtk-treated tumors (left panels), the border between the outer rims and central tumor areas (middle panels), and central tumor areas of RGD-4C AAVP-HSVtk-treated tumors (right panel) are shown as high-magnification views from the low-magnification inserts of serial tumor sections. Hematoxylin and eosin (H&E) staining, anti-CD31 immunostaining and TUNEL staining of tumor sections are shown. Arrows point to tumor blood vessels and apoptotic cells.

FIG. 8B shows a PCR analysis of concatemers of the transgene cassette in 293 clonal cell lines stably transduced with RGD-4C phage-GFPneo or RGD-4C AAVPGFPneo. Non-transduced 293 parental cells served as a negative control; additional negative controls and a 100-bp molecular marker (Invitrogen) are also shown as indicated. Nested PCR with primers annealing close to the 5' and 3' end of the transgene cassette was performed to identify concatemeric forms in the DNAs corresponding to the RGD-4C AAVP and RGD-4C phage. Arrows indicate primers (H, head; T, tail). PCR-amplification products were detected in 2% agarose gels and revealed concatemeric vector DNA exclusively in the cell clones transduced with AAVP. Sequencing results of different concatemeric forms in AAVP DNA (capital letters denote 3' end of transgene cassette, italic letters denote 5' end of transgene cassette), revealed Head-to-Tail concatemers with deleted ITRs.

FIG. 10B is an image of immunofluorescence analysis of GFP expression in EF43-FGF4 tumors at 1 week after intravenous administration of non-targeted AAVP-GFP (left panel) or RGD-4C AAVP-GFP (middle panel) into mice bearing EF43-FGF4 tumors. Immunostaining against αv-integrin in EF43-FGF4 tumors is also shown (right panel).

(FIG. 12A) Human melanoma cells, M21 were infected with AAVP; non-targeted TNF-α expressing phage fdTNF-α (upper panel) and targeted TNF-α expressing virus RGDTNF-α (lower panel) and detected using fd specific primary antibody followed by FITC labeled secondary antibody. (FIG. 12B) M21 cells infected with PBS, empty non-targeted virus (fd), empty targeted virus (RGD), non-targeted TNF-α expressing virus (fdTNF-α) and targeted TNF-α expressing virus RGDTNF-α. 5 days after infection culture supernatant was analyzed to measure TNF-α by ELISA. The culture supernatant 12 days after the infection is also shown. (FIG. 12C) Human umbilical vein endothelial cells (HUVEC) were treated with day 5 supernatant from M21 cells infected various groups; PBS, fd (non-targeted null virus), RGD (targeted null virus), fdTNF (non-targeted TNF-α expressing virus) and RGDTNF (targeted TNF-α expressing virus) and analyzed for tissue factor (TF) production. Recombinant TNF-α was used as a positive control. To check the specificity, M21 supernatant from RGDTNF infected cells incubated with TNF-α specific antibody, before applying onto HUVEC. Day 23 supernatant after infection also been tested for TF secretion FIGS. 13A-13H AAVP is specifically targeted to tumor vasculature. Human melanoma xenografts injected with either PBS or RGDTNF-α stained with bacteriophage specific antibody and CD31 blood vessel antibody. The detection was done using Alexa Flour 488, Alexa Flour 594 and DAPI to visualize blood vessels, AAVP and cell nuclei respectively (250×). None of the animals injected with PBS showed presence of AAVP at any time point. A representative tumor section from animal injected with PBS for 15 min is shown (FIG. 13A). The animals injected with AAVP expressing RGDTNF-α, showed colocalization of virus particles in the blood vessels as early as 15 min (FIG. 13B) and in subsequent time points: day 1 (FIG. 13C), day 2 (FIG. 13D), day 3 (FIG. 13E), day 4 (FIG. 13F), day 8 (FIG. 13G), and day 10 (FIG. 13H).

(FIG. 17A) Frozen sections from animals with human melanoma xenografts injected with RGDTNF-α AAVP stained with TNF-α specific antibody using immunohistochemical analysis. TNF-α staining is seen as a brown color stain around the blood vessels (left panel, 100×; right panel 400×). (FIG. 17B) Frozen sections from animals with human melanoma xenografts injected with RGDTNF-α AAVP stained to detect apoptotic cells. The blood vessel and surrounding tumor cells showed apoptosis seen in blue colored cells stained with TACS blue label (left panel, 200×). The samples are counterstained with nuclear fast red. The right panel shows blood vessels stained with CD31 specific antibody (200×).

(FIG. 18A) The animals treated with RGDTNF-α showed statistically significant (p<0.05) reduction in tumor volume starting at day 20. (FIG. 18B) The TNF-α resistant human melanoma was made sensitive to TNF-α therapy by delivery of EMAP-II through AAVP followed by treatment with recombinant TNF-α. Mice treated with either rTNF-α or targeted AAVP expressing EMAP-II (RGDEMAP-II) alone showed very little effect and were not significantly different than PBS or fdEMAP-II group. Mice treated with combination of RGD-EMAP-II virus and rTNF-α showed significant reduction in tumor volume (p=0.007).

Figure 1A:
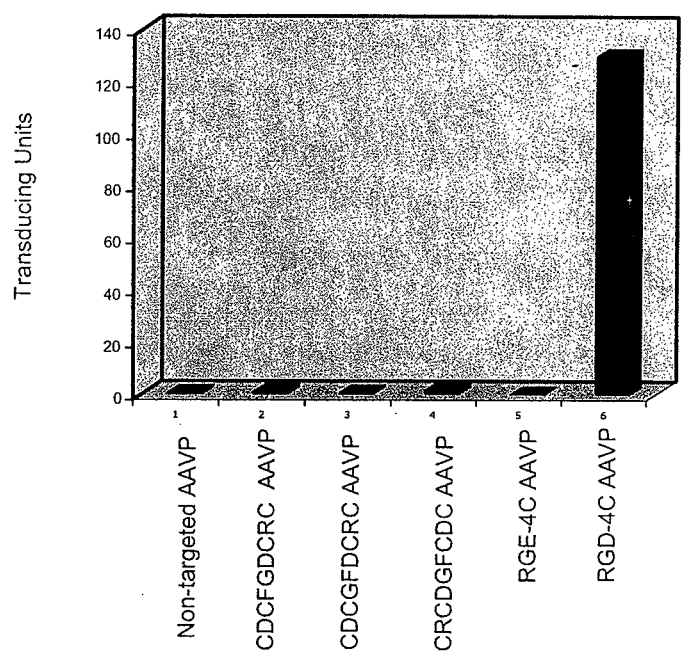
FIGS. 1A-1E FIG. 1A is a graph showing binding of RGD-4C AAVP to mammalian cells expressing αv integrins, in contrast to the non-targeted AAVP or AAVP displaying negative control peptides such as RGE-4C or various scrambled versions of the RGD-4C sequence.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION OF THE INVENTION

The present disclosure, according to certain embodiments, is generally directed to methods of delivering one or more transgenes to a target cell, such as a tumor cell, in a site-specific manner to achieve enhanced expression and to constructs and compositions useful in such applications. In certain aspects, expression from a therapeutic nucleic acid may be assessed prior to administration of a treatment or diagnostic procedure to or on a subject. In a further aspect, the determination or evaluation of expression in the region or location needed for therapeutic benefit is assessed and any unnecessary or marginal beneficial treatment can be with held in lieu of alternative treatments.

Without wishing to be bound by theory or mechanism, the present disclosure is based on the observation that transgene expression may be increased when the transgene is integrated into a genome with a multiplicity greater than one. Of particular interest is the ability of certain chimeric AAVP particles to transduce cells with more than one copy of the transgene, often as a concatamer. Transduced cells also may be monitored by the expression of a reporter gene carried by the chimeric AAVP particles. Any transgene may be included in and expressed from an AAVP particle of this disclosure.

I. ADENO-ASSOCIATED VIRAL/PHAGE (AAVP) PARTICLE

Adeno-associated virus (AAV) is a defective member of the parvovirus family. The AAV genome is encapsulated as a single-stranded DNA molecule of plus or minus polarity. Strands of both polarities are packaged, but in separate virus particles and both strands are infectious. The single-stranded DNA genome of the human adeno-associated virus type 2 (AAV2) is 4681 base pairs in length and is flanked by inverted terminal repeat sequences (ITRs) of 145 base pairs each. In addition, the viral rep protein appears to mediate nonhomologous recombination through the ITRs. Accordingly, as parvoviral genomes have ITRs at each end which play a role in recombination and which are generally required for parvoviral replication and packaging, AAVPs of the present disclosure generally contain all or a portion of at least one of the ITRs or a functional equivalent thereof.

AAVs may be readily obtained and their use as vectors for gene delivery has been described in, for example, Muzyczka, 1992; U.S. Pat. No. 4,797,368, and PCT publication WO 91/18088. Construction of AAV vectors is described in a number of publications, including Lebkowski et al., 1988; Tratschin et al., 1985; Hermonat and Muzyczka, 1984.

The present disclosure provides adeno-associated viral (AAV) bacteriophage vectors (such as AAV-M13 vectors) (AAVPs) that are produced in bacteria and methods for expressing a transgene in a target cell, such as a tumor cell, by transducing the cell with the AAVP. Once purified, a targeted bacteriophage particle containing the bacteriophage and AAV sequences with transgene cassette are used to transfect mammalian cells. Following internalization of the vector within the mammalian cell, the transgene is integrated into the genome of the target cells. The term "vector" as used herein is defined as a nucleic acid vehicle for the delivery of a nucleic acid of interest into a cell. The vector may be a linear molecule or a circular molecule.

An AAVP combines selected elements of both phage and AAV vector systems, providing a vector that is simple to produce in bacteria with no packaging limit, while allowing infection of mammalian cells combined with integration into the host chromosome. Vectors containing many of the appropriate elements are commercially available, and can be further modified by standard methodologies to include the necessary sequences. At minimum, for use with the methods of the present disclosure, the vector must accept a cassette containing a promoter and a transgene. The AAVP vectors of the present disclosure allow for enhanced transgene expression upon incorporation into the target cell genome. In certain embodiments, the transgene may be integrated into the genome of the target cell as a concatamer.

Among other things, AAVPs do not require helper viruses or trans-acting factors. In addition, the native tropism of AAV for mammalian cells is eliminated since there is not AAV capsid formation.

A. AAVP Targeting

The AAVPs of the present disclosure can be targeted to specific receptors by the expression of ligands on the surface of the phage particle. In certain embodiments, peptides or other moieties that allow or promote the escape of the vectors (and any molecule attached thereto or enclosed therein) from the endosome may be incorporated and expressed on the surface of the phage. Such "other moieties" include molecules that are not themselves peptides but which have the ability to disrupt the endosomal membrane, thereby facilitating the escape of the vector, and molecules that otherwise mimic the endosomal escape properties of the within described peptide sequences (see, e.g., published PCT Publication WO 96/10038 and Wagner et al., 1992).

The AAVP of the present disclosure are generally comprised of filamentous phage particles expressing one or more preselected ligands on the particle surface, irrespective of the manner in which the ligands are attached. Therefore, whether the means of attachment for a ligand is covalent or via a capsid protein, the AAVP of the present disclosure are able to deliver one or more transgenes to target cells by ligand binding to a receptor followed by internalization of the vectors. For example, the ligand particle expressed on the particle surface may be bicyclic CDCRGDCFC (RGD-4C) (SEQ ID NO:2) peptide that selectively binds $\alpha v\beta 3$ and $\alpha v\beta 5$ integrins. These integrins are highly overexpressed on invading tumor endothelial cells. As used herein, "filamentous phage particle" refers to particles containing either a phage genome or a phagemid genome. The particles may contain other molecules in addition to filamentous capsid proteins. As used herein, "ligand" refers to any peptide, polypeptide, protein or non-protein, such as a peptidomimetic, that is capable of binding to a cell-surface molecule and internalizing. As used herein, to "binding to a receptor" refers to the ability of a ligand to specifically recognize and detectably bind to a receptor, as assayed by standard in vitro or in vivo assays.

Typically, the AAVPs of the present disclosure include an oligonucleotide insert in the phage plasmid genome encoding a targeting peptide, which allows for ligand-receptor targeting properties of the vectors.

Phage capsid proteins or capsid proteins may be modified by coupling or fusing all or part of a capsid protein polynucleotide or protein encoded by the polynucleotide to a targeting ligand. The targeting ligand may direct, redirect, target or enhance binding of the AAVP of the invention to a specific cell, tissue and/or organ.

Targeted viruses were originally created to overcome problems encountered by gene therapy vectors' natural host cell tropisms. In recent years, many gene therapy patents have issued wherein the vector contains a heterologous polypeptide used to target the vector to specific cells, such as vectors containing chimeric fusion glycoproteins (Kayman et al., U.S. Pat. No. 5,643,756, incorporated herein by reference) and vectors that contain an antibody to a virus capsid protein (Cotten et al., U.S. Pat. No. 5,693,509). An AAVP of the invention may be genetically modified in such a way that the particle is targeted to a particular cell type (e.g., smooth muscle cells, hepatic cells, renal cells, fibroblasts, keratinocytes, stem cells, mesenchymal stem cells, bone marrow cells, chondrocyte, epithelial cells, intestinal cells, neoplastic or cancerous cells and others known in the art) such that the nucleic acid genome is delivered to a target non-dividing, a target dividing cell, or a target cell that has a proliferative or other disorder. One way of targeting viruses is to direct the virus to a target cell by preferentially binding to cells having a molecule on the external surface of the cell. This method of targeting the virus utilizes expression or incorporation of a targeting ligand on or into the capsid of the virus to assist in targeting the virus to cells or tissues that have a receptor or binding molecule which interacts with the targeting ligand on the surface of the virus. After infection of a cell by the virus the genetic material can be processed and expressed in the host cell. The genetic material may be integrated into the genome of the host cell or episomally maintained within the host cell.

In certain embodiments of the invention, a capsid protein may be modified to include a targeting moiety such that an AAVP may be delivered to specific cell types or tissues. The targeting specificity of the ligand-based delivery systems are based on the distribution of the ligand receptors on different cell types. A targeting ligand may either be non-covalently or covalently associated with a capsid protein.

In certain embodiments, a heterologous nucleic acid sequence of interest may be inserted into the viral vector of the invention. For example, a capsid protein may be operatively coupled to a ligand for a receptor on a specific target cell.

Targeting ligands are any ligand specific for a characteristic component of the targeted region. Preferred targeting ligands include proteins such as polyclonal or monoclonal antibodies, antibody fragments, or chimeric antibodies, enzymes, peptides or hormones, or sugars such as mono-, oligo- and polysaccharides. In certain embodiments of the invention, contemplated targeting ligands interact with integrins, proteoglycans, glycoproteins, receptors, or transporters. Suitable ligands include any that are specific or selective for cells of the target organ, or for structures of the target organ exposed to the circulation as a result of local pathology, such as tumors.

In certain embodiments of the present invention, in order to enhance the transduction of resistant cells, to increase transduction of target cells, or to limit transduction of undesired cells, antibody or cyclic peptide targeting moieties (ligands) may be associated with the AAVP. The antibody targeting moiety in particular example is a monoclonal anti-EGF receptor antibody. EGF receptors are distributed on the cell surface of various organs and are present in burns, wounds, dermis and tumors. The peptide targeting moiety may also be a cyclic peptide containing within its sequence a RGD integrin binding motif. Ligands such as the RGD peptide that bind to integrins on the cell surface can mediate internalization, thus increasing the efficiency of delivery of the targeted complex. The targeting peptide may include an RGDFV (SEQ ID NO:3) sequence, wherein the peptide includes the RGD sequence in which the peptide is from 3 to 30 amino acids in length. In other embodiments the RGD integrin binding motif is from 3 to 20 amino acids in length or 4 to 10 amino acids in length. In particular embodiments of the present invention, the RGD integrin binding motif is a peptide 5 amino acids in length. Although cyclic peptides which contain the RGD integrin binding motif within its sequence are preferred, linear peptides may also be utilized in the present invention. 20060239968 Compositions and methods of use of targeting peptides for diagnosis and therapy of human cancer. U.S. Patent publications 20060094672, 20050191294, 20050187161, 20050074812, 20050074747, 20050037417, 20050003466, 20040170955, 20040131623, 20040096441, 20040071689, 20040048243, 20030152578, 20030113320, and 20010046498, as well as PCT publications WO 2006/060171, WO 2006/010070, WO 2005/065418, WO 2005/026195, WO 2004/020999, WO 2003/022991, WO 2002/020822, WO 2002/020769, WO 2002/020723, and WO 2002/020722, describe various compositions and methods of identifying targeting ligands, each of which is incorporated herein by reference in its entirety.

As used herein, "ligand" refers to any peptide, polypeptide, protein or non-protein, such as a peptidomimetic, that is capable of binding to a cell-surface molecule and internalizing. As used herein, to "bind to a receptor" refers to the ability of a ligand to specifically recognize and detectably bind to a receptor, as assayed by standard in vitro or in vivo assays.

Within the context of this invention, the ligand is coupled to a protein of a phage (e.g., a capsid protein), either as a fusion protein or through chemical conjugation, and is used to deliver a nucleic acid to a cell. Fragments of ligands may be used within the present invention, so long as the fragment retains the ability to bind to the appropriate cell surface molecule. Likewise, ligands with substitutions or other alterations, but which retain binding ability, may also be used. As well, a particular ligand refers to a polypeptide(s) having an amino acid sequence of the native ligand, as well as modified sequences, (e.g., having amino acid substitutions, deletions, insertions or additions compared to the native protein (muteins)) as long as the ligand retains the ability to bind to its receptor on an endothelial cell and result in delivery of a nucleic acid to a cell.

Ligands also encompass muteins or mutant proteins that possess the ability to bind to its receptor expressing cells and be internalized. Such muteins include, but are not limited to, those produced by replacing one or more of the cysteines with serine. Typically, such muteins will have conservative amino acid changes. DNA encoding such muteins will, unless modified by replacement of degenerate codons, hybridize under conditions of at least low stringency to native DNA sequence encoding the wild-type ligand.

DNA encoding a ligand may be prepared synthetically based on known amino acid or DNA sequence, isolated using methods known to those of skill in the art (e.g., PCR amplification), or obtained from commercial or other sources. DNA encoding a ligand may differ from the above sequences by substitution of degenerate codons or by encoding different amino acids. Differences in amino acid sequences, such as those occurring among the homologous ligand of different species as well as among individual organisms or species, are tolerated as long as the ligand binds to its receptor. Ligands may be isolated from natural sources or made synthetically, such as by recombinant means or chemical synthesis.

It is not necessary that the ligands used in the context of this invention retain any of its in vivo biological activities, other than binding a receptor on a cell and be internalized. If the ligand has been modified so as to lack one or more biological activities, binding and internalization may still be readily assayed, for example, by the following tests or other tests known in the art. Generally, these tests involve labeling the ligand, incubating it with target cells, and visualizing or measuring intracellular label. For example, briefly, the ligand may be fluorescently labeled with FITC or radiolabeled with $^{125}I$, incubated with cells and examined microscopically by fluorescence microscopy or confocal microscopy for internalization.

The ligands may be produced by recombinant or other means in preparation for attachment to phage capsid proteins. The DNA sequences and methods to obtain the sequences of these ligands are well known. Based on the DNA sequences, the genes may be synthesized either synthetically (for small proteins), amplified from cell genomic or cDNA, isolated from genomic or cDNA libraries and the like. Restriction sites to facilitate cloning into the phage or phagemid vector may be incorporated, such as in primers for amplification.

Such molecules include, without limitation, proteins that bind cancer cells, endothelial cells, stromal cells, and the like. Such ligands include growth factors and cytokines Many growth factors and families of growth factors share structural and functional features and may be used in the present invention. Families of growth factors include fibroblast growth factors FGF-1 through FGF-15, and vascular endothelial growth factor (VEGF). Other growth factors, such as PDGF (platelet-derived growth factor), TGF-$\alpha$ (transforming growth factor), TGF-$\beta$, HB-EGF, angiotensin, bombesis, erythopoietin, stem cell factor, M-CSF, G-CSF, GM-CSF, and endoglin also bind to specific identified receptors on cell surfaces and may be used in the present invention. Cytokines, including interleukins, CSFs (colony stimulating factors), and interferons, have specific receptors, and may be used as described herein.

For example, ligands and ligand/receptor pairs include urokinase/urokinase receptor (GenBank Accession Nos. X02760/X74309); $\alpha$-1,3 fucosyl transferase, $\alpha$1-antitrypsin/E-selectin (GenBank Accession Nos. M98825, D38257/M87862); P-selectin glycoprotein ligand, P-selectin ligand/P-selectin (GenBank Accession Nos. U25955, U02297/L23088), VCAM1/VLA-4 (GenBank Accession Nos. X53051/X16983); E9 antigen (Blann et al., Atherosclerosis 120:221, 1996)/TGF$\beta$ receptor; Fibronectin (GenBank Accession No. X02761); type I $\alpha$1-collagen (GenBank Accession No. Z74615), type I $\beta$2-collagen (GenBank Accession No. Z74616), hyaluronic acid/CD44 (GenBank Accession No. M59040); CD40 ligand (GenBank Accession No. L07414)/CD40 (GenBank Accession No. M83312); EFL-3, LERTK-2 ligands (GenBank Accession Nos. L37361, U09304) for elk-1 (GenBank Accession No. M25269); VE-cadherin (GenBank Accession No. X79981); ligand for catenins; ICAM-3 (GenBank Accession No. X69819) ligand for LFA-1, and von Willebrand Factor (GenBank Accession No. X04385), fibrinogen and fibronectin (GenBank Accession No. X92461) ligands for $\alpha_v\beta_3$ integrin (GenBank Accession Nos. U07375, L28832).

Other ligands include CSF-1 (GenBank Accession Nos. M11038, M37435); GM-CSF (GenBank Accession No. X03021); IFN-$\alpha$ (interferon) (GenBank Accession No. A02076; WO 8502862-A); IFN-$\gamma$ (GenBank Accession No. A02137; WO 8502624-A); IL-1-$\beta$ (interleukin 1 alpha) (GenBank Accession No. X02531, M15329); IL-1-$\beta$ (interleukin 1 beta) (GenBank Accession No. X02532, M15330, M15840); IL-1 (GenBank Accession No. K02770, M54933, M38756); IL-2 (GenBank Accession No. A14844, A21785, X00695, X00200, X00201, X00202); IL-3 (GenBank Accession No. M14743, M20137); IL-4 (GenBank Accession No. M13982); IL-5 (GenBank Accession No. X04688, J03478); IL-6 (GenBank Accession No. Y00081, X04602, M54894, M38669, M14584); IL-7 (GenBank Accession No. J04156); IL-8 (GenBank Accession No. Z11686); IL-10 (GenBank Accession No. X78437, M57627); IL-11 (GenBank Accession No. M57765 M37006); IL-13 (GenBank Accession No. X69079, U10307); TNF-$\alpha$ (Tumor necrosis factor) (GenBank Accession No. A21522); TNF-$\beta$ (GenBank Accession No. D12614); GP30 ligand (S68256) for erbB2; and transferrin (GenBank Accession No. DQ923758) for the transferrin receptor.

Still other ligands include PDGF (GenBank Accession No. X03795, X02811), angiotensin (GenBank Accession No. K02215), and all RGD-containing peptides and proteins, such as ICAM-1 (GenBank Accession No. X06990) and VCAM-1 (GenBank Accession No. X53051) that bind to integrin receptors. Other ligands include TNF$\alpha$ (GenBank Accession No. A21522, X01394), IFN-$\gamma$ (GenBank Accession No. A11033, A11034), IGF-I (GenBank Accession No. A29117, X56773, 561841, X56774, S61860), IGF-II (GenBank Accession No. A00738, X06159, Y00693), atrial natriuretic peptide (GenBank Accession No. X54669), endothelin-1 (GenBank Accession No. Y00749), coagulation factor Xa (GenBank Accession No. L00395, L00396, L29433, N00045, M14327), TGF-β1 (GenBank Accession No. A23751), IL-1β (GenBank Accession No. X03833), IL-1β (GenBank Accession No. M15330), and endoglin (GenBank Accession No. X72012).

The family of FGF proteins presently includes FGF-1 (acidic FGF or aFGF), FGF-2 (basic FGF or bFGF), FGF-3 (int-2), FGF-4 (hst-1/K-FGF), FGF-5, FGF-6 (hst-2), FGF-7 (keratinocyte growth factor or KGF), FGF-8, FGF-9, FGF-11 (WO 96/39507), FGF-13 (WO 96/39508), FGF-14 (WO 96/39506), and FGF-15 (WO 96/39509). Other polypeptides that are reactive with an FGF receptor, that is any polypeptide that specifically interacts with an FGF receptor, preferably the high affinity FGF receptor, and is transported by way of endosomes into the cell by virtue of its interaction with the FGF receptor are suitable within the present invention. Ligands also include 4, 5, 6, 7, 8, 9, 10, 15, 20, 25, 30 or more amino acid fragments of the ligands identified herein.

Also contemplated as targeting moieties are antibodies and fragments thereof. Monoclonal antibody fragments may be used to target delivery to specific organs in the animal including brain, heart, lungs or liver. An exemplary method for targeting viral particles to cells that lack a single cell-specific marker is described (U.S. Pat. No. 5,849,718). For example, antibody A may have specificity for tumor, but also for normal heart and lung tissue, while antibody B has specificity for tumor but also normal liver cells. Clearly, the use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed or active in these cells. Antibody B can be coupled to an activator or a universally active gene encoding a factor necessary for the transcription or activation of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the activation factor is delivered, but has no effect because no an anti-proliferative nucleic acid gene is present. In tumor cells, however, both genes are delivered and the activation factor can activate the anti-proliferative nucleic acid, leading to tumor-specific toxic effects.

Antibodies to molecules expressed on the surface of cells are useful within the context of the present invention. Such antibodies include, but are not limited to, antibodies to FGF receptors, VEGF receptors, urokinase receptor, E- and P-selectins, VCAM-1, PDGF receptor, TGF receptor, endosialin, $\alpha_v\beta_3$ integrin, LFA-1, E9 antigen, CD40, cadherins, and elk-1. Antibodies that are specific to cell surface molecules expressed by cells are readily generated as monoclonals or polyclonal antisera. Many such antibodies are available (e.g., from American Type Culture Collection, Rockville, Md.). Alternatively, antibodies to ligands that bind/internalize may also be used. In such a strategy, the phage particles will have antibody on their surface, which will then be complexed to the ligand.

Many other ligands may be employed for the targeting step of AAVP preparations, depending upon the site targeted for AAVP delivery. In certain embodiments, it is contemplated that AAVP are targeted to specific cell types by receptor-mediated endocytosis. For example, lactosyl ceramide, and peptides that target the LDL receptor related proteins, such as apolipoprotein E3 ("Apo E") have been useful in targeting liposomes to the liver (Spanjer and Scherphof, 1983; WO 98/0748). The asialoglycoprotein, asialofetuin, which contains terminal galactosyl residues, also has been demonstrated to target liposomes to the liver (Spanjer and Scherphof, 1983; Hara et al., 1995). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). Thus, these glycoproteins can be conjugated to AAVP of the present invention and are contemplated as useful for targeting specific cells (e.g., macrophages).

Folate and the folate receptor have also been described as useful for cellular targeting (U.S. Pat. No. 5,871,727). In this example, the vitamin folate is coupled to the AAVP capsid protein(s). The folate receptor has high affinity for its ligand and is overexpressed on the surface of several malignant cell lines, including lung, breast and brain tumors. Transferrin mediated delivery systems target a wide range of replicating cells that express the transferrin receptor (Gilliland et al., 1980).

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

In certain aspects, AAVP can be used to target tumor vasculature. Tumor endothelium is an important target for cancer therapy. Targeting a therapeutic gene of interest to the tumor endothelium with minimal toxicity in other tissues remains the primary goal of antivascular gene therapy. Recently, AAVP targeting tumor endothelium have been described. The inventors studied the ability of this vector to deliver a potent antivascular agent, human tumor necrosis factor-α (TNF-α) to human melanomas. TNF-α resistant melanoma was made sensitive to TNF-α treatment by delivering endothelial monocyte activating polypeptide-II (EMAP-II) via AAVP.

AAVP vectors carrying two genes, TNF-α and EMAP-II were evaluated in vitro and in vivo. Human melanoma cells (M21) were studied for AAVP internalization and TNF-α gene expression in vitro. M21/Pmel subcutaneously grown tumors in nude mice were treated systemically through tail vein injections. The localization of targeted AAVP to the tumor vasculature, TNF-α gene expression and apoptosis were examined using immunofluorescence staining, TaqMan RT-PCR and immunohistochemical analysis.

Internalization of targeted AAVP was observed in M21 cells, resulting in high levels of functionally active TNF-α in the culture supernatant. No internalization of non-targeted vector was observed in these cells. Systemic injection of AAVP showed tumor targeted virus delivery with minimal virus localization into normal organs. The AAVP delivery resulted in expression of TNF-α gene product. The expression of TNF-α, induced apoptosis in the blood vessels and surrounding tumor cells resulting in significant tumor regression. Additionally, targeted delivery of AAVP expressing EMAP-II sensitized a TNF-α resistant human melanoma to TNF-α treatment. Targeted AAVP vectors can be used to deliver antivascular agents specifically to tumor vasculature, thus reducing the systemic toxicity.

The AAVP of the invention can be targeted to specific regions of the body by attachment of specific targeting ligands to provide rapid accumulation and concentration of AAVP and, correspondingly, of nucleic acid molecules, in a designated tissue. The ligands contemplated for use in the present invention can be conjugated to the AAVP by a variety of methods. Various compositions and methods for coupling a targeting ligand to a capsid protein are known in the art.

II. NUCLEIC ACIDS

The AAVP of the present disclosure have the ability to deliver one or more transgenes to the nucleus of the target cell, thereby enhancing the expression of the transgene in the target cell. An AAVP may also bestow an advantage in gene expression by means of an altered fate of the transgene cassette through formation of concatamers of the transgene cassette, thereby leading to enhanced gene expression.

The term "transgene," as used herein, refers to a gene or genetic material that has been transferred from one organism to another. A transgene may comprise one or more genes and/or one or more oligonucleotides. For example, a transgene may comprise a reporter gene, a suicide gene, a prodrug converting enzyme, and/or one or more therapeutic genes. As used herein, "oligonucleotide" refers to a short nucleic acid sequence with twenty or fewer base pairs. The term "therapeutic gene," as used herein, is defined as a nucleic acid region, which provides a therapeutic effect on a disease, medical condition, organ, tissue, cell or physiologic characteristic of an organism. As used herein, the term "cassette" as used herein is a nucleic acid which can express a protein, polypeptide, or RNA of interest.

In addition to ligands an AAVP may contain a transgene comprising a reporter gene whose product can be selected for or detected. As referred to herein, a "reporter gene" is a nucleic acid region that encodes for a product that can be detected, such as by fluorescence, enzyme activity on a detectably labeled compound or chromogenic substrate, or fluorescent substrate, and the like; or selected for by growth conditions. Such reporter genes include, without limitation, green fluorescent protein (GFP), β-galactosidase, chloramphenicol acetyltransferase (CAT), luciferase, neomycin phosphotransferase, secreted alkaline phosphatase (SEAP), human growth hormone (HGH), thymidine kinase, and the like. Selectable markers include drug resistances, such as neomycin (G418), hygromycin, and the like. In certain embodiments, a reporter gene that encodes for a secreted protein that can be detected in blood, other bodily fluids, or tissues may be used to measure the level expression of the reporter gene.

In addition to a reporter gene, the transgene also may comprise a therapeutic gene. AAVPs carrying such transgenes may allow for, among other things, imaging a subject (e.g., a human), either in vitro or in vivo. In vitro imaging may allow for non-invasive imaging of the whole subject or of target areas of the subject. After introduction of these transgenes, expression may be imaged using imaging techniques known in the art (e.g., BLI imaging, PET imaging, fluorescent imaging, and the like.) A "subject," as used herein, refers to any mammalian entity, for example, a subject may be an human in need of gene therapy or other treatment.

In other embodiments, the AAVP may contain a suicide gene. The term "suicide gene" as used herein is defined as a nucleic acid which, upon administration of a prodrug, effects transition of a gene product to a compound which kills its host cell. Examples of suicide gene/prodrug combinations which may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside. In certain embodiments, a suicide gene may act in the manner of a therapeutic gene by providing a therapeutic effect on a disease or medical condition as a result of the killing of its host cell.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 8 and about 100 nucleobases in length. The term "polynucleotide" refers to at least one molecule of greater than about 100 nucleobases in length.

Herein certain embodiments, a "gene" refers to a nucleic acid that is transcribed. In certain aspects, the gene includes regulatory sequences involved in transcription, or message production or composition. As will be understood by those in the art, this functional term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

A polynucleotide of the invention may form an "expression cassette." An "expression cassette" is polynucleotide that provides for the expression of a particular transcription unit. That is it includes promoter elements and various other elements that function in the transcription of a gene or transcription unit. An expression cassette may also be part of a larger replicating polynucleotide or expression vector or construct.

These definitions generally refer to a single-stranded molecule, but in specific embodiments will also encompass an additional strand that is partially, substantially or fully complementary to the single-stranded molecule. Thus, a nucleic acid may encompass a double-stranded molecule that comprises one or more complementary strand(s) or "complement(s)" of a particular sequence comprising a molecule.

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A. Expression Constructs

Expression constructs of the invention may include nucleic acids encoding a therapeutic nucleic acid and/or imaging protein. In other aspects, the expression construct may be a therapeutic expression construct that can be used in therapeutic compositions and methods of the invention. In certain embodiments, genetic material may be manipulated to produce expression cassettes and/or expression constructs that encode imaging proteins, targeting proteins and/or therapeutic genes.

Embodiments of the invention may include two separate types of expression cassette or expression construct comprising an expression cassette. One cassette is used in expression of an imaging protein, i.e., a protein that is directly detectable or has an activity of property that is indirectly detectable. Another expression cassette may encode a therapeutic gene. In the context of a therapeutic vector, a therapeutic gene may be a therapeutic gene discussed herein useful in the prophylatic or therapeutic treatment of a disease condition. In the context of gene therapy, the gene may be a heterologous DNA, meant to include DNA derived from a source other than the viral genome which provides the backbone of the vector. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

B. Control Regions

Expression cassettes and/or constructs of the invention, whether they encode an imaging protein or a therapeutic gene(s) will typically include various control regions. These control region typically modulate the expression of the gene of interest.

1. Promoters

Throughout this application, the term "expression construct" is meant to include any type of genetic construct containing a nucleic acid coding for gene products in which part or all of the nucleic acid encoding sequence is capable of being transcribed, e.g., all or part of an imaging protein or therapeutic protein. The transcript may be translated into a protein, but it need not be. In certain embodiments, expression includes both transcription of a gene and translation of mRNA into a gene product. In other embodiments, expression only includes transcription of a therapeutic nucleic acid such as inhibitory RNAs or DNAs.

The nucleic acid encoding a gene product is under transcriptional control of a promoter. A "promoter" refers to a DNA sequence recognized by the machinery of the cell, or introduced machinery, required to initiate the specific transcription of a gene. In particular aspects, transcription may be constitutive, inducible, and/or repressible. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for various retroviral promoters, the HSV thymidine kinase (tk) and SV40 early transcription units.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a targeted human cell. Generally speaking, such a promoter might include either a human, viral promoter or a combination thereof.

In various embodiments, the human cytomegalovirus immediate early gene promoter (CMVIE), the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral, retroviral or mammalian cellular or bacterial phage promoters, which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product as compared with the cell under non-inducing conditions. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline.

In some circumstances, it may be desirable to regulate expression of a transgene in a therapeutic expression vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 1).

In certain indications, it may be desirable to activate transcription at specific times after administration of the gene therapy vector. This may be done with such promoters as those that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

It is envisioned that any of the above promoters alone or in combination with another may be useful according to the present invention depending on the action desired. In addition, this list of promoters should not be construed to be exhaustive or limiting, those of skill in the art will know of other promoters that may be used in conjunction with the promoters and methods disclosed herein.

TABLE 1

TISSUE SPECIFIC PROMOTERS

| Tissue | Promoter |
|---|---|
| Pancreas | Insulin |
| | Elastin |
| | Amylase |
| | pdr-1 pdx-1 |
| | glucokinase |
| Liver | Albumin PEPCK |
| | HBV enhancer |
| | α fetoprotein |
| | apolipoprotein C |
| | α-1 antitrypsin |
| | vitellogenin, NF-AB |
| | Transthyretin |
| Skeletal muscle | Myosin H chain |
| | Muscle creatine kinase |
| | Dystrophin |
| | Calpain p94 |
| | Skeletal alpha-actin |
| | fast troponin 1 |
| Skin | Keratin K6 |
| | Keratin K1 |
| Lung | CFTR |
| | Human cytokeratin 18 (K18) |
| | Pulmonary surfactant proteins A, B and C |
| | CC-10 |
| | P1 |
| Smooth muscle | sm22 α |
| | SM-alpha-actin |
| Endothelium | Endothelin-1 |
| | E-selectin |
| | von Willebrand factor |
| | TIE (Korhonen et al., 1995) |
| | KDR/flk-1 |
| Melanocytes | Tyrosinase |
| Adipose tissue | Lipoprotein lipase (Zechner et al., 1988) |
| | Adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt et al., 1986) |
| Blood | β-globin |

2. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments of the invention, a therapeutic expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

TABLE 2

ENHANCER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 3

| Element | Inducer |
|---|---|
| MT II | Phorbol Ester (TPA) |
| | Heavy metals |
| MMTV (mouse mammary tumor virus) | Glucocorticoids |
| β-Interferon | Poly(rI)X |
| | Poly(rc) |
| Adenovirus 5 E2 | E1a |
| c-jun | Phorbol Ester (TPA), H$_2$O$_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |

TABLE 3-continued

| Element | Inducer |
|---|---|
| Tumor Necrosis Factor | FMA |
| Thyroid Stimulating Hormone α Gene | Thyroid Hormone |
| Insulin E Box | Glucose |

C. Polyadenylation Signals

Polyadenylation signals may be used in therapeutic and/or imaging vectors. Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

D. Therapeutic Genes

AAVP particles of the invention may be used to deliver a variety of therapeutic or imaging agents, including therapeutic expression vectors. The present invention contemplates the use of a variety of different therapeutic genes. For example, genes encoding enzymes, hormones, cytokines, oncogenes, receptors, ion channels, tumor suppressors, transcription factors, drug selectable markers, toxins and various antigens are contemplated as suitable genes for use according to the present invention. In addition, antisense and inhibitory RNA constructs derived from oncogenes are other "genes" of interest according to the present invention.

In accordance with the present invention, a selected gene or polypeptide may refer to any protein, polypeptide, or peptide. A therapeutic gene or polypeptide is a gene or polypeptide which can be administered to a subject for the purpose of treating or preventing a disease. For example, a therapeutic gene can be a gene administered to a subject for treatment or prevention of cancer. Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, Bax, Bak, Bik, Bim, Bid, Bad, Harakiri, Fas-L, mda-7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, -glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, -L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

E. Multigene Constructs and IRES

In certain embodiments of the invention, the use of internal ribosome binding sites (IRES) elements are used to create multigene polycistronic messages (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message. Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

F. Preparation of Nucleic Acids

A nucleic acid may be made by any technique known to one of ordinary skill in the art, such as for example, chemical synthesis, enzymatic production or biological production. A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

III. PHARMACEUTICAL COMPOSITIONS AND ROUTES OF ADMINISTRATION

Where clinical applications are contemplated, it will be necessary to prepare pharmaceutical compositions of the AAVP compositions (therapeutic compositions) in a form appropriate for the intended application. Generally, this will entail preparing compositions that are essentially free of pyrogens, as well as other impurities that could be harmful to humans or animals.

One will generally desire to employ appropriate salts and buffers to render the compositions suitable for introduction into a patient. Aqueous compositions of the present invention comprise an effective amount of the AAVP or other agent dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the AAVP compositions of the present invention, its use as an imaging reagent or in therapeutic compositions is contemplated. Supplementary active ingredients, such as other anti-cancer agents, can also be incorporated into the compositions. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the composition is determined based on the intended goal, such as imaging and/or ameliorating a condition or disease, such as cancer. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

Also contemplated are combination compositions that contain two active ingredients. In particular, the present invention provides for compositions that contain AAVP compositions and at least a second therapeutic, for example, an anti-neoplastic drug.

A. Parenteral Administration

The active compositions of the present invention may be formulated for parenteral administration, e.g., formulated for injection via the intravenous, intramuscular, sub-cutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

To facilitate a better understanding of the present invention, the following examples of specific embodiments are given. In no way should the following examples be read to limit or define the entire scope of the invention.

IV. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

AAVP Targeting

A. Experimental Procedures

Design, Construction, and Generation of Targeted AAVP Particles.

RGD-4C phage and RGD-4C AAVP were engineered in a two-step process: generation of an intermediate (RGD-4C fUSE5-MCS) and subsequent production of RGD-4C phage construct and RGD-4C AAVP. RGD-4C fUSES-MCS contained the oligonucleotide insert encoding the specific targeting peptide RGD-4C and a fragment of the fMCS plasmid that had a multicloning site (MCS) for insertion of the eukaryotic expression cassette. RGD-4C phage-derived fUSE5 DNA and phage-derived fMCS DNA were purified from lysates of host *E. coli* (MC1061). We obtained the intermediate RGD-4C fUSE5-MCS by ligating a 5.4 kb BamHIISacII fragment of the RGD-4C FUSES plasmid to the 4.1 kb BamHI/SacII fragment of the fMCS plasmid. Next, we created a targeted AAVP-GFP by cloning the PacI fragment (2.8 kb) of pAAV-eGFP plasmid (enhanced GFP; Stratagene) from ITR to ITR into the PstI site of RGD 4C fUSES-MSC. Briefly, pAAV was digested with PacI to release a 2.8 kb fragment, which was blunted with DNA polymerase and cloned into the blunted PstI site of RGD-4C fUSES-MSC. To generate the targeted phage constructs without ITRs, a 2.3 kb fragment located between the ITRs of pAAV-eGFP and containing pCMV-GFP and SV40 poly A was released by EcoRI digestion, blunted with DNA polymerase, then cloned into the MCS of RGD-4C fUSES-MSC. To select cells expressing GFP, the BamHI-Sac1 fragment of the pQBI phosphoglycerate kinase-1 (PGK; QBIOgene) promoter and containing a GFPneo fusion sequence was cloned in the NotI site of AAVP or control phage constructs to ensure that cells expressing GFP were G418-resistant. The GFPneo fragment of pQBI PGK was released by BamHI and Sac1 digestion, and blunted with DNA polymerase; then phosphorylated linkers to NotI were added. After NotI digestion, the 1.57 kb GFPneo fragment was cloned into the NotI site of AAVP or non-chimeric phage construct. Finally, to generate a targeted AAVP particle carrying the gene for HSVtk or Luc the BamHI-NotI fragment containing HSVtk or Luc was subcloned into BamHI-NotI site of pAAV plasmid to replace GFP. The ITR-HSVtk-ITR or ITR-Luc-ITR fragments were removed from pAAV-HSVtk and pAAV-Luc then inserted into RGD-4C fUSE5-MCS. Constructs were verified by DNA sequencing and restriction analysis, purified from the culture supernatant of host E. coli (MC1061), re-suspended in PBS and recentrifuged. Resulting supernatants were titrated in E. Coli (k91Kan). Serial dilutions were plated on Luria-Bertani (LB) agar plates containing tetracycline and kanamycin and transducing units (TU) were determined by colony counting.

Mammalian Cell Surface Binding and Internalization Assays.

The inventors used the biopanning and rapid analysis of selective interactive ligands (termed BRASIL) method (Giordano et al., 2001) to evaluate phage binding to intact cells. In brief, KS1767 cells were detached with ethylenediaminetetraacetate (EDTA) and resuspended in Dulbecco's modified Eagle's medium (DMEM) containing 1% BSA at $4 \times 10^6$ cells per ml. The cell suspension (50 µl) was incubated with $10^9$ TU of either RGD-4C AAVP or AAVP clones displaying scrambled versions of RGD-4C (CDCFGDCRC (SEQ ID NO:2), CDCGFDCRC (SEQ ID NO:3), CRCDGFCDC (SEQ ID NO:4)), mutant RGE-4C peptide, or non targeted control. After 2 h, the AAVP/cell mixture (aqueous phase) was transferred to the top of a non-miscible organic phase (200 µl solution in a 400 µl Eppendorf tube) consisting of dibutyl phthalate:cyclohexane (9:1 [v:v], D=1.03 g/ml) and centrifuged at 10,000 g for 10 min at 4° C. The tube was then snap frozen in liquid nitrogen, the bottom of the tube was sliced off, and the cell-AAVP pellet was isolated and membrane-bound AAVP recovered (Giordano et al., 2001).

For cell internalization, KS1767 cells were grown in tissue chamber slides (Lab-Tek II Chamber Slide System; Nalge Nunc International Corp.), washed twice with PBS, incubated with $10^9$ TU of RGD-4C AAVP or control AAVP displaying scrambled versions of RGD-4C or RGE-4C in DMEM containing 1% BSA at 37° C., and washed with PBS to remove unbound AAVP after 4 h incubation. Bound clones to cell membranes were chemically eluted by rinsing cells with 20 mM glycine (pH 2.3). Next, cells were washed three times with PBS, fixed with PBS containing 4% paraformaldehyde (PFA) at RT for 15 min, washed with PBS, permeabilized with 0.2% Triton X-100, washed with PBS, and blocked with PBS containing 1% BSA. Cells were then incubated with a 1:200 dilution of the primary anti-M13 bacteriophage antibody (Amersham) in PBS containing 1% BSA at RT for 2 h, washed with PBS, and incubated with a 1:200 dilution of a Cy3-conjugated anti-rabbit secondary antibody in PBS containing 1% BSA for 1 h at RT. Finally, cells were washed with PBS, fixed with PBS containing 4% PFA, mounted, and visualized in an optical fluorescence microscope.

Rescue of Recombinant AAV from Cells Transduced by AAVP Particles.

Human 293 cells were infected with RGD-4C AAVP-GFPneo or RGD-4C phage-GFPneo. Four days after infection, cells were transfected with an AAV rep- and cap-expressing plasmid (pXX2) (Xiao et al., 1998) and superinfected with wild-type adenovirus type 5 (Ad). Thus, the AAV rep and cap genes were supplied by transfection, and adenovirus helper functions were provided by superinfection. Cells were harvested 72 h post-adenoviral infection and supernatants were then used to infect new 293 cells. GFP expression was analyzed by using FACS 48 h later. In this assay, a functional recombinant AAV was generated from cells transduced with the RGD 4C AAVP-GFP chimera only, but not from cells transduced with the non-chimeric phage-GFP or several controls. Similar results were also obtained with all the RGD-4C AAVP clones but with none of the phage clones.

Generation of Clonal Mammalian Cell Lines.

Human 293 cells were infected with RGD-4C AAVP-GFPneo or RGD-4C phage-GFPneo (at $10^6$ TU per cell in each case). Single-clones (n=9 per group) were isolated under G418 selection and analyzed for GFP expression by FACS at 12 weeks after selection. Stable clones were termed phage clones #1-9 for phage-GFPneo and AAVP clones #1-9 for AAVP-GFPneo.

Tumor Models.

Animal experimentation was reviewed and approved by the Institutional Animal Research Committee. Tumor-bearing mice were established as described (Pasqualini et al., 1997; Arap et al., 1998; Ellerby et al., 1999; Hajitou et al., 2001; Arap et al., 2004; Marchib et al., 2004). Mice were anesthetized by intraperitoneal administration of AvertinB or by gas (2% isoflurane and 98% oxygen) inhalation. Targeted constructs or controls were intravenously administered. Tumor cells were trypsinized, counted, centrifuged, and re-suspended in serum free medium. A total of $10^6$ cells from Kaposi sarcoma (KS1767), bladder carcinoma (UC3) or prostate carcinoma (DU145) lines were implanted subcutaneously into 6 week-old immunodeficient nude mice. The EF43-FGF4 mouse mammary tumor cells ($5 \times 10^4$) were implanted subcutaneously into 6 week-old female BALBIc immunocompetent mice. Tumor volumes were calculated as described (Pasqualini et al., 1997; Arap et al., 1998; Ellerby et al., 1999; Hajitou et al., 2001; Arap et al., 2004; Marchib et al., 2004) and expressed as mean tumor volume*standard deviation (SD). When tumors reached a volume of ~50 mm$^2$ (deemed small) or ~150 mm$^2$ (deemed large) DU145-derived xenografts (day 0), tumor-bearing mice received a single intravenous dose of RGD-4C AAVP-HSVtk, or controls. GVC treatment (80 mg/kg per day, intraperitoneal) started two days later in cohorts of size-matched tumor-bearing mice.

Molecular-Genetic Imaging in Tumor-Bearing Mice.

For non-invasive molecular imaging, we used a model of prostate cancer based on the human cell line DU145 in which male nude mice bearing tumor xenografts in the subcutaneous area of the right shoulder were used. To image the firefly Luc gene expression, tumor-bearing mice received a single-dose (1 50 mg/kg) of the substrate D-luciferin (Xenogen) by intraperitoneal administration. Photonic emission was imaged by using the In Vivo Imaging System 200 (IVIS200; Xenogen, CA) after tail vein administration of targeted RGD-4C AAVP carrying the Luc gene or controls (non-targeted AAVP-Luc, or scrambled RGD-4C AAVPLuc). Imaging parameters: image acquisition time, 1 min; binning, 2; no filter; flstop, 1; field of view, 10 cm. Regions of interest (ROI) were defined manually over the tumors for measuring signal intensities, expressed as photons/sec/cm2/sr.

While BLI can assess transgene-expressing cell viability in experimental systems, it is not clinically applicable. Thus, to assess the viability of the established tumor xenografts, mice were imaged with a microPET scanner (Concorde Microsystems, TN) at 2 h post intravenous administration of [$^{18}$F]-FDG 100 µCi/mouse. [$^{18}$F]-FDG was obtained commercially (PETNet, Houston, Tex.). To image HSVtk gene expression, PET imaging was performed at 1-2 h after intravenous administration of the radiolabeled nucleoside analog [$^{18}$F]-FEAU. PET imaging was performed on a microPET R4 (Concorde Microsystems, Inc.), equipped with a computer-controlled positioning bed, has a 10.8-cm transaxial and 8-cm axial field of view (FOV), it has no septa and operates exclusively in 3-dimensional list mode. Fully 3-dimensional list mode data were collected using an energy window of 350-750 keV and a time window of 6 ns. All raw data were first sorted into 3-dimensional sinograms, followed by Fourier rebinning and OSEM image reconstruction using ASIPRO VM software (Concord Microsystems, TN). Image pixel size was approximately 1 mm transaxially with a 1.2 mm slice thickness.

Radiolabeled [$^{18}$F]-FEAU was synthesized to radiochemical purity greater than 99% by using 5-ethyluracil-2,5-bis-trimethylsilyl ether as the pyrimidine base for condensation with 1-bromo-2-deoxy-2-[$^{18}$F]fluoro-3,5-di-O-benzoyl-α-D-arabinofuranose, as originally described by Alauddin et al. (2003). To quantitate the [$^{18}$F]-FEAU or [$^{18}$F]-FDG-derived radioactivity concentration in tumors and other organs and tissues, regions of interest were drawn on images and the measured values converted from nCi/mm$^2$ into % injected dose per gram (% ID/g; Tjuvajev et al., 1998). Repetitive [$^{18}$F]-FEAU PET imaging was performed at days 3, 5, 10, and 16 post administration of targeted AAVP carrying the HSVtk gene or control non targeted AAVP, as described above; GCV treatment was administered between days 11 and 19. Of note, PET imaging at day 16 was performed at 24 h after GCV dosing to allow for sufficient elimination of GCV, which would otherwise compete with FEAU for phosphorylation by the HSVtk enzyme. PET imaging with [$^{18}$F]-FDG was repeated at day 17 after AAVP administration to assess the viability of residual tumor, if any.

Immunohistochemistry.

Anesthetized mice were killed and perfused with PBS containing 4% PFA. Tumor vascularization was assessed on frozen sections by using a rat anti-mouse CD31 antibody (BD Biosciences). Apoptosis analysis was performed on paraffin-embedded sections with a TUNEL kit (Promega). For phage immunodetection in tissues, paraffin sections were incubated with a rabbit anti-phage primary antibody (Sigma) followed by a peroxidase-conjugated anti-rabbit secondary antibody (Dako). Slides were developed with the substrate-chromogen 3,3'-diaminobenzidine and counterstained with hematoxylin. For GFP immunostaining, organs and tumors were fixed for 2 h in PBS containing 2% PFA and equilibrated for 48 h in PBS containing 15% sucrose. Cryosections were post-fixed in PBS containing 4% PFA for 20 min and blocked with 5% goat serum in PBS containing 1% BSA and 0.1% Triton X-100 (PBS-T). Next, tissue sections were incubated with a rabbit affinity purified GFP antibody (Molecular Probes) in 2% goat serum and 1% BSA. Sections were then stained with the secondary antibody AlexaFluor 488 conjugated goat anti-rabbit (Molecular Probes) in PBS-T and 1% BSA. αv integrin immunostainings were performed on acetone fixed frozen sections of tumors removed from PBS-perfused animals. Sections were incubated for 1 h with the primary rat anti-integrin αv monoclonal antibody (Chemicon), followed by the secondary Cy3 conjugated goat anti-rat antibody (Jackson ImmunoResearch).

Ligand-Directed Particles are Functional in Mammalian Cells.

Figure 1B:
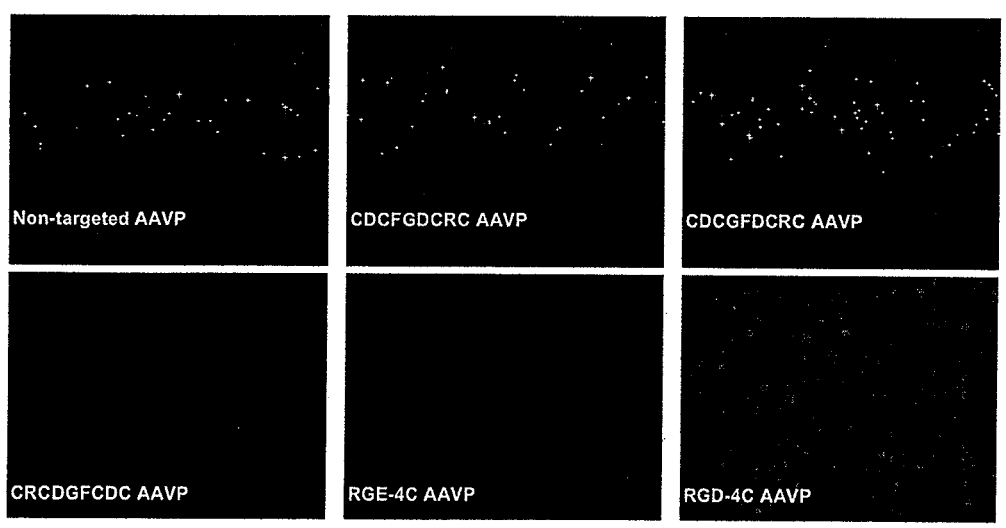
Figure 1C:
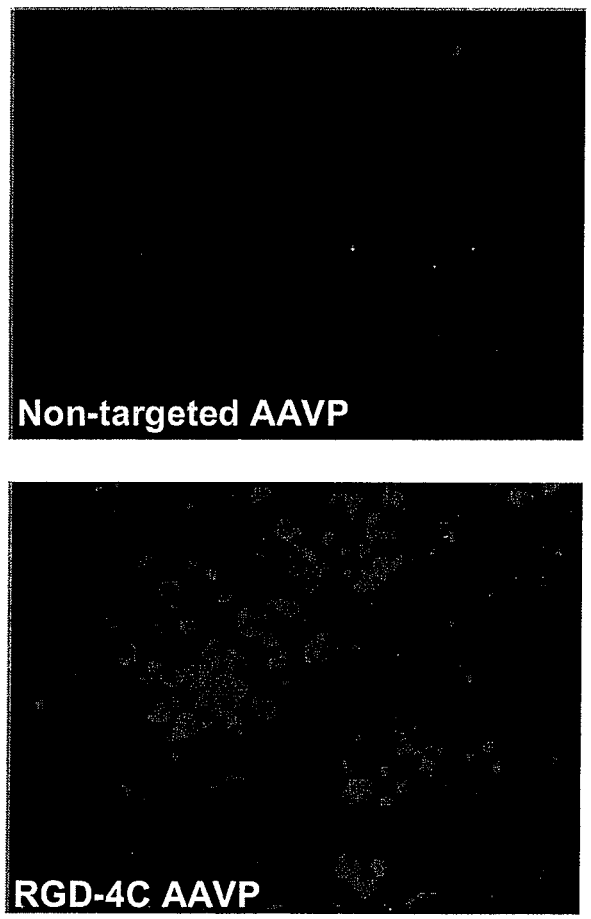
Figure 1D:
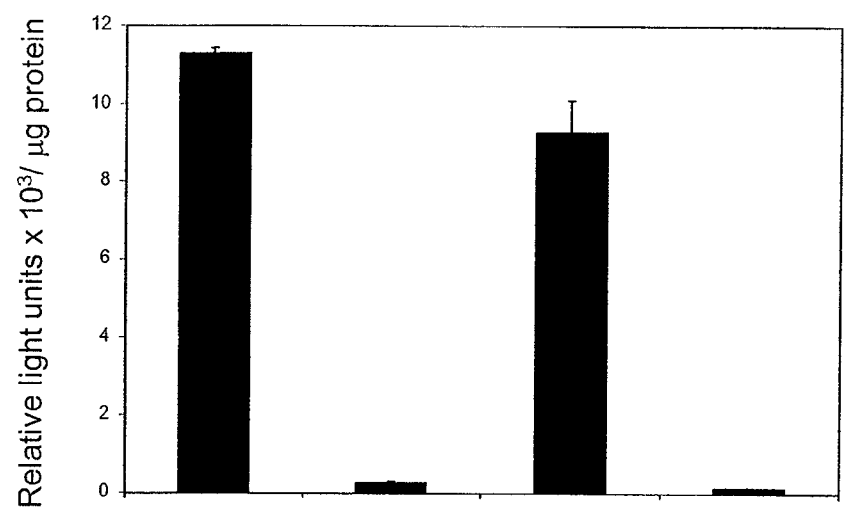
Figure 7:
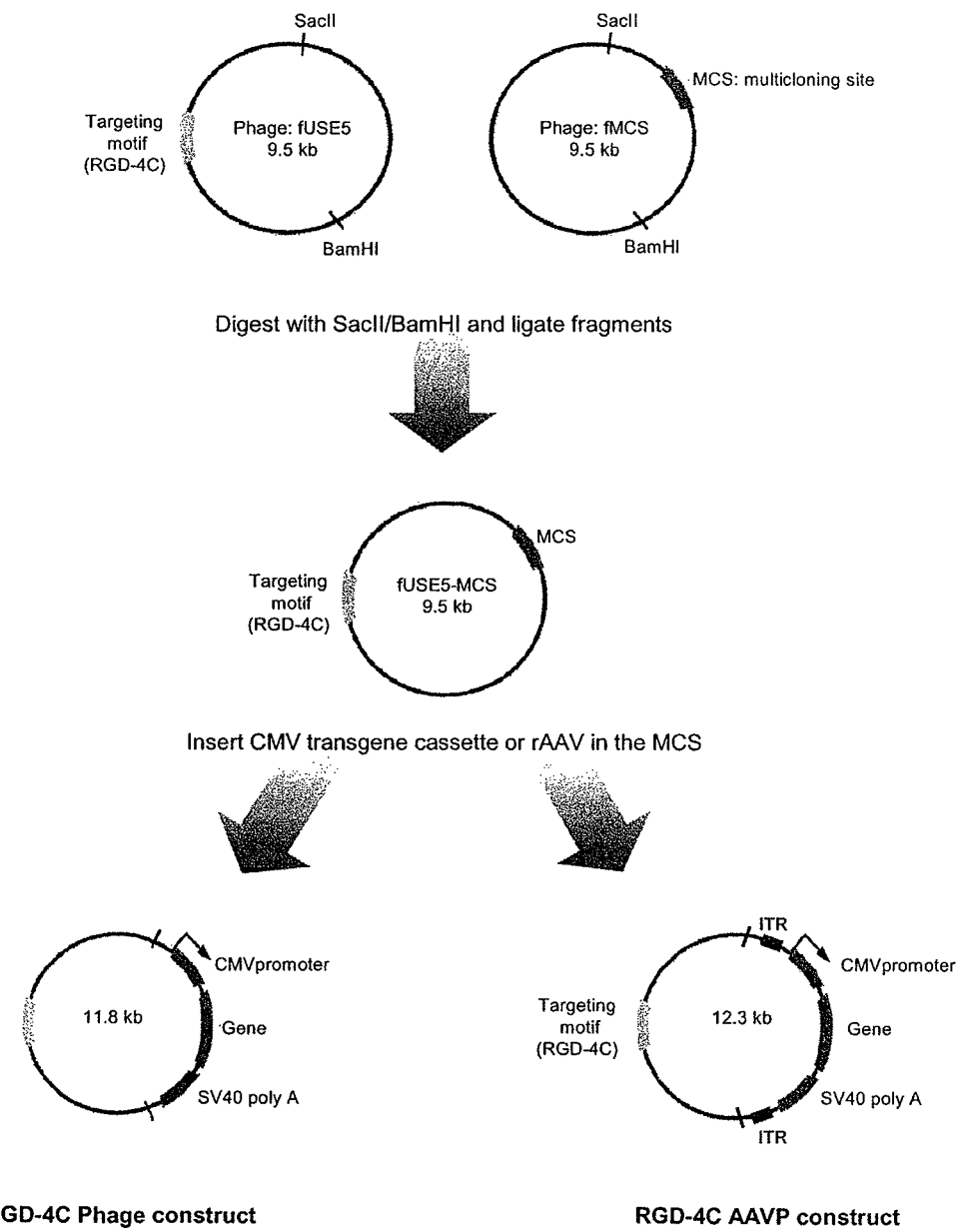
FIG. 7 FIG. 7 is a schematic showing the formation the construction of RGD-4C AAVP, cloning strategy and structure of the resulting vectors are depicted.

A targeted chimeric virus comprising of recombinant AAV and an fd-tet phage clone displaying the double-cyclic peptide CDCRGDCFC (SEQ ID NO:2) (termed RGD-4C phage (Pasqualini et al., 1997; Arap et al., 1998) was constructed. The RGD-4C peptide binds to αv integrins, a cell surface receptor over-expressed in both tumor cells and in neo-angiogenic endothelium of tumor blood vessels (Brooks et al., 1994; Pasqualini et al., 1997; Arap et al., 1998; Sipkins et al., 1998; Ellerby et al., 1999; Hood et al., 2002). To obtain chimeric viruses (further referred to as AAV/phage; AAVP), the inventors inserted an eukaryotic gene cassette from recombinant AAV in an intergenomic region of RGD-4C phage (RGD-4C AAVP), insertless phage (non-targeted AAVP), or phage displaying control peptides, such as scrambled RGD-4C AAVP or D to E mutant (termed RGE-4C) AAVP, and packaged it with the phage DNA into the phage capsid (FIG. 7). In order to show that the cis-elements of the resulting αv integrin targeted chimeric virus remain functional, the inventors evaluated the ligand properties of the RGD-4C peptide and the rescuing properties of the inverted terminal repeats (ITRs) in the context of AAVP. First, to evaluate peptide specificity, it was shown that RGD-4C AAVP binds to mammalian cells expressing αv integrins, in contrast to the non-targeted AAVP or AAVP displaying negative control peptides such as RGE-4C or various scrambled versions of the RGD-4C sequence (FIG. 1A), which neither bind to nor infect mammalian cells. It was also demonstrated that RGD-4C AAVP carrying reporter genes can mediate ligand-directed internalization (FIG. 1B) and transduction of mammalian cells (FIG. 1C) relative to controls. For cell internalization experiments, negative controls included non-targeted AAVP, various RGD-4C scrambled AAVP, or RGE-4C AAVP (FIG. 1B); for cell transduction experiments, non-targeted AAVP (FIG. 1C), scrambled RGD-4C AAVP, or RGE-4C AAVP served as negative controls. Consistent with these results, the inventors have previously demonstrated that the synthetic RGD-4C peptide specifically inhibits cell binding and internalization of various targeted RGD-4C phage based constructs (Giordano et al., 2001; Chen et al., 2004, and unpublished results). Finally, it was shown that mammalian cell transduction can also be specifically competed by the synthetic RGD-4C peptide relative to negative controls such as non-targeted AAVP (FIG. 1D), Scrambled RGD-4C, or RGE-4C. To rule out the possibility that some of these results (FIGS. 1A and 1B) could represent an artifact resulting from selective failure of the glycine (low pH) wash step to remove AAVP from cell membranes, temperature (ice-cold) control experiments were performed (Giordano et al., 2001) in which cell binding was observed but not internalization mediated by RGD-4C AAVP.

Figure 1E:
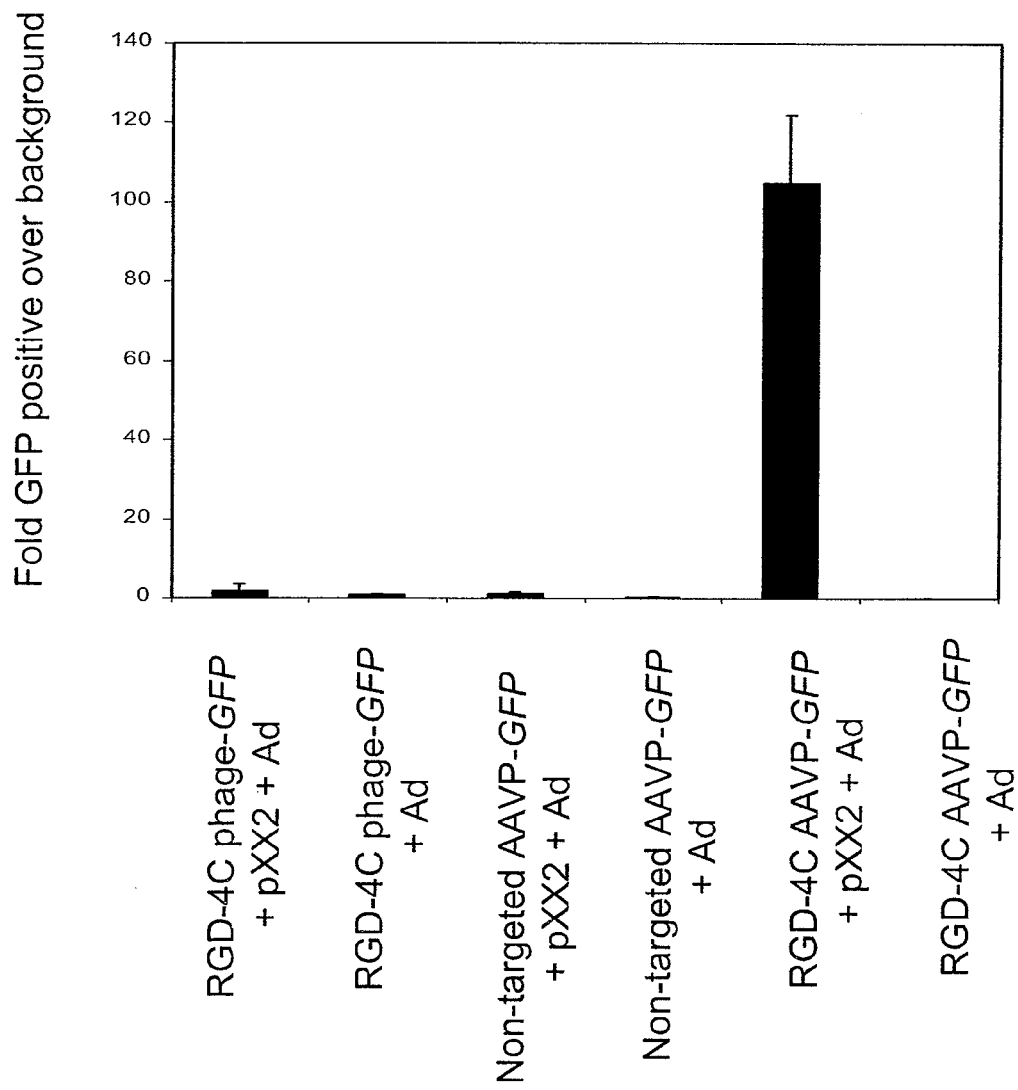

Next, to evaluate whether the ITRs are still functional in the AAVP particle we performed rescue experiments. We show that functional recombinant AAV particles are generated from mammalian cells transduced with the RGD 4C AAVP only, but not from the cells transduced with negative control constructs (FIG. 1E). These data establish that the genetic chimerization resulting in an RGD-4C AAVP particle does not fundamentally alter (i) the peptide targeting properties of the ligand-directed RGD-4C phage or (ii) the ability to rescue recombinant AAV particles from mammalian cells transduced by RGD-4C AAVP. A side-by-side time course of a reporter transgene expression revealed that RGD-4C AAVP transduction was detectable for much longer compared to that of the RGD-4C phage (Table 4).

TABLE 4

Transgene expression in vitro.

| | Post-infection day # | | | | | | | | | | | |
|---|---|---|---|---|---|---|---|---|---|---|---|---|
| | 0 | 5 | 10 | 15 | 20 | 30 | 35 | 40 | 45 | 50 | 55 | 60 |
| RGD-4C-phage | − | ++ | + | − | − | − | − | − | − | − | − | − |
| RGD-4C-AAVP | − | ++ | ++ | ++ | ++ | ++ | ++ | ++ | ++ | + | + | + |

Two independent observers acored GFP expression semi-quantitatively in hiplicate wells of 293 cells per time point.

Molecular Mechanisms of Transgene Expression.

Figure 2A:
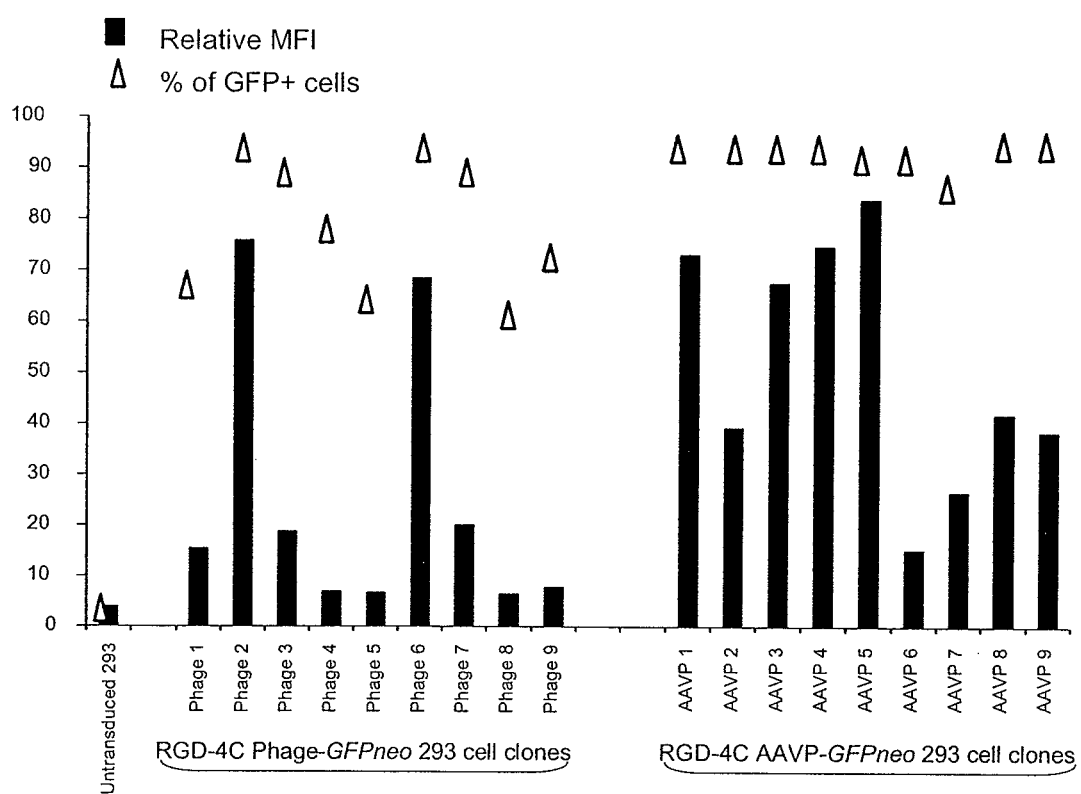
FIGS. 2A-2C FIG. 2A is a histogram showing a summary of flow cytometric analyses of 293 clones stably transduced with either AAVP-GFPneo (n=9) or phage-GFPneo (n=9). Open triangles indicate percentages of green fluorescent protein (GFP)-positive cells and black bars represent GFP expression levels (mean fluorescent intensity; MFI).
Figure 2B:
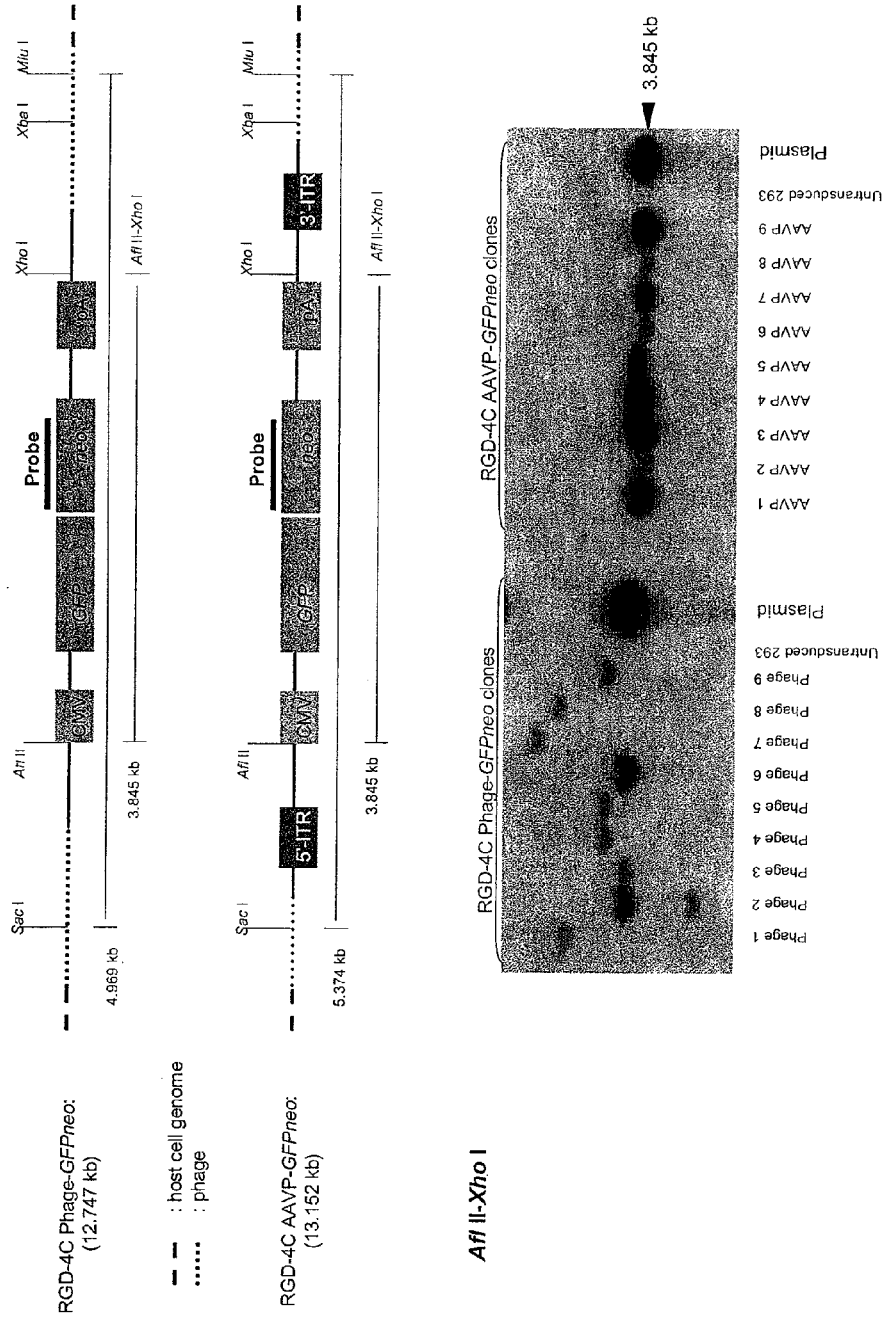
Figure 2C:
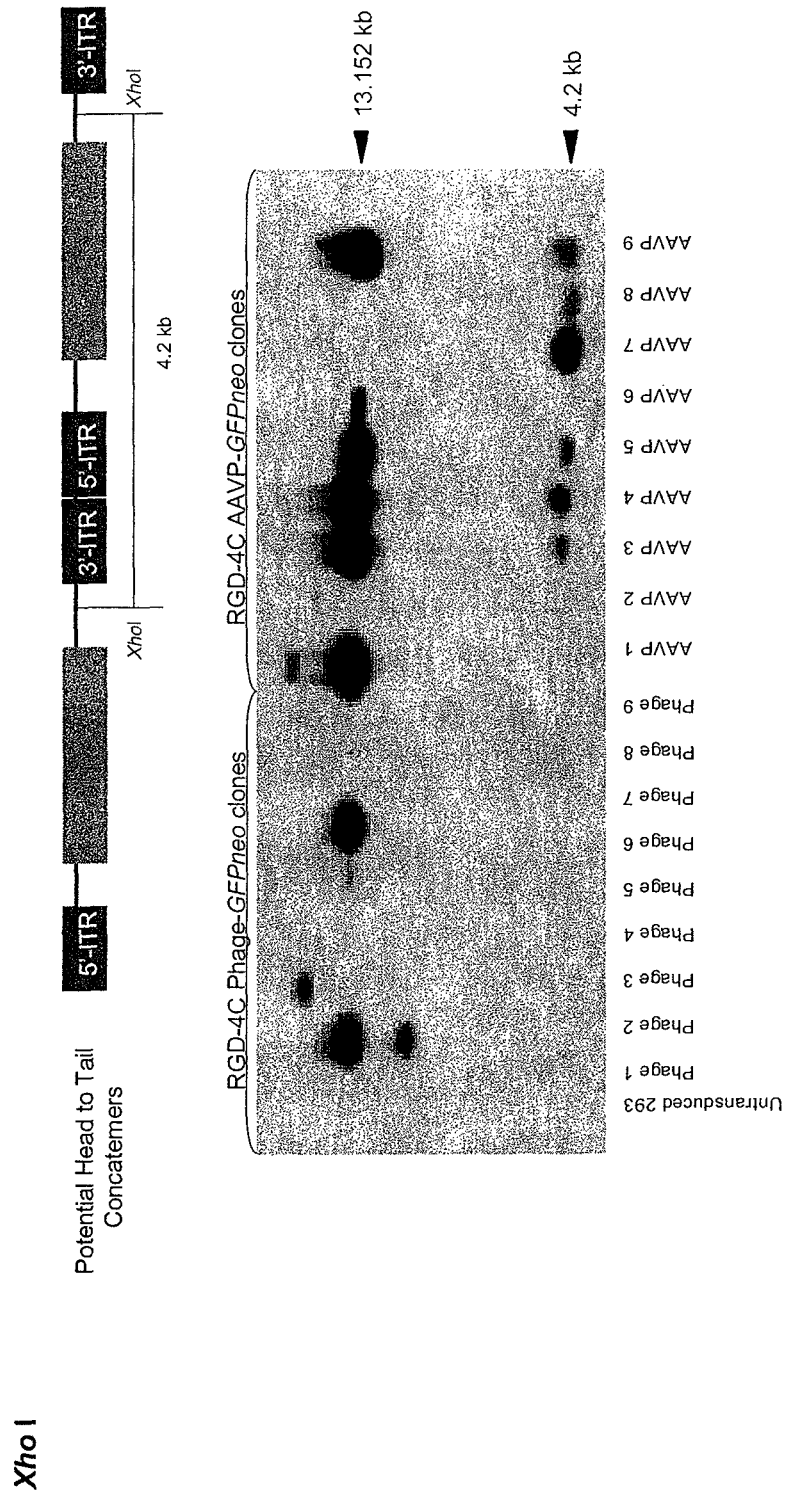
Figure 8A:
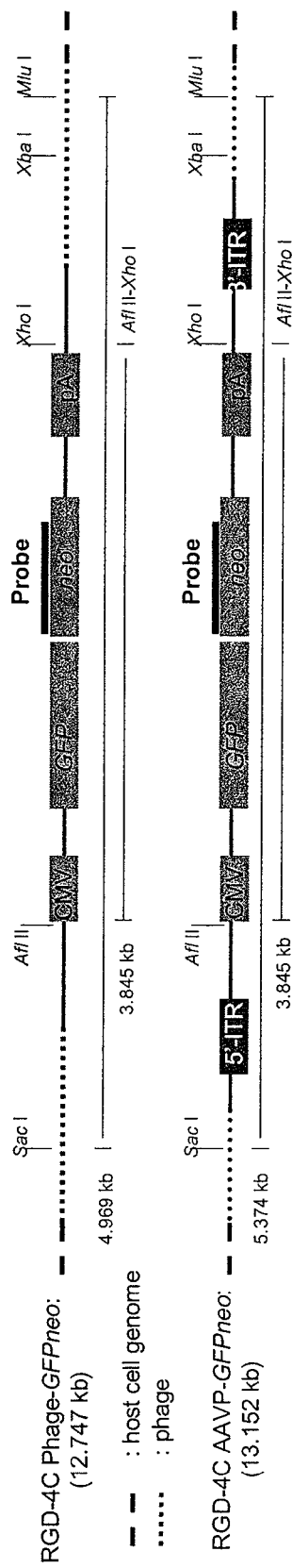
FIGS. 8A-8B FIG. 8A shows a Southern blot analysis of the DNA from RGD-4C AAVP-GFPneo or RGD-4C phage-GFPneo in 293 transduced clonal cell lines. Total cellular DNA from non-transduced 293 parental cells or individual stable cell clones transduced (#1-9 for each vector) was incubated with StuI (no restriction digest site within the vector DNA), Xba-I (single restriction digest site within the vector DNA), or SacI-MluI. Resulting DNA fragments were separated on 0.8% agarose gel, transferred to a nylon membrane and hybridized with a labeled neo probe as indicated. Digested vector plasmids were also used as controls.
Figure 8A:
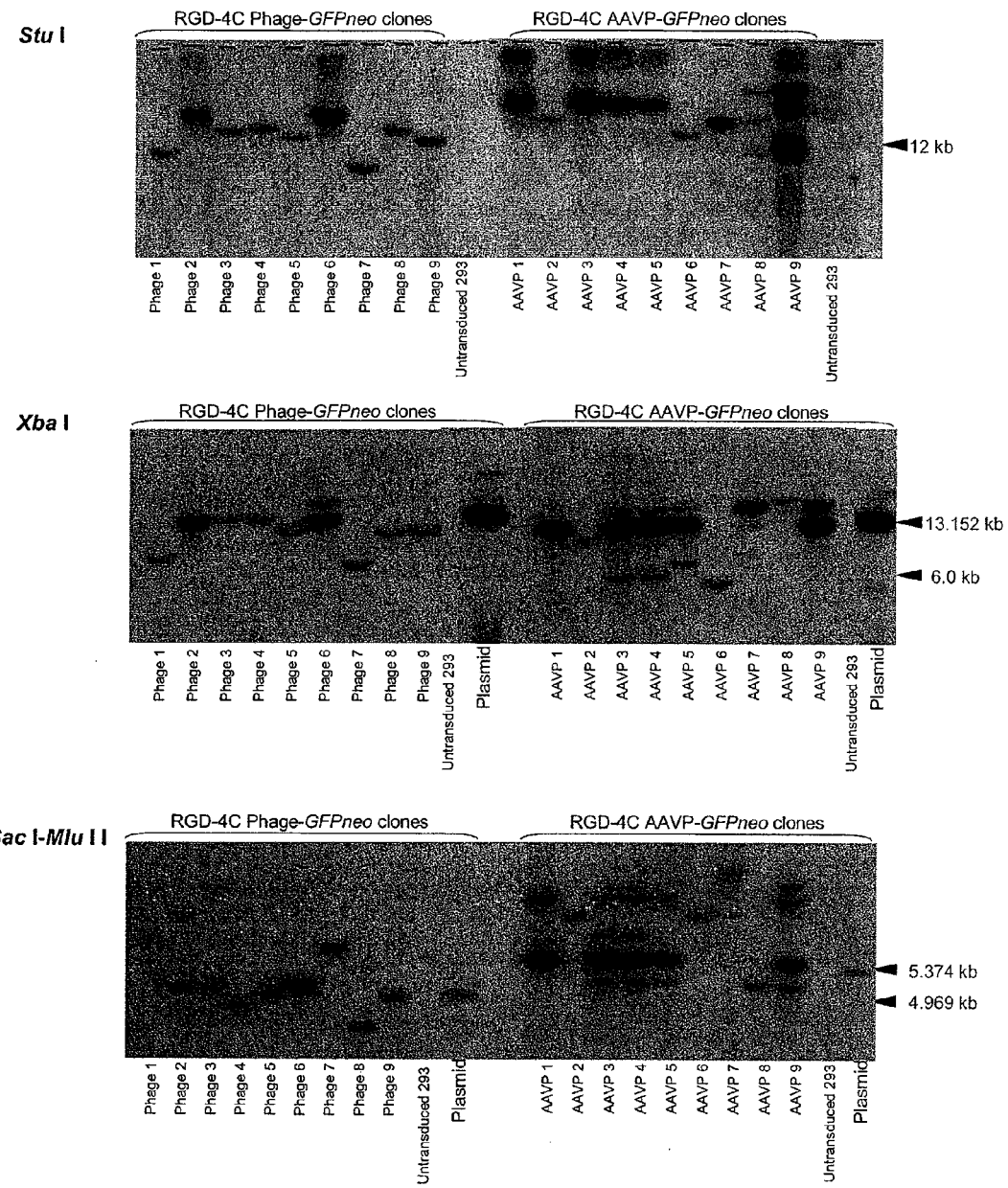
Figure 8B:
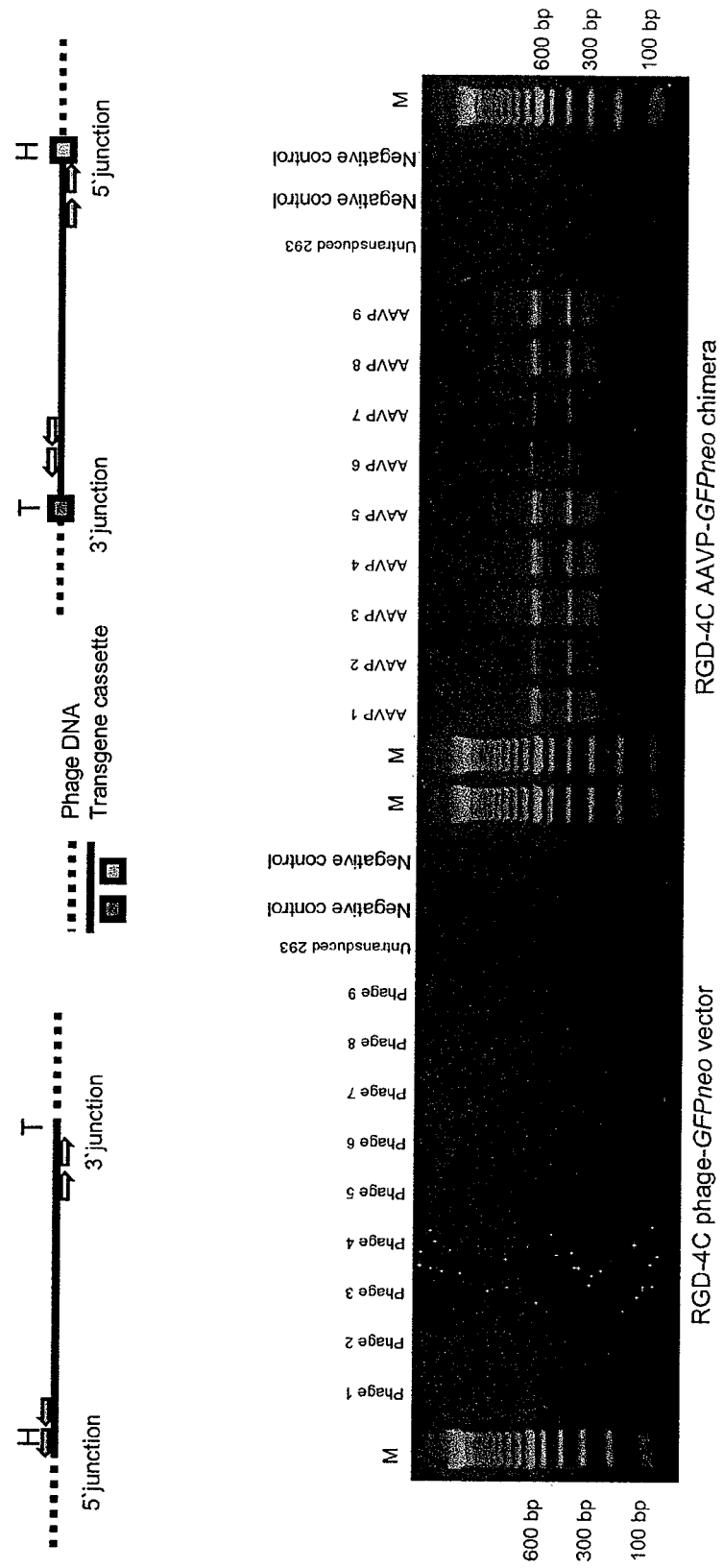

To gain an insight into the molecular mechanisms of transgene expression mediated by AAVP particles, the inventors investigated the fate of the transduced genome in mammalian cells. First, stably transduced cell lines were generated by using GFPneo-expressing AAVP to allow for the selection of individual transduced cell clones. Either RGD-4C AAVP-GFPneo or RGD-4C phage-GFPneo lacking AAV ITRs were used to transduce human 293 cells expressing αv integrins (Nakamura et al., 2002), and clones were isolated under G418 selection. Rescue experiments showed functional recombinant AAV-GFPneo generated from all the RGD-4C AAVP-GFPneo 293 cell clones, but none generated from the RGD-4C phage-GFPneo clones, thus confirming that the chimeric individual clones contain functional ITRs. Although cells transduced with the non-chimeric RGD-4C phage-GFPneo retained G418-resistance, GFP expression was generally weaker than that of the RGD-4C AAVP-GFPneo clones (FIG. 2A). The inventors then set out to determine the fate of the GFPneo transgene cassette in stably transduced clones by a comprehensive restriction enzyme digestion of genomic DNA followed by Southern blotting and polymerase chain reaction (PCR)-based analysis (FIG. 2, FIG. 8, and Table 5). To prove persistence of the transgene cassette, genomic DNA was digested with AflII and XhoI to detect the release of full-length transgene cassettes prior to the analysis. Such release was observed in 100% of the clones transduced by RGD-4C AAVP (n=9 of 9 clones), compared to only in 33% of the clones (n=3 of 9 clones) transduced by the non-chimeric RGD-4C phage construct (FIG. 2B). Another restriction digest of genomic DNA was designed to detect potential concatemeric forms of the transgene cassette (Lieber et al., 1999; Hsiao et al., 2001). The presence of head-to-tail concatemers of the transgene cassette was detected in 67% of the clones transduced by RGD-4C AAVP (n=6 of 9 clones) while no such concatemers were detected in clones transduced by the non-chimeric RGD-4C phage construct (FIG. 2C). To identify possible additional concatemeric forms of the transgene cassette, multiplex PCR was performed by using primers flanking the 5' and 3' ends of the constructs. Again, no concatemers were found in clones transduced by non-chimeric RGD-4C phage construct, whereas 100% of clones transduced by RGD-4C AAVP contained concatemeric forms (n=9 of 9 clones), all of them found in head-to-tail orientation (FIG. 8B). Moreover, top( ) cloning of smaller PCR products revealed the head-to-tail orientation of the transgene cassette with ITR deletions (Yang et al., 1997). Finally, although the large PCR products could not be sequenced, their sizes suggest the presence of concatemers with intact ITRs at the junction site. An individual analysis of DNA for each single clone is also detailed (Table 5). Not wishing to be bound by theory or mechanism, these data suggest that AAVP may bestow an advantage in gene expression by means of an altered fate of the transgene cassette through maintenance of the entire mammalian transgene cassette, better persistence of episomal DNA, formation of concatemers of the transgene cassette, or perhaps by a combination of these non-mutually exclusive mechanisms. These observations are consistent with recent developments in the understanding of AAV (McCarty et al., 2004).

TABLE 5

Fate of the vector DNA in 293 cell clones stably transduced by RGD-4C AAVP-GFneo or RGD-4C phage-GFneo.

| RGD-4C phage or RGD-4C AAVP (denomination of stably transduced clones) | Contains integrated forms of construct | Contains episomal forms of construct | Contains concatemeric forms of transgene cassette | Transgene cassette preserved | Comments and Interpretation |
|---|---|---|---|---|---|
| Phage 1 | Yes | No | No | No | |
| Phage 2 | Yes | Yes | No | Yes (episomal) | Episomal form of full-length phage vector |
| Phage 3 | Yes | No | No | Yes | |
| Phage 4 | Yes | No | No | No | |
| Phage 5 | Yes | No | No | No | |
| Phage 6 | Yes | Yes | No | Yes (episomal) | Episomal form of full-length phage vector |
| Phage 7 | Yes | No | No | No | |
| Phage 8 | Yes | No | No | No | |
| Phage 9 | Yes | No | No | No | |
| AAVP 1 | Yes | Yes | Yes | Yes | Non-concatemeric episomal forms of full-length AAVP vector detected. Concatemeric integrated form with deleted XhoI Site. |
| AAVP 2 | Yes | No | Yes | Yes | Concatemeric form is head-to-tail with deleted ITRs at the junction site. ITRs flanking the concatemer and adjacent AAVP sequences are preserved. |
| AAVP 3 | Yes | Yes | Yes | Yes | Non-concatemeric episomal form of full-length AAVP vector. At least |

TABLE 5-continued

Fate of the vector DNA in 293 cell clones stably transduced by RGD-4C AAVP-GFneo or RGD-4C phage-GFneo.

| RGD-4C phage or RGD-4C AAVP (denomination of stably transduced clones) | Contains integrated forms of construct | Contains episomal forms of construct | Contains concatemeric forms of transgene cassette | Transgene cassette preserved | Comments and Interpretation |
|---|---|---|---|---|---|
| | | | | | one integrated form contains head-to-tail concatemers and ITRs flanking the concatemer as well as the adjacent AAVP sequences are preserved. At least one integrated form contains head-to-tail concatemers with deleted ITRs at the junction site. |
| AAVP 4 | Yes | Yes | Yes | Yes | Non-concatemeric episomal form of full-length AAVP vector. At least one integrated form contains head-to-tail concatemers and ITRs flanking the concatemer as well as the adjacent AAVP sequences are preserved. At least one integrated form contains head-to-tail concatemers with deleted ITRs at the junction site. |
| AAVP 5 | Yes | Yes | Yes | Yes | Non-concatemeric episomal form of full-length AAVP vector. At least one integrated form contains head-to-tail concatemers and ITRs flanking the concatemer as well as the adjacent AAVP sequences are preserved. At least one integrated form contains head-to-tail concatemers with deleted ITRs at the junction site. |
| AAVP 6 | Yes | No | Yes | Yes | Concatemeric are head-to-tail with deleted ITRs and XhoI sites. ITRs flanking the (concatemer) transgene cassette as well as the adjacent AAVP sequences are preserved. |
| AAVP 7 | Yes | No | Yes | Yes | Concatemers are head-to-tail with preserved ITRs. Additional concatemers with deleted ITRs. |
| AAVP 8 | Yes | No | Yes | Yes | At least one integrated form contains head-to-tail concatemers and ITRs flanking the concatemer as well as the adjacent AAVP sequences are preserved. At least one integrated form contains head-to-tail concatemers with deleted ITRs at the junction site. |
| AAVP 9 | Yes | Yes | Yes | Yes | Non-concatemeric episomal form of full-length AAVP vector. At least one integrated form contains head-to-tail concatemers and ITRs flanking the concatemer as well as the adjacent AAVP sequences are preserved. At least one integrated form contains head-to-tail concatemers with deleted ITRs at the junction site. |

Tumor Targeting In Vivo and Molecular-Genetic Imaging.

Figure 9:
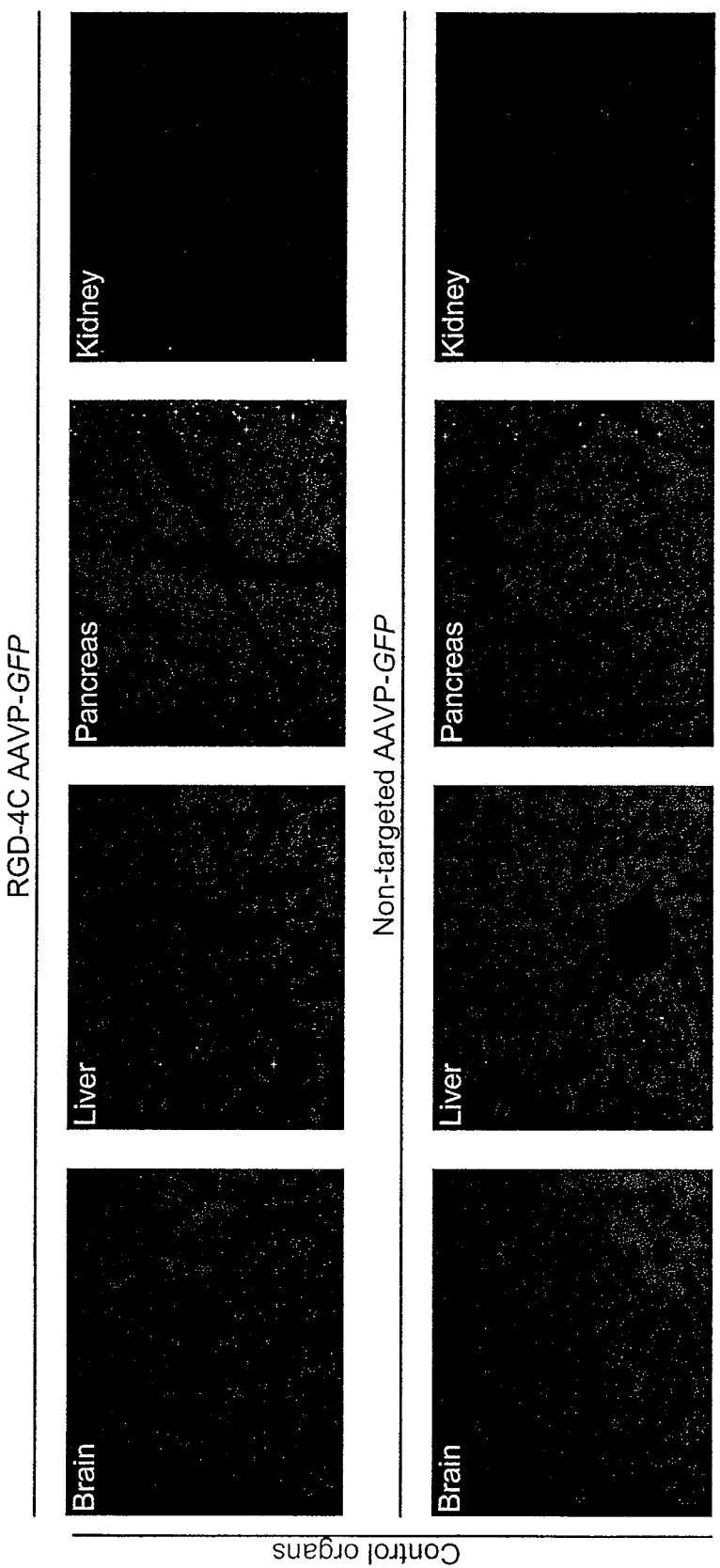
FIG. 9 FIG. 9 is an image showing immunostaining of the reporter gene expression GFP in control organs brain, liver, pancreas, and kidney at day 7 after an intravenous dose ($5 \times 10^{10}$ TU) of either RGD-4C AAVP-GFP or non-targeted AAVP-GFP into mice.

After demonstrating that the central elements of the targeted chimeric viral particle (i.e., the RGD-4C peptide and the AAV ITRs) are intact and functional and after elucidating the molecular mechanisms of AAVP-mediated gene expression in mammalian cells, the specificity and efficacy of gene delivery into tumors after systemic administration of AAVP was evaluated. As an initial preclinical model, nude mice bearing subcutaneous tumor xenografts derived from human Kaposi sarcoma KS 1767 cells were used (Arap et al., 1998; Ellerby et al., 1999). First, to verify that the viral construct targets to KS1767-derived xenografts in mice, either RGD-4C AAVP or one of several negative controls (non-targeted AAVP, scrambled RGD-4C AAVP, or RGE-4C AAVP) were administered intravenously. After a 3-5 min circulation time, a strong anti-AAVP staining in tumor vasculature was observed in mice that received RGD-4C AAVP but not in control mice (FIG. 3A). An RGD-4C AAVP variant encoding the green fluorescent protein (GFP) gene was used as a reporter to determine, by using in situ immunofluorescence microscopic imaging, whether this vector (RGD-4C AAVP-GFP) can transduce KS 1767-derived xenografts. Immunostaining against GFP in tumors and in different organs were performed seven days after systemic administration of either RGD-4C AAVP-GFP or negative control constructs into tumor-bearing mice. Immunofluorescence revealed GFP expression largely in tumor blood vessels and surrounding tumor cells in mice that received RGD4C AAVP-GFP. In contrast, no GFP staining was detected in tumors from control mice that received non targeted, scrambled, or mutant AAVP-GFP (FIG. 3B). This staining pattern suggests that ligand-directed transduction is mediated by targeting of αv integrins in the vascular endothelium of tumors (Brooks et al., 1994; Pasqualini et al., 1997; Arap et al., 1998; Sipkins et al., 1998; Ellerby et al., 1999; Giordano et al., 2001; Hood et al., 2002; Chen et al., 2004). Consistently, several non-target control organs (brain, liver, pancreas and kidney) lacked tissue expression of GFP (FIG. 9). Together, these results indicate that RGD-4C AAVP particles can specifically target tumor xenografts by a ligand-directed mechanism and transduce them after systemic administration in vivo.

Figures 4A, 4B:
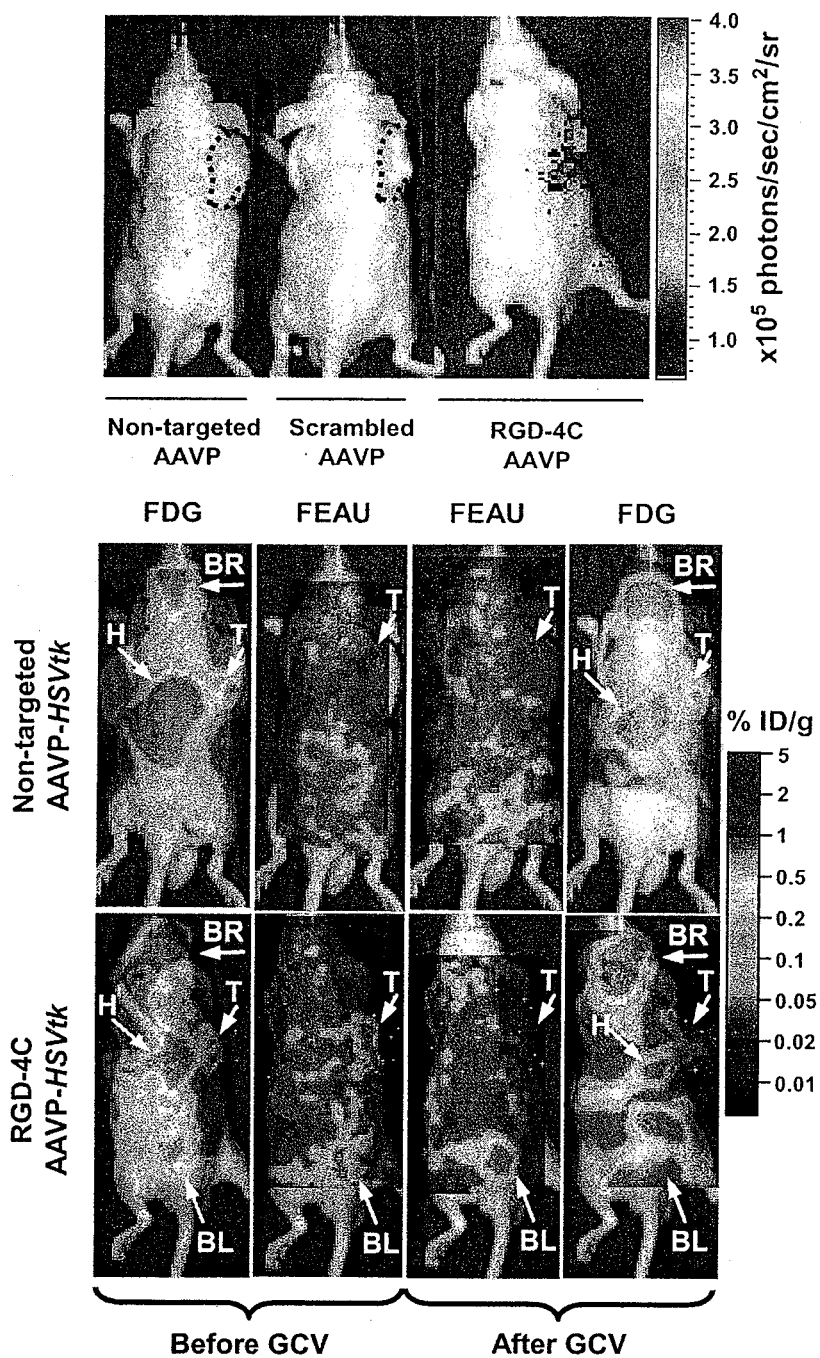
FIGS. 4A-4E FIG. 4A shows in vivo bioluminescent imaging of firefly luciferase expression after systemic delivery of targeted AAVP. Nude mice bearing DU145-derived tumor xenografts received a systemic single-dose of either RGD-4C AAVP-Luc ($5\times10^{11}$ TU, intravenous) or controls (non-targeted AAVP-Luc, or scrambled RGD-4C AAVP-Luc). Ten days later, bioluminescence imaging (BLI) of tumor-bearing mice was performed to assess the transgene expression. Calibration scales are provided in panels.

Next, inventors assessed the efficacy of preclinical bioluminescence imaging (BLI) and clinically applicable molecular-genetic PET imaging with [$^{18}$F]-FEAU for non-invasive monitoring of temporal dynamics and spatial heterogeneity of the firefly luciferase (Luc) and of the HSVtk reporter gene expression, respectively, in living tumor-bearing mice following systemic administration of the RGD-4C AAVP. These molecular-genetic imaging studies were conducted in a preclinical model of human prostate cancer since this particularly prevalent tumor remains a challenge to properly image in patients. The inventors first used a standard experimental setup for in vivo imaging of the firefly Luciferase (Luc) transgene reporters in tumor-bearing mice (FIG. 4A). The inventors selected BLI of Luc expression, because it is a very sensitive method for reporter gene imaging in mice and has virtually no non-specific background activity in the images (Gross and Piwnica-Worms, 2005a; Gelovani and Blasberg, 2003; Uhrbom et al., 2004; Walensky et al., 2004). A very tumor-specific expression of Luc was observed in DU145 tumors in mice receiving RGD-4C AAVP-Luc. In contrast, tumor-associated bioluminescence signals could not be observed in control mice receiving the non-targeted AAVP-Luc or scrambled RGD-4C AAVP-Luc. With all types of AAVP vectors (non-targeted AAVP-Luc, scrambled RGD-4C AAVP-Luc, RGE-4C AAVP-Luc or RGD-4C AAVP-Luc) no bioluminescence was observed in normal organs such as liver, spleen, or kidneys. These data confirm the tumor-specificity of RGD-4C AAVP-mediated targeting and transgene expression observed with immunofluorescence microscopy imaging studies with RGD-4C AAVP-GFP. Consistently with previous results presented here (FIG. 9), the kinetics of distribution suggests that despite the non-specific hepatic clearance of phage particles (Geier et al., 1973; Pasqualini et al., 1997; Arap et al., 1998; Barbas et al., 2001), such phenomenon does not result in an undesirable gene transduction of the liver. These observations are in sharp contrast with the well-documented non-specific transduction of normal organs (such as liver) by the mammalian viral gene delivery vectors (Shayakhmetov et al., 2005). By using BLI in vivo, Luc reporter transgene expression within tumors was clearly detectable at day 3 after AAVP administration and increased gradually to reach maximal levels by day 10. Repetitive 2-dimensional BLI of Luc reporter gene expression was performed every other day and provided an initial cost effective strategy to study the specificity, temporal dynamics, and spatial heterogeneity of reporter transgene expression mediated by AAVP. However, because BLI of Luc reporter gene expression is not clinically applicable, the inventors next introduced into the AAVP vector the HSVtk gene, which can serve both as a suicide gene (when combined with gancyclovir; GCV) and as a reporter transgene for clinically applicable PET imaging with HSVtk-specific radiolabeled nucleoside analogues (e.g., [$^{124}$I]-FAIU, [$^{18}$F]-FHBG, and [$^{18}$F]-FEAU).

Figure 4C:
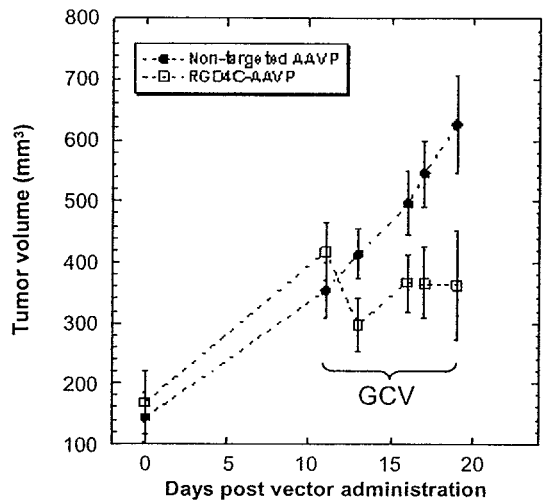
Figure 4D:
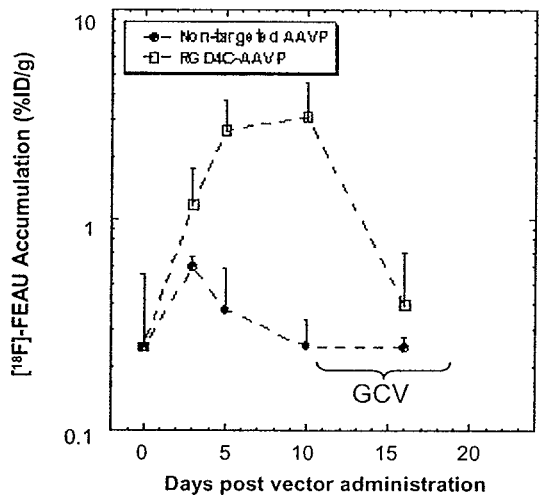
Figure 4E:
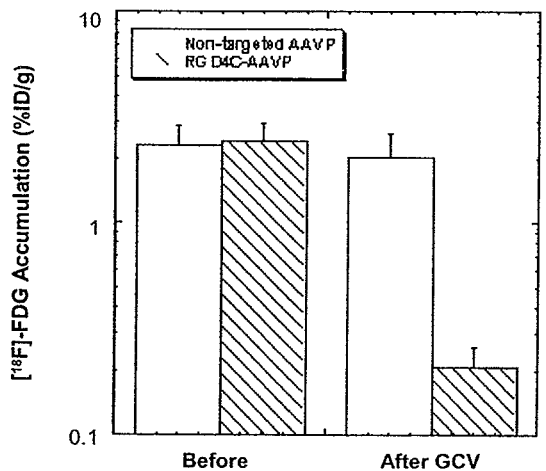

Previous studies established that PET imaging of HSVtk expression provides the ability to define the location, magnitude, and duration of transgene expression (Tjuvajev et al., 1998; Tjuvajev et al., 1999; Ray et al., 2001; Massoud and Gambhir, 2003). It has also been previously determined that the magnitude of accumulated radiolabeled tracers in HSVtk-transduced cell lines and tumors in vivo correlates with the level of HSVtk expression (Blasberg and Tjuvajev, 2003; Gross and Piwnica-Worms, 2005a; Tai and Laforest, 2005). In the studies presented here, the inventors selected, synthesized and used the radiolabeled nucleoside analogue 2'-[$^{18}$F]-fluoro-2'-deoxy-1-β-D-arabino-furanosyl-5-ethyl-uracil ([$^{18}$F]-FEAU), which is a better radiolabeled substrate for the HSVtk enzyme than other nucleoside analogues, especially from pharmacokinetic considerations (a very low background activity in all normal organs and tissues) (Kang et al., 2005). By using repetitive PET imaging with [$^{18}$F]-FEAU (on days 0, 3, 5, 10, and 16), the inventors have visualized and quantitated the temporal dynamics and spatial heterogeneity of HSVtk gene expression after a single systemic administration of RGD-4C AAVP-HSVtk or non-targeted AAVP-HSVtk in DU145-derived tumor xenografts and other organs and tissues in nude mice (FIG. 4B). Tumor xenograft sizes (approximately 150 mm$^2$) before, as well as tumor growth rates after administration of either RGD4C AAVP-HSVtk or non-targeted AAVP-HSVtk were similar in both cohorts of mice (FIG. 4C). PET imaging with [$^{18}$F]-FEAU revealed a gradual increase in the level of HSVtk transgene expression in tumors (increase in % administered intravenous dose per gram) during the initial five days after administration of RGD-4C AAVP-HSVtk, followed by gradual stabilization of HSVtk expression levels towards day 10 post vector administration. In contrast, in control tumor-bearing mice receiving nontargeted AAVP-HSVtk, only a minor increase in tumor accumulation of [$^{18}$F]-FEAU was observed at day 3, which rapidly decreased to background level (FIG. 4D). Consistent with preceding BLI experiments, no [$^{18}$F]-FEAU PET detectable HSVtk expression was observed in non-target organs or tissues (FIG. 4B). Indeed, low-level heterogeneous activity in the PET images represents normal background activity, which was intentionally intensified in images to demonstrate that no truncation of low levels of radioactivity was made to artificially "improve" the specificity of HSVtk expression in tumors versus non-target tissues. When tumors grew to reliably palpable sizes (approximately 350-400 mm$^2$), and a plateau of HSVtk expression was achieved in tumors, treatment with GCV was initiated in all cohorts of animals (FIG. 4C). PET imaging with [$^{18}$F]-fluorodeoxyglucos ([$^{18}$F]-FDG) served to monitor glucose metabolism and GCV-induced changes in tumor viability. Two days before initiation of GCV therapy (day 9 post vector administration), the DU145 tumors in both groups of mice were viable and actively accumulated [$^{18}$F]-FDG (FIG. 4E). After GCV therapy, the volume of tumors in mice that received RGD-4C AAVP-HSVtk was significantly smaller than in mice that received non-targeted AAVP-HSVtk (p<0.05; FIG. 4C). Moreover, tumor xenografts were also metabolically suppressed as evidenced by a decrease in accumulation of [$^{18}$F]-

FDG (FIG. 4E). The levels of HSVtk expression in tumors of mice administered with RGD-4C AAVP-HSVtk were also significantly decreased after GCV therapy, as evidenced by a sharp decrease in [$^{18}$F]-FEAU accumulation in PET images (FIG. 4D), which were obtained 24 h after the last GCV dose (to avoid competition with FEAU). These studies confirm the specificity of tumor targeting by RGD-4C AAVP and demonstrate that the level of HSVtk transgene expression is adequately high for effective prodrug activation of GCV.

Figure 5A:
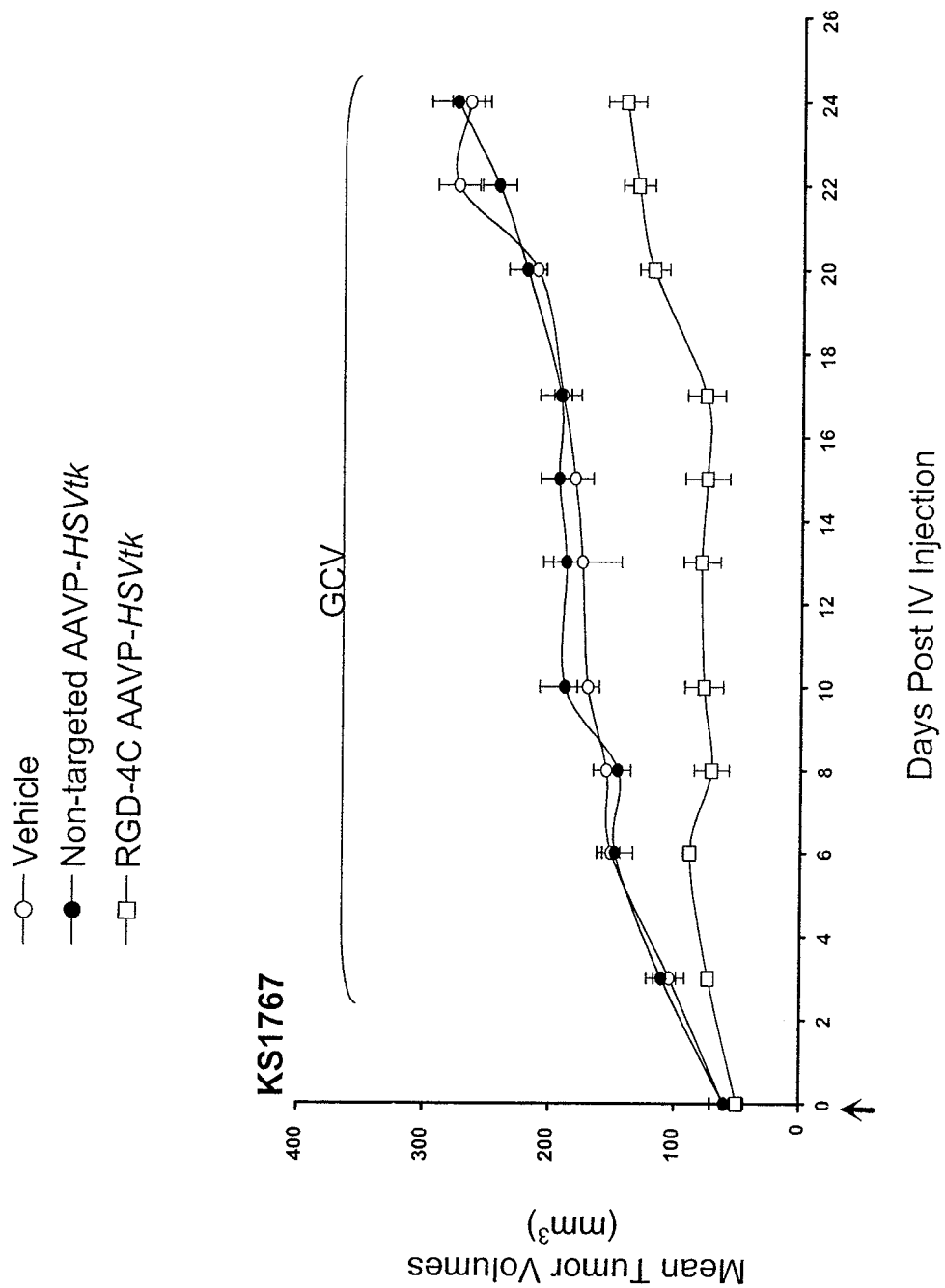
Figure 5C:
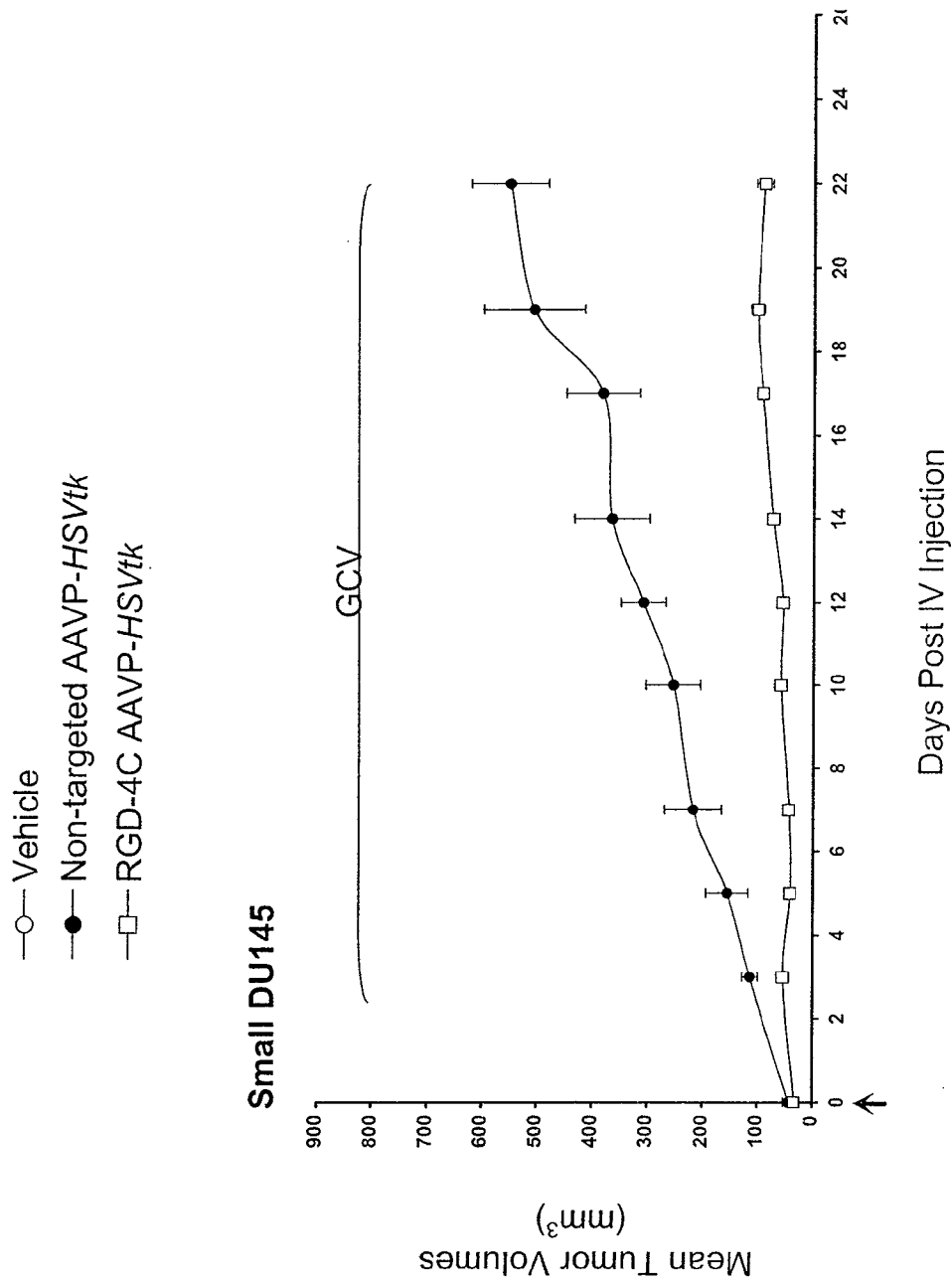
Figure 5F:
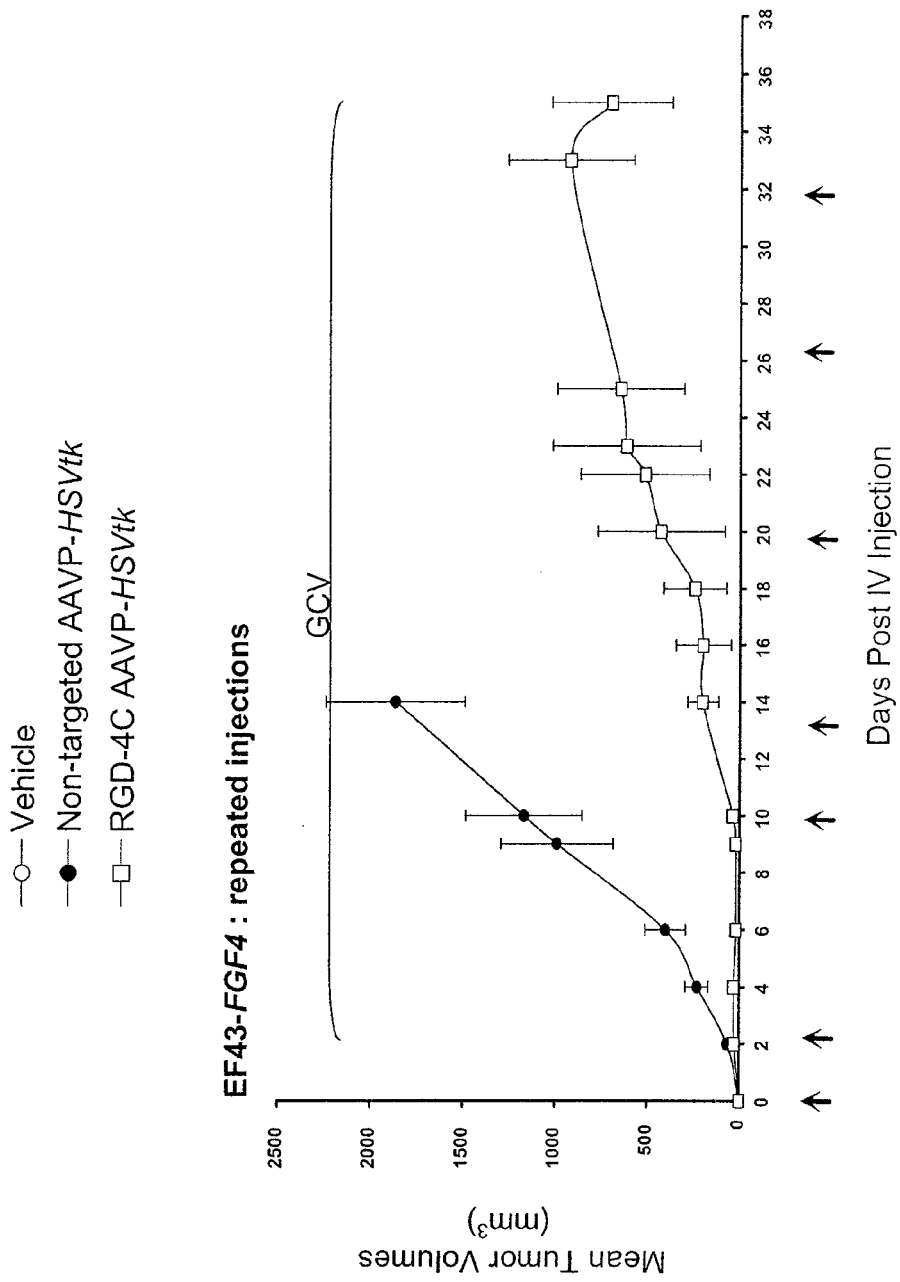
Figure 5G:
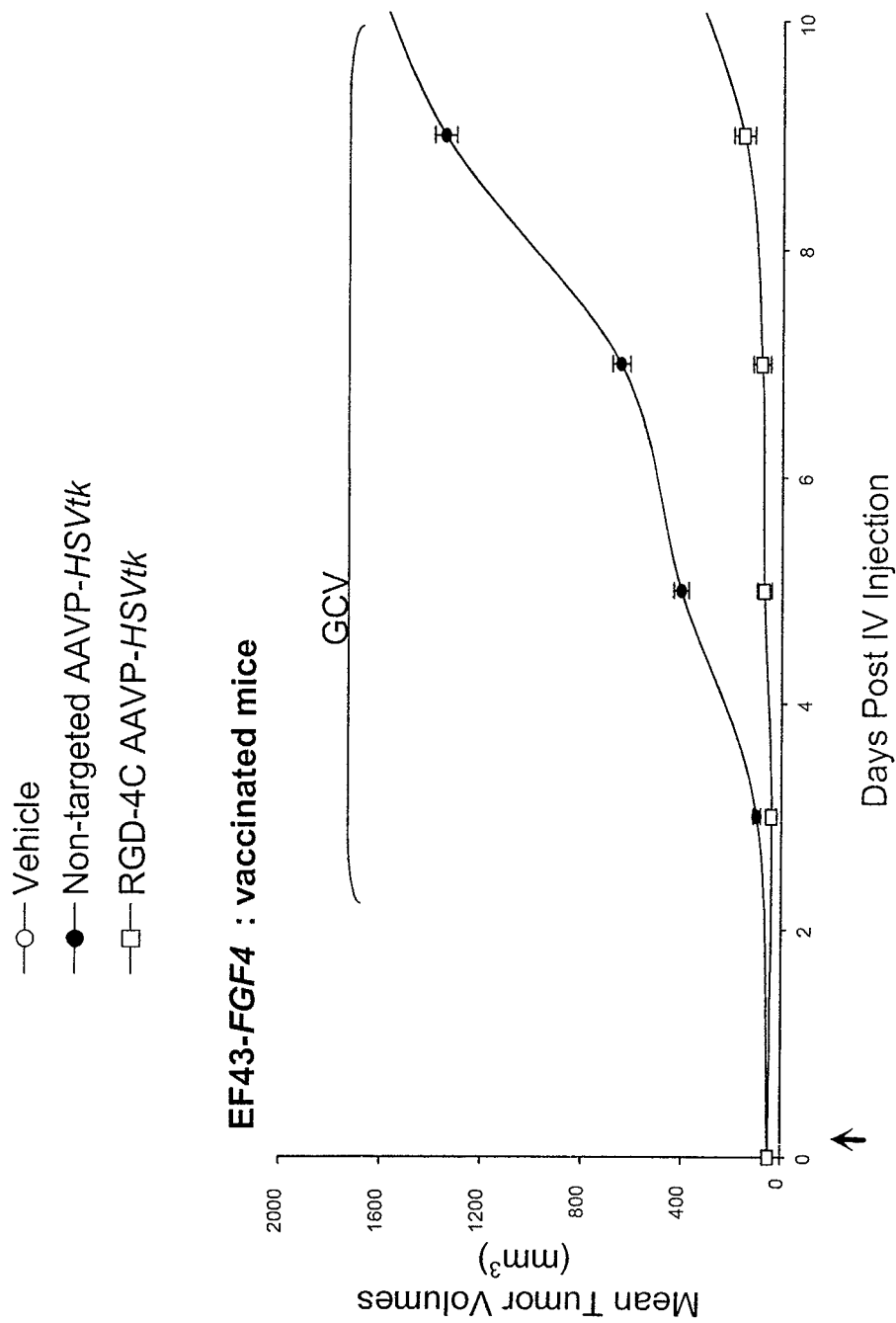
Figure 6A:
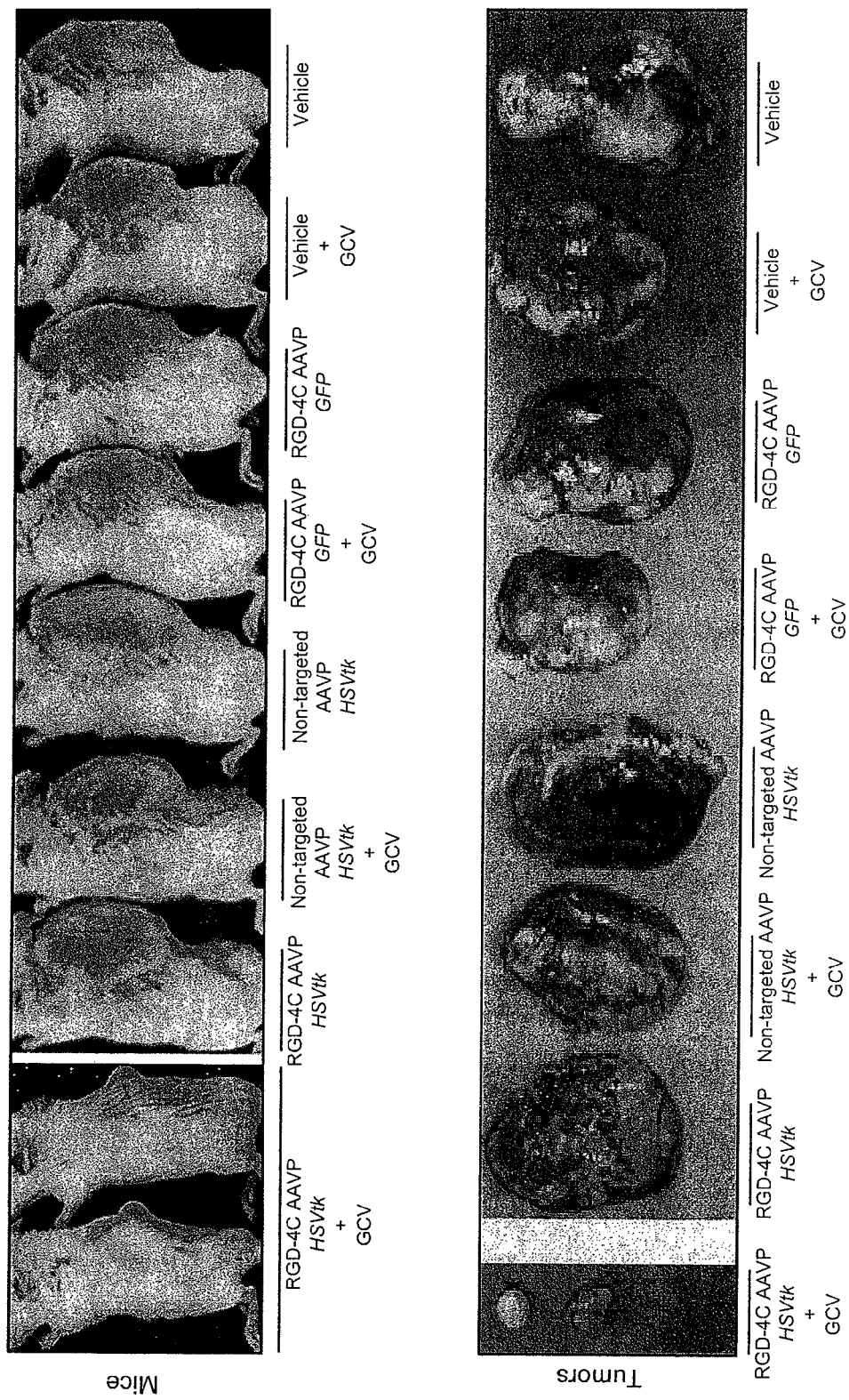
FIGS. 6A-6B FIG. 6A is an image of tumor-bearing mice (upper panel) and corresponding surgically removed tumors (lower panel) from all the experimental groups of therapy (EF43-FGF4 mammary tumors in BALB/c immunocompetent mice).
Figure 10:
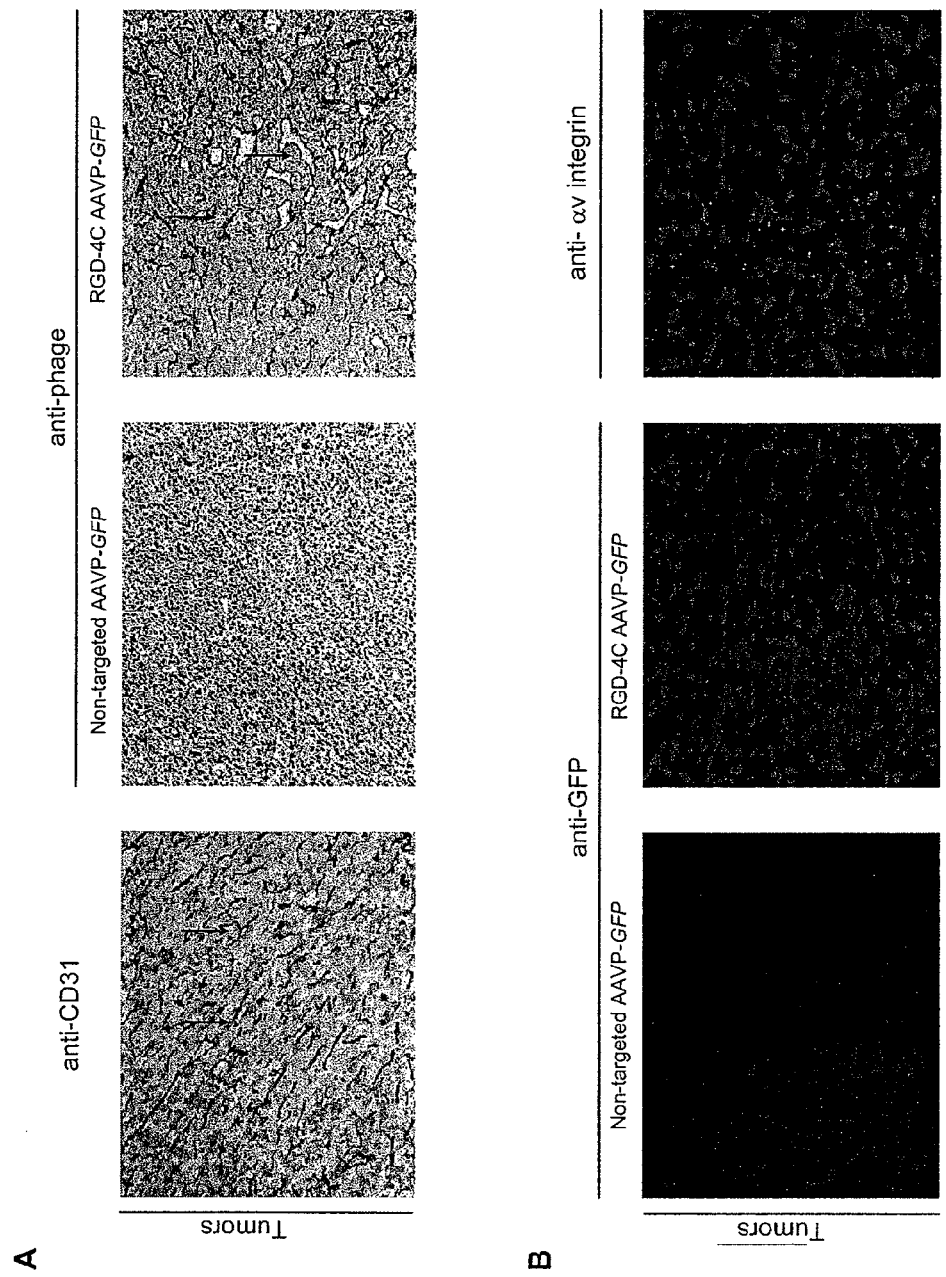
FIGS. 10A-10B FIG. 10A is an image of immunohistochemical staining against AAVP after intravenous administration of RGD-4C AAVP (right panel) or non-targeted AAVP (middle panel) into immunocompetent BALB/c mice bearing EF43-FGF4 tumors. Constructs were allowed to circulate for 5 min, followed by perfusion and tissue recovery as described. A polyclonal antibody against phage was used for staining Left panel shows tumor blood vessel staining by using an anti-CD31 antibody. Arrows point to tumor blood vessels.

In order to evaluate efficacy horizontally in other preclinical models, we assembled a panel of tumor cell lines from different species and histological origins and generated tumors in immunosuppressed or immunocompetent mice. Cohorts of Kaposi sarcoma (KS 1767)-derived tumor-bearing mice received systemically a single intravenous dose of either the RGD-4C AAVP-HSVtk or non-targeted AAVP-HSVtk (control), followed by GCV treatment in all groups. Marked tumor growth suppression was observed in tumor-bearing mice receiving RGD-4C AAVP-HSVtk, as compared to mice treated with vehicle or mice that received non-targeted AAVP (FIG. 5A). Similar tumor growth suppressive effects were observed in UC3-derived bladder carcinomas (FIG. 5B) and DU145-derived prostate carcinomas (FIG. 5C) in nude mice, even if larger tumor xenografts were treated (FIG. 5D) and consistent with the imaging results presented (FIG. 4). To rule out the possibility that the observed anti-tumor effects were either species-specific or xenograft-specific, we sought to analyze the efficacy of the RGD-4C AAVP-HSVtk on a standard mouse tumor model. We chose an isogenic tumor in which EF43-FGF4 mouse mammary cells are administered subcutaneously to induce rapid growth of highly vascularized tumors in immunocompetent mice (Hajitou et al., 2001). First, we show ligand-directed homing of RGD-4C AAVP to EF43 FGF4-derived tumors by anti-phage immunostaining (FIG. 10). Either RGD-4C AAVP-GFP or non-targeted AAVP-GFP was administered intravenously to mice bearing isogenic mammary tumors for a 3-5 min circulation time. Unlike the non-targeted AAVP-GFP, RGD-4C AAVP GFP produced a strong anti-phage staining in tumors (FIG. 10A). Next, we performed immunofluorescence with an anti-GFP antibody at seven days after intravenous administration to reveal strong GFP expression in the tumors in mice that received RGD-4C AAVP-GFP; in contrast, no GFP staining was detected in tumors from mice that received non-targeted AAVPGFP; consistently, an anti-αv integrin antibody detected strong expression in EF43-FGF4 tumors (FIG. 10B). Again, a single systemic dose of RGD-4C AAVP-HSVtk followed by GCV markedly inhibited the growth of EF43-FGF-4 tumors (FIGS. 5E-G and FIG. 6). Moreover, when tumors grew back after termination of therapy, repeated administrations of RGD-4C AAVP-HSVtk again inhibited EF43-FGF4 tumor growth and improved survival of tumor bearing mice (FIG. 5F). Phage-based particles are known to be immunogenic but this feature can be modulated through targeting itself (Trepel et al., 2001). In fact, RGD-4C AAVP-HSVtkplus GCV remained surprisingly effective on phage-vaccinated immunocompetent mice despite very high titers of circulating anti-phage IgG (FIG. 5G). In selective experiments, a comprehensive panel of negative experimental controls including vehicle alone, vehicle plus GCV, non-targeted AAVP, non-targeted AAVP plus GCV, targeted RGD-4C AAVP, targeted RGD-4C AAVP-GFP, and targeted RGD-4C AAVP-GFP plus GCV (mock transduction) were used (FIG. 6A).

Figure 6B:
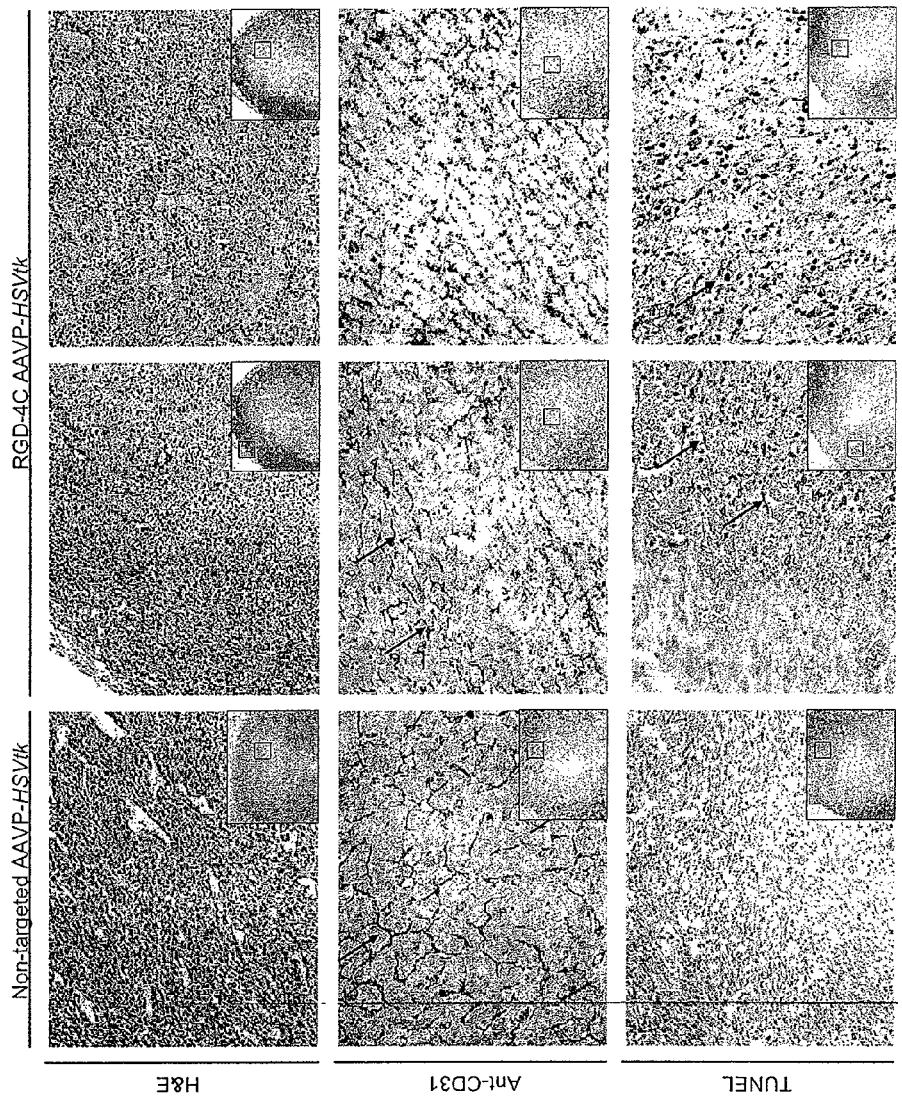
Figure 11:
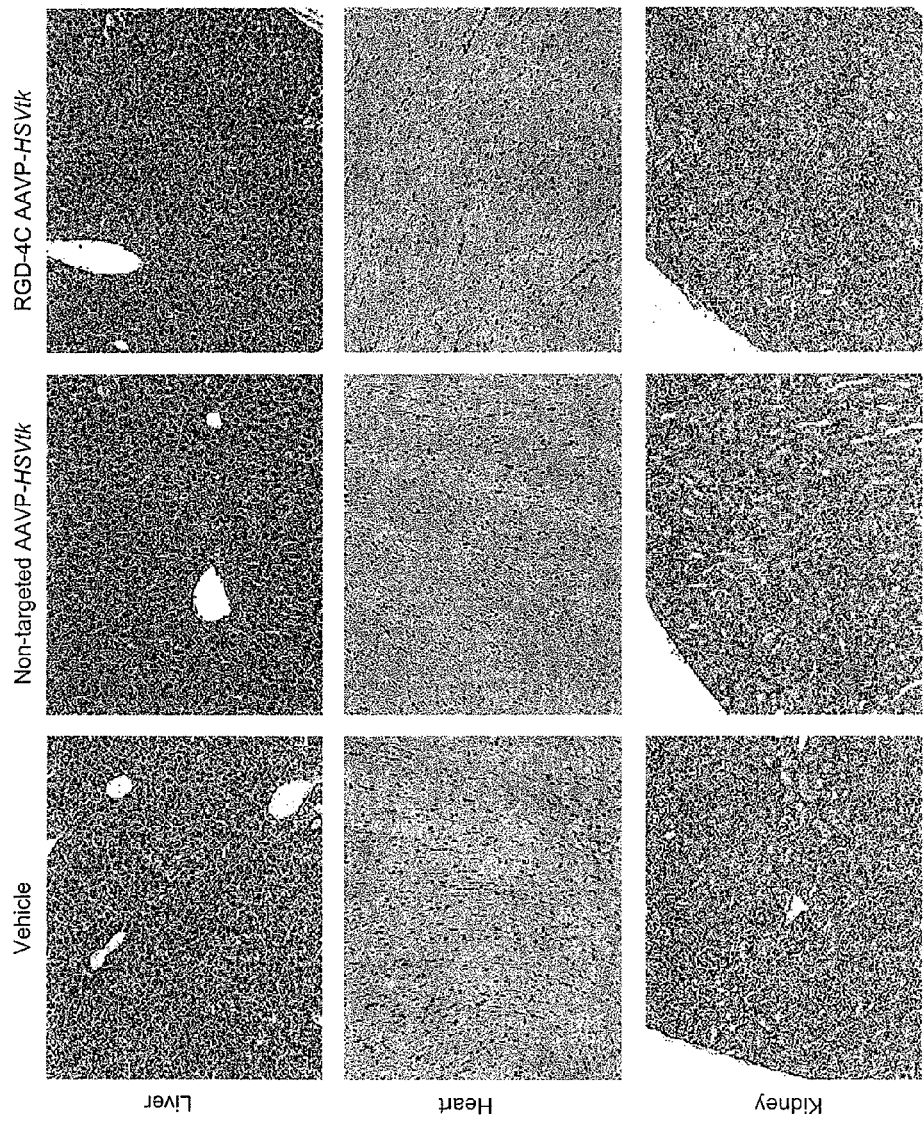
FIG. 11 FIG. 11 shows images of histological analysis of control organs liver, heart, and kidney from mice treated with non-targeted AAVP-HSVtk, RGD-4C AAVP-HSVtk vectors, or vehicle alone plus GCV maintenance are shown. No histological signs of toxicity were detected in these organs by H&E staining.

To check for post-treatment effects, the inventors obtained detailed histopathological analysis of EF43 FGF4 tumors recovered seven days after therapy. Extensive tumor destruction caused by the single systemic dose of RGD-4C AAVP-HSVtk plus GCV was noted. Specifically, hematoxylin and eosin (H&E) staining revealed uniform destruction of the central area of the tumor and only a small viable outer rim; in contrast, non-targeted AAVP-HSVtk had no such effect (FIG. 6B). Staining with an anti-CD31 antibody confirmed both disrupted tumor blood vessels within the tumor central region and preserved vasculature towards the outer rim, whereas no damage was observed in the tumors treated with non-targeted AAVP-HSVtk (FIG. 6B). The inventors also evaluated the tumors for terminal deoxynucleotidyl transferase-mediated dUTP biotin nick end-labeling (TUNEL) staining, which marks apoptotic cells, because the HSVtk/GCV strategy is associated with apoptotic death of cells (Hamel et al., 1996). In tumors treated with RGD-4C AAVP-HSVtk and GCV, TUNEL staining detected apoptosis in the tumor central region but not within the outer rim while no apoptosis was observed in tumors from mice that received non-targeted AAVP-HSVtk chimera (FIG. 6B). Control organs removed from tumor-bearing mice treated by the same experimental protocol revealed no histopathologic abnormalities (FIG. 11). Together, these results show that a single systemic dose of RGD-4C AAVP-HSVtk plus GCV maintenance can suppress tumor growth.

The relative contribution of targeting each tumor compartment (i.e., tumor cells versus tumor vascular endothelium and/or stroma) will depend on the ligand-receptor system and on the model(s) used. For instance, the expression of the membrane target (i.e., αv integrins) in tumor cells will vary from low (EF43 FGF4) to strong (KS1767). Moreover, aside from the specific optimal dose for transduction of each model (and application) used, there is also an optimal time to examine transgene expression. In other words, the stoichiometry of reporter gene expression depends not only from levels and patterns of reporter expression in individual cells, but also from the relative number of proliferating transgene-expressing cells versus dying transgene-expressing cells. Thus, while the inventors used fixed parameters for these examples, further determination of targeted AAVP optimal doses and time-frames on a case-by-case basis still apply.

The inventors contemplate that a broad range of currently intractable biological questions well beyond molecular oncology can be addressed using targeted AAVP, especially in combination with different pre-clinical and clinical molecular-genetic imaging settings. For example, the systemic ligand-directed delivery of constructs with tissue and/or disease-specific promoters (instead of the CMV promoter) to target sites will allow monitoring expression of their corresponding native genes in vivo; such promoter-driven transcription of reporter activity will allow the study of cell trafficking and engraftment. Several non-invasive imaging applications can be employed such as experimental monitoring of substrate-specific degradation, protein-protein interactions and other molecular events via reporter transactivation, complementation, or reconstitution strategies (Luker et al., 2004; De and Gambhir, 2005; Gross and Piwnica-Worms 2005b) in cells and in whole animals. The inventors have recently described networks of gold nanoparticles and bacteriophage as biological sensors and cell targeting agents (Souza et al., 2006), such technology can be combined with ligand-directed AAVP to further improve molecular-genetic imaging. On another note, AAVP itself may provide suitable reagents to study the mechanistic role of ITR structures in transgene persistence and chromosomal integration since (in contrast to AAV vectors) phage-based constructs with no ITRs can serve as negative experimental controls. Thus, many other systemic targeting and molecular imaging applications in tandem is possible in a relatively short timeframe with this novel platform and its derived tools.

Example 2

Use of AAVP to Target TNF-α to Tumor Vasculature

A. Methods

Cell Culture.

Human umbilical vein endothelial cells (HUVEC) were obtained from Cambrex (Walkersville, Md.) and cultured in Endothelial Cell Growth Medium-2 as described previously (Tandle et al., 2005). All experiments were conducted with HUVEC in passage 3-5. M21 human melanoma cells were grown in RPMI 1640 medium containing 10% serum, 2 mM glutamine, 100 u/ml penicillin, 100 µg/ml streptomycin, 100 µg/ml gentamicin and fungizone. Pmel cells were grown in DMEM medium containing 10% serum, 2 mM glutamine, 100 u/ml penicillin, 100 µg/ml streptomycin, 100 µg/ml gentamicin and fungizone.

Construction of a Targeted AAVP Expressing TNF-α/EMAP-II.

The general design and construction of the AAVP backbone is described in Hajitou et al. (2006). An AAVP construct expressing TNF-α was created in two steps. First, a 880 bp NotI/HindIII fragment from pG1SiTNF was digested and ligated into a pAAV-eGFP/NotI/HindIII vector replacing GFP gene sequences (Hwu et al., 1993). In the second step, fMCS/RGDMCS and AAV-TNF were digested by PvuII. Then AAV-TNF-α with inverted terminal repeats (ITRs) were religated into the fMCS-/RGDMCS PvuII site to obtain an AAVP vector. Thus, pfdTNF-α is a non-targeted vector, whereas pRGDTNF is a targeted vector with binding affinity to cell surface αv integrin receptors.

An AAVP construct expressing EMAP-II was created in three steps. The pET-20b plasmid, expressing mature EMAP-II was a generous gift from Paul Schimmel at The Scripps Research Institute, La Jolla, Calif. In the first step, EMAP-II sequences were amplified from pET-20bEMAP-II, using 3 primers to incorporate restriction enzyme sites and the secretable signal sequence in the PCR product. Primer 1 is a 132 bp forward primer with NotI restriction enzyme site at the 5' end followed by a signal sequence (designed from pSecTag2 vector, Invitrogen, Carlsbad, Calif.) for extracellular secretion of gene product and EMAP-II sequences. Primer 2 is a shorter version of primer 1 to facilitate amplification of the PCR product. Primer 3 is a reverse primer with a HindIII restriction enzyme site at 3' end. The PCR amplification generated a 667 bp product with NotI and HindIII enzyme sites and signal sequence. In the second step, the EMAP-II PCR product was cloned into the pCRII-TOPO cloning vector (Invitrogen, Carlsbad, Calif.). The resultant clones were sequenced, and then the 667 bp NotI/HindIII fragment was ligated into a pAAV-eGFP/NotI/HindIII vector as explained earlier. In the third step, fMCS/RGDMCS and AAV-EMAP-II were digested by PvuII and ligated to obtain an AAVP vector. Thus, pfdEMAP-II is a non-targeted vector, whereas pRGDEMAP-II is a targeted vector with binding affinity to cell surface αv integrin receptors. Primer 1: 5' ATTTGCGGCCGCTTTAC-CACCATGGAGACAGACACACTCCTGCTATGG-GTACTGCT GCTCTGGGTTCCAGGTTCCACTGGT-GACGCGGCCCAGCCGGCCAGGCGCGCCGTAAT GTCTAAGCCAATAGATGTT 3' (SEQ ID NO:4); Primer 2: 5'ATTTGCGGCCGCTTTACCACCATGG 3' (SEQ ID NO:5); Primer 3: 5' CCCAAGCTTGGGTTATTTGATTC-CACTGTTGC 3' (SEQ ID NO:6).

AAVP Particle Purification.

To obtain non-targeted and targeted AAVP particles, DNA was electroporated into MC1061 E. coli. Cells and virus particles were purified from the culture supernatant. Large scale AAVP particles were purified from permissive k91Kan cells. In order to determine the number of bacterial transducing units (TU), k91 cells were infected with serial dilutions of phage particles and plated on Luria-Bertani agar plates containing tetracycline and kanamycin TU was then determined by counting the number of bacterial colonies.

In Vitro Phage Internalization Assay.

M21 cells were grown overnight in 6-well tissue culture plates. To study vector internalization, cells were washed with the media and then infected with viral particles at 37° C. for 3 hrs. After incubation, plates were placed on ice for 5 min in order to stop viral internalization. Unbound particles were removed by extensive washing of cells in Hank's balanced salt solution (HBSS). Extracellular viral particles were inactivated by treatment with Subtilisin (3 mg/ml subtilisin, 20 mM Tris pH 7.5, 2 mM EDTA pH 8.0 in HBSS with no calcium and no magnesium) for 1 hr on ice (Ivanenkov et al., 1999). Then, cells were detached with gentle pipetting and subtilisin was inactivated with 2 mM EDTA on ice for 15 min. Cells were lysed by using lysis buffer (10 mM Tris pH 7.5, 2 mM EDTA pH 8.0 and 2% sodium orthovanidate) to release the internalized AAVP particles. The internalized AAVP concentration was then determined as TU as described above.

Immunofluorescence (IF) Assay.

IF was used to observe internalized viral particles in M21 cells. Briefly, cells grown on 8-well Lab-Tek chamber glass slides (Nunc, Rochester, N.Y.) were infected with AAVP particles by using DMEM containing 10% serum at 37° C. for 16 hrs. After infection, cells were washed with PBS, chambers were removed and cells were fixed in 3.7% formaldehyde for 10 min. Cells were permeabilized by 0.1% saponin (Sigma, St. Louis, Mo.) in PBS, and blocked with blocking buffer (PBS containing 1% BSA, 0.025% sodium azide, and 0.1% saponin) for 15 min. After washing with permeabilization buffer, cells were incubated with a mouse anti-bacteriophage antibody for 1 hr, followed by a FITC-conjugated anti-mouse IgG antibody for 1 hr. Gaskets were detached and cells were mounted using Antifade (MP Biomedicals, Solon, Ohio) and examined under a Zeiss Axiovert fluorescent microscope.

Gene Expression by Phage.

M21 cells were infected with AAVP particles as in the internalization assay. The medium was replaced at 48 hrs. At day 4 and day 12, the culture supernatant was collected to measure secretable cytokine levels by ELISA (Invitrogen, Carlsbad, Calif.).

Tissue Factor (TF) Assay.

To examine whether secreted TNF-α/EMAP-II is functional, we examined its ability to induce TF synthesis in endothelial cells ECs. Briefly, $2 \times 10^5$ HUVEC were plated on 6-well tissue culture plates per well. On the following day, cells were treated with M21 culture supernatants for 6 hrs in serum-free RPMI media. The cells were washed with PBS and incubated with 25 mM Tris pH 7.5 for 10 min at room temperature. The culture plates were then incubated at −80° C. for 2 hrs. The total cell lysates were prepared in tissue factor assay buffer (20 mM Tris pH 7.5, 150 mM NaCl and 0.1% BSA). Lysates were cleared by centrifugation at 13,000 rpm for 10 min. The 100 µl lysate was analyzed for presence of tissue factor by measuring the time required for coagulation of Factor VIII-deficient plasma (Geroge King Biomedical Inc, Overland Park, Kans.) in the presence of $CaCl_2$ (Sigma, St. Louis, Mo.) in an Amelung KC 4A Micro Coagulation Analyzer (Sigma, St. Louis, Mo.). The time required to coagulate Factor VIII-deficient plasma was converted to tissue factor units by using a standard calibration curve plotted with known tissue factor concentrations.

In Vivo AAVP Delivery and Detection by Immunofluorescence Staining.

All animal experiments were conducted according to protocols approved by the NIH Animal Care and Use Committee. Female athymic nude mice were obtained from the Jackson Laboratories and housed in the National Cancer Institutes, animal facility. Human melanoma cells ($4 \times 10^6$) were inoculated subcutaneously into the right flank of nude mice. Tumor volume ($mm^3$) was measured in three dimensions and calculated as length×width×height×0.52. When tumor volumes reached around 100-150 $mm^3$, $1 \times 10^{11}$ AAVP particles were injected intravenously (via tail vein). Animals were euthanized at various time intervals. Resected tumor tissues and control tissues (kidney and liver) were frozen for further analysis.

To detect the presence of AAVP, 5 μM thick frozen sections were stained using dual IF staining Briefly, sections were fixed in 4% paraformaldehyde for 5 min, followed by 2 washes in PBS for 10 min. Permeabilization was done in PBS containing 1% Triton-X-100 for 10 min. Sections were incubated with Image-iT FX signal enhancer for 30 min at room temperature (RT), followed by three washes in PBS containing 1% Triton-X-100. Non-specific binding was blocked using 5% goat serum for 30 min at RT. The primary antibodies were applied overnight at 4° C.: 1:2000 dilution of anti-fd bacteriophage antibody (Sigma, St. Louis, Mo.) and 1:50 dilution of anti mouse CD31 (BD Biosciences, San Jose, Calif.). Sections were washed thrice in PBS containing 1% Triton-X-100 for 10 min, then incubated with the secondary antibodies (Invitrogen, Carlsbad, Calif.): 1:400 dilutions each of goat anti-rabbit Alexa Fluor 594 and goat anti-rat Alexa Fluor 488 for 30 min in the dark. Sections were washed thrice in PBS containing 1% Triton-X-100 for 10 min and once with PBS, followed by mounting in Vectashield mounting medium with DAPI (Vector Labs, Burlingame, Calif.).

TNF-α Expression In-Vivo.

To detect TNF-α protein expression, total cell lysate was prepared from 5 μM frozen tissue sections using lysis buffer (50 mM Tris pH 7.4, 140 mM NaCl, 0.1% SDS, 1% NP40 and 0.5% sodium deoxycholate) containing protease inhibitor cocktail (Roche, Branchburg, N.J.). The lysates were cleared by centrifugation at 13,000 rpm for 10 min. The amount of protein was quantitated using protein assay reagent from BioRAD. The amount of lysate equivalent to 50 μg of total protein was assayed for human TNF-α by ELISA (Invitrogen, Carlsbad, Calif.).

To examine localization of TNF-α expression, 5 μM frozen tissues were stained as follows. Briefly, sections were fixed in PBS containing 4% paraformaldehyde for 20 min, washed with PBS three times for 5 min each and non-specific binding was blocked with 5% goat serum for 20 min. Sections were incubated either with 1:200 diluted anti-fd antibody (Sigma, St. Louis, Mo.) or 1:100 diluted TNF-α antibody (Novus Biologicals, Littleton, Colo.), or rat anti-mouse CD31 (BD Biosciences, San Diego, Calif.) for 1 hr., followed by three washes of 5 min each in washing buffer (PBS containing 50 mM Tris pH 7.6 and 0.02% Tween-20). Endogenous peroxidase was blocked with 3% hydrogen peroxide for 5 min followed by washing and incubation with 1:200 dilution of the secondary antimouse-HRP or biotinylated donkey anti-rat antibody for 30 min. Sections were developed with diaminobenzidine tetrahydrochloride substrate (Dako, Carpinteria, Calif.) for 5 min and counterstained with hematoxylin for 30 sec, rinsed in tap water, dehydrated, cleared and mounted.

Apoptosis Assay.

Apoptosis was detected using the In Situ Apoptosis Detection kit, TACS TdT (R&D Systems, Minneapolis, Minn.), according to the manufacture's recommendations.

Tumor Growth Analysis.

Human melanoma cells ($3 \times 10^6$) were inoculated subcutaneously into the right flank of nude mice. When tumor volumes reached approximately 100 $mm^3$, $1 \times 10^{11}$ AAVP particles were administered via tail vein. AAVP particle administration was repeated once more after 7 days. The tumor bearing mice were followed thereafter by measuring tumor volumes every third day in a blinded fashion.

Statistical Analysis.

Groups were compared by using Analysis of Variance (ANOVA) and Tukey comparison post test (GraphPad Instat Software, Inc., San Diego, Calif.). P values <0.05 were considered statistically significant.

B. Results

AAVP Particles are Internalized by Mammalian Cells.

Previous studies have shown that phage particles can be internalized by integrin-mediated receptor internalization (Hajitou et al., 2006). M21 cells express αvβ3 receptors on their cell surface (data not shown). In order to examine, if M21 cells can internalize AAVP particles, we infected cells with AAVP particles and then counted internalized phage. After infection, the entire extracellular virus was inactivated by subtilisin treatment, cells were lysed and internalized phage was recovered in the lysate. The internalized AAVP concentration was measured as TU (Table 6). There was minimal AAVP internalization by M21 cells infected with either non-targeted null (fd) or TNF-α expressing non-targeted virus (fdTNF-α) in contrast to cells infected with targeted null (RGD) or targeted TNF-α expressing AAVP (RGDTNF-α).

TABLE 6

Phage Internalization Assay

| Agent | pfu/μl | Total number of phage particles ($10^2$) |
|---|---|---|
| PBS | 0 | 0 |
| fd | $3 \times 10^2$ | 1500 |
| RGD | $140 \times 10^2$ | 70,000 |
| fdTNF-α | $6 \times 10^2$ | 3000 |
| RGDTNF-α | $215 \times 10^2$ | 107,500 |

Figures 12A, 12B, 12C:
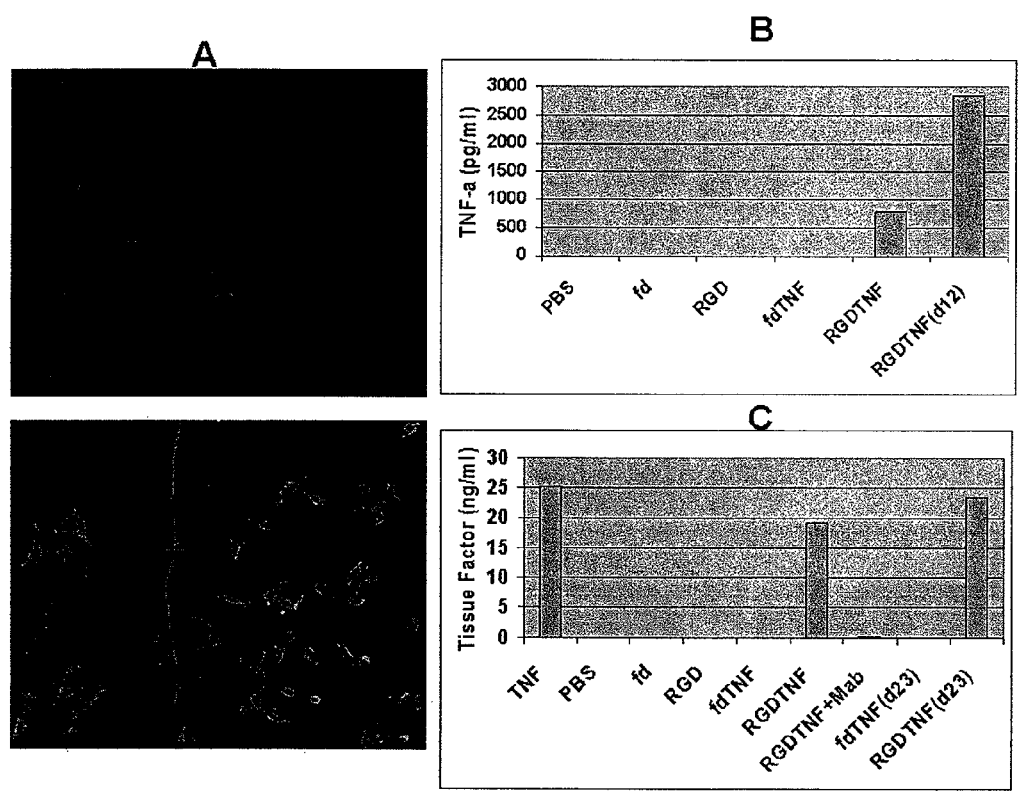
FIGS. 12A-12C Mammalian cells infected with RGD-targeted AAVP expresses a functional gene product.

IF was used to visualize the localization of internalized AAVP particles inside M21 cells. Cells infected with non-targeted TNF-α expressing AAVP (fdTNF-α) did not show phage localization (FIG. 12A, upper panel). In contrast, cells infected with targeted AAVP expressing TNF-α (RGDTNF-α) showed enhanced localization inside M21 cells (FIG. 12A, lower panel).

AAVP Mediated Gene Expression.

After determining that targeted AAVP can infect and localize inside the mammalian cells, we investigated whether virus infection could lead to expression of the gene product. M21 cells were infected with AAVP expressing TNF-α, in duplicates, and production of the TNF-α gene product was measured by ELISA. The gene product is secretable and can be detected in the culture supernatants (FIG. 12B). The supernatant tested after 5 days of infection showed TNF-α levels of 800 pg/ml. The gene product tested at day 12 was higher than day 4. The diluent control (PBS), non-targeted empty (fd), non-targeted virus expressing TNF-α (fdTNF-α) and targeted null AAVP (RGD) had no detectable levels of TNF-α secretion (FIG. 12B).

To examine whether secreted TNF-α by AAVP infected M21 cells was functional; we tested its ability to induce tissue factor (TF) synthesis in ECs. The secreted TNF-α was capable of inducing TF expression in ECs (FIG. 12C). Recombinant TNF-α was used as a positive control. The TF induction could be blocked by incubating culture supernatant with a TNF-α monoclonal antibody. The culture supernatant analyzed 23 days post-infection also showed functional TNF-α secretion (FIG. 12C). Thus, a single infection with AAVP resulted in the production of functional gene product up to 23 days following infection.

In Vivo Tumor Targeting by AAVP.

We observed AAVP infection of mammalian cells and functional expression of the TNF-α gene product in vitro. In order to evaluate in vivo targeting of AAVP, virus was injected systemically via tail vein in tumor-bearing nude mice.

Figures 13A, 13B, 13C, 13D, 13E, 13F, 13G, 13H:
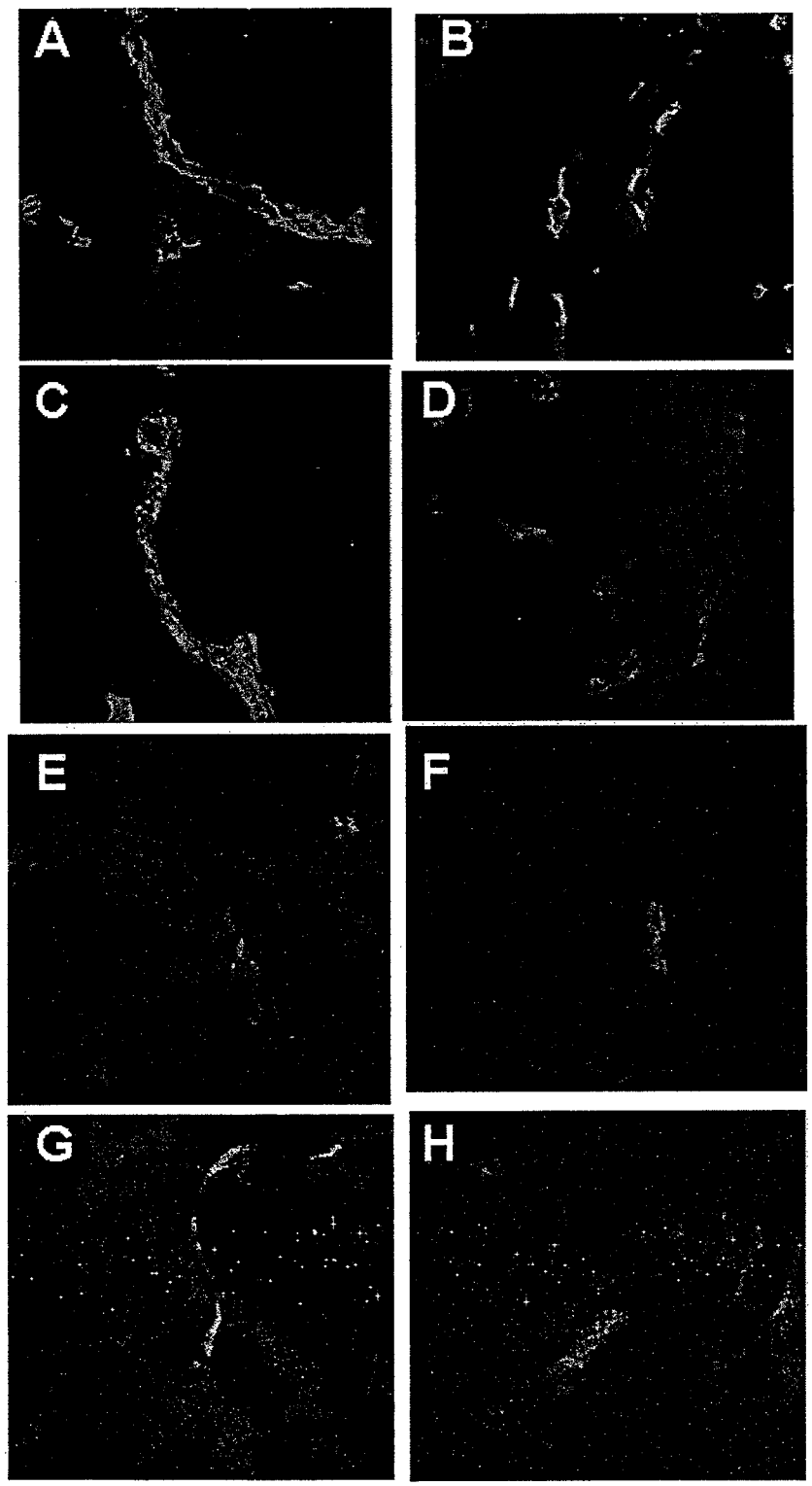

Mice injected with either a diluent (PBS) or RGDTNF-α AAVP, were euthanized at 15 min, 1 day, 2 days, 3 days, 4 days, 8 days and 10 days after injection. The frozen sections from tumor tissues were analyzed for the presence of viral particles by dual IF staining. As shown in FIG. 13, AAVP particles stain red (Alexa Flour 594), blood vessels green (Alexa Flour 488) and DAPI shows nuclear staining None of the animals injected with PBS showed presence of AAVP at any time point. A representative tumor section from an animal injected with PBS for 15 min is shown (FIG. 13A). The animals injected with AAVP expressing RGDTNF-α showed colocalization of virus particles in the blood vessels (FIG. 13B-H). The greatest accumulation of virus particles was detected in animals injected after 15 min (FIG. 13B). The presence of AAVP was detected in all the time points tested, day 1 (FIG. 13C)]], day 2 (FIG. 13D), day 3 (FIG. 13E), day 4 (FIG. 13F), day 8 (FIG. 13G), and day 10 (FIG. 13H). However, we noted a gradual decrease in detectable virus particles over time.

AAVP do not Target Normal Tissues In-Vivo.

In order to examine the specificity of AAVP targeting to tumor blood vessels in vivo, we examined two control tissues from nude mice injected with either PBS or AAVP expressing RGDTNF-α at different time points (FIG. 14 and FIG. 15). The presence of virus was detected using dual IF staining as previously described.

Figures 14A, 14B, 14C, 14D, 14E:
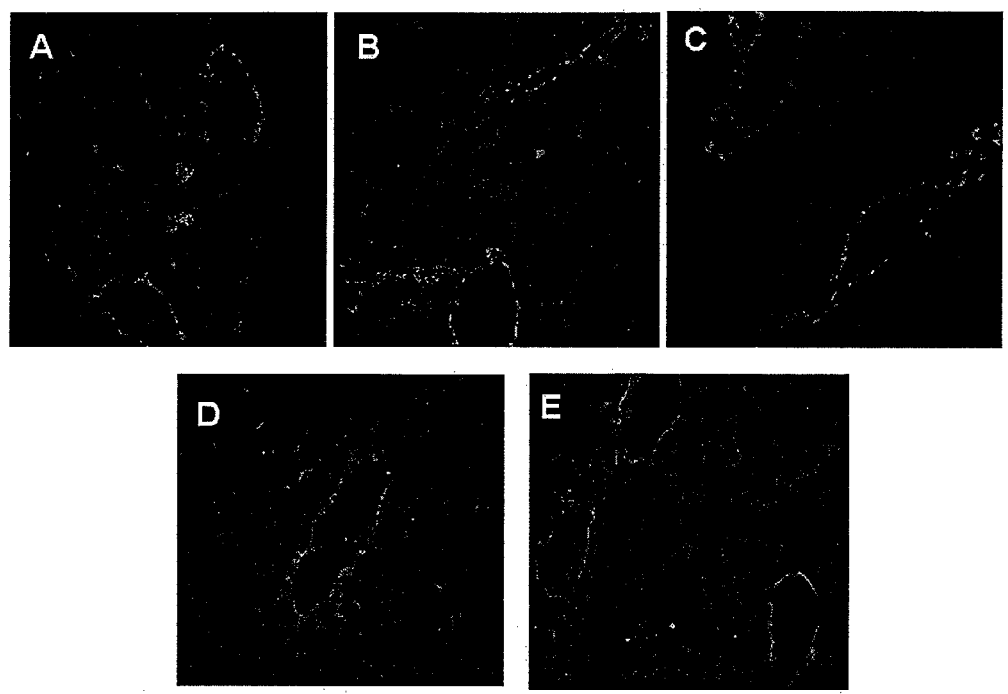
FIGS. 14A-14E AAVP particles were not detected in normal liver tissue. The liver from animals with human melanoma xenografts injected with RGDTNF-α stained with bacteriophage specific antibody and CD31 blood vessel antibody. The detection was done using Alexa Flour 488, Alexa Flour 594 and DAPI to visualize blood vessels, AAVP and cell nuclei respectively (250×). The animals injected with AAVP expressing RGDTNF-α, showed some staining of virus particles at day 1 (FIG. 14A) in the liver tissue. However, the virus staining was reduced to minimal levels by day 2 (FIG. 14B) with no virus staining observed at day 3 (FIG. 14C), day 8 (FIG. 14D) and day 10 (FIG. 14E) time points. All the liver tissues at different time points showed good vessels staining.
Figures 15A, 15B, 15C, 15D, 15E:
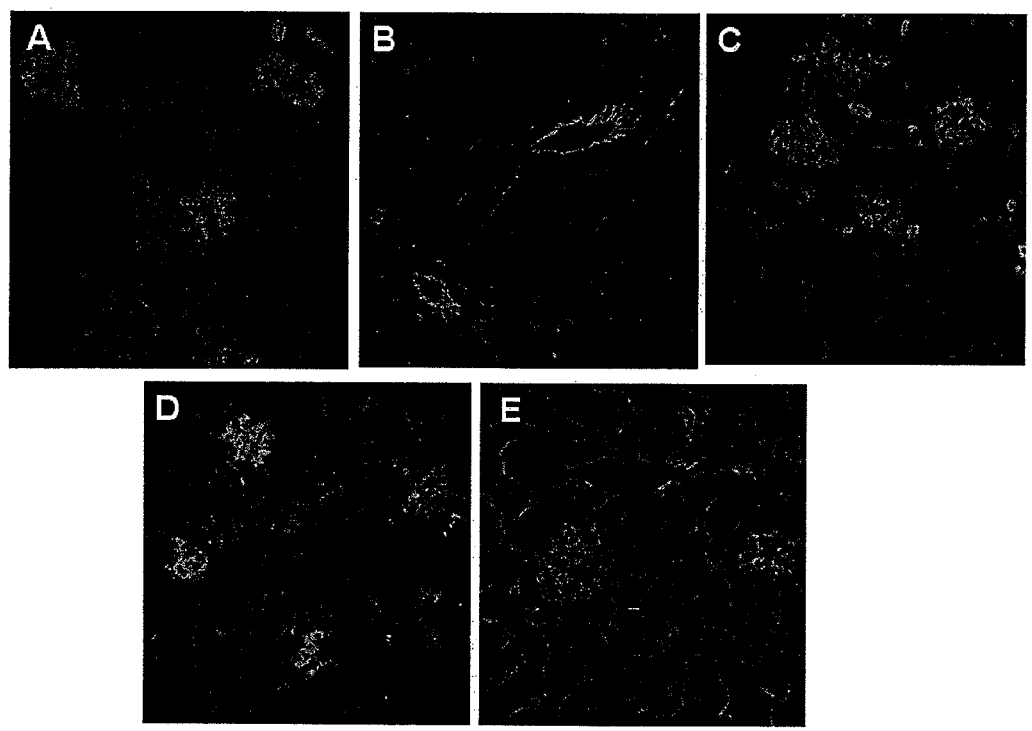
FIGS. 15A-15E AAVP particles were not detected in normal kidney tissue. The kidney from animals with human melanoma xenografts injected with RGDTNF-α was stained with the bacteriophage specific antibody and CD31 blood vessel antibody. The detection was done using Alexa Flour 488, Alexa Flour 594 and DAPI to visualize blood vessels, AAVP and cell nuclei respectively (250×). We did not observe presence of AAVP in kidney in any of the time points tested, day 1 (FIG. 15A), day 2 (FIG. 15B), day 3 (FIG. 15C), day 8 (FIG. 15D) and day 10 (FIG. 15E). Nevertheless, all the kidney tissues at different time points showed good vessels staining.

As shown in FIG. 14, we observed some staining of virus particles at day 1 (FIG. 14A) in the liver tissue. However, the virus staining was reduced to minimal levels by day 2 (FIG. 14B) with no virus staining observed at day 3 (FIG. 14C), day 8 (FIG. 14D) and day 10 (FIG. 14E). FIG. 15 shows kidney sections stained for presence of virus particles. AAVP particles were not detected in kidney in any of the time points tested, day 1 (FIG. 15A), day 2 (FIG. 15B), day 3 (FIG. 15C), day 8 (FIG. 15D) and day 10 (FIG. 15E). Nevertheless, all the kidney tissues at different time points showed good vessels staining.

In Vivo Expression of Functional Gene Product by AAVP.

Figure 16:
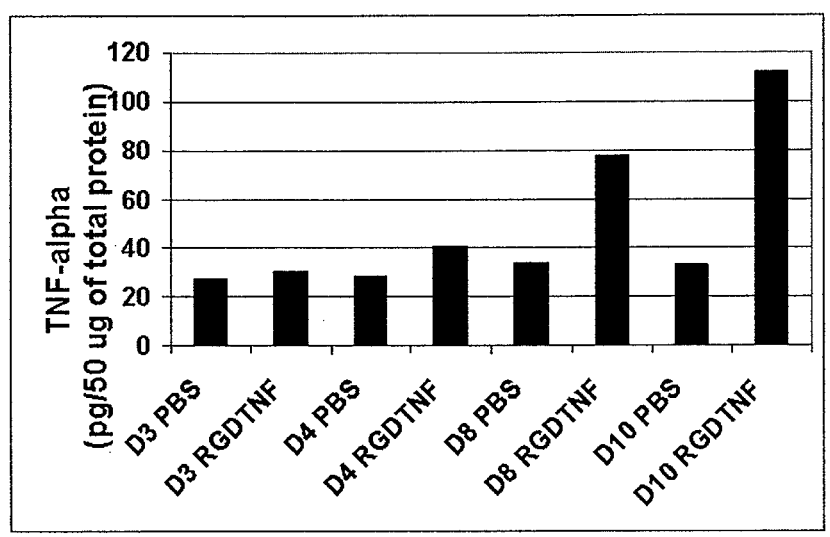
FIG. 16 In vivo, AAVP expresses specific gene product. Frozen sections from animals with human melanoma xenografts injected with either PBS or RGDTNF-α were used to extract total protein. 50 μgs of total protein was used to measure TNF-α protein levels by ELISA in duplicates. Basal levels of endogenous TNF-α expression were observed in all the tissues tested. Animals injected with PBS did not show any increase over the endogenous levels at any time points tested. Mice injected with RGDTNF-α AAVP showed TNF-α expression starting at day 4 and gradually increasing up to day 10.

To examine if the AAVP particles targeted to tumor vasculature can express the gene product, we analyzed, in duplicates, day 3, day 4, day 8 and day 10 tumor tissues for TNF-α protein levels by ELISA (FIG. 16). We observed basal levels of endogenous TNF-α expression in all the tissues tested. Animals injected with PBS did not show any increase over the endogenous levels at any tested time points. Mice injected with RGDTNF-α AAVP showed TNF-α expression starting at day 4 and gradually increasing up to day 10 (FIG. 16).

Figures 17A, 17B:
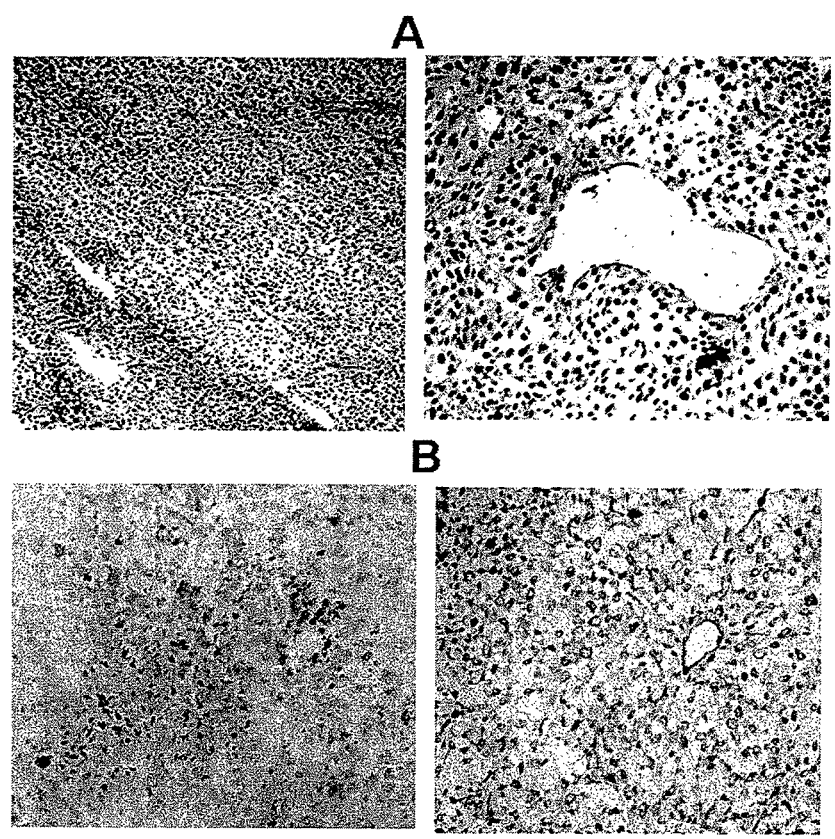
FIGS. 17A-17B AAVP expresses TNF-α in the vasculature and induces apoptosis in vivo.

To determine the cell type where the gene product was being produced, we stained tissue sections using an antibody specific to TNF-α. We observed the presence of TNF-α staining around the blood vessels (FIG. 17A). To see the effect of TNF-α expression we stained tumor sections, for apoptosis. The DNA fragmentation was detected using TACS blue label. The apoptotic cells stain blue (FIG. 17B, left panel). To discriminate apoptotic cells from necrotic cells, the samples were counterstained with nuclear fast red to aid in the morphological verification of apoptosis. We observed blood vessels and surrounding tumor cells undergoing apoptosis. The right panel shows blood vessels stained with a CD31 specific antibody (FIG. 17B, right panel).

Tumor Growth Analysis.

Figures 18A, 18B:
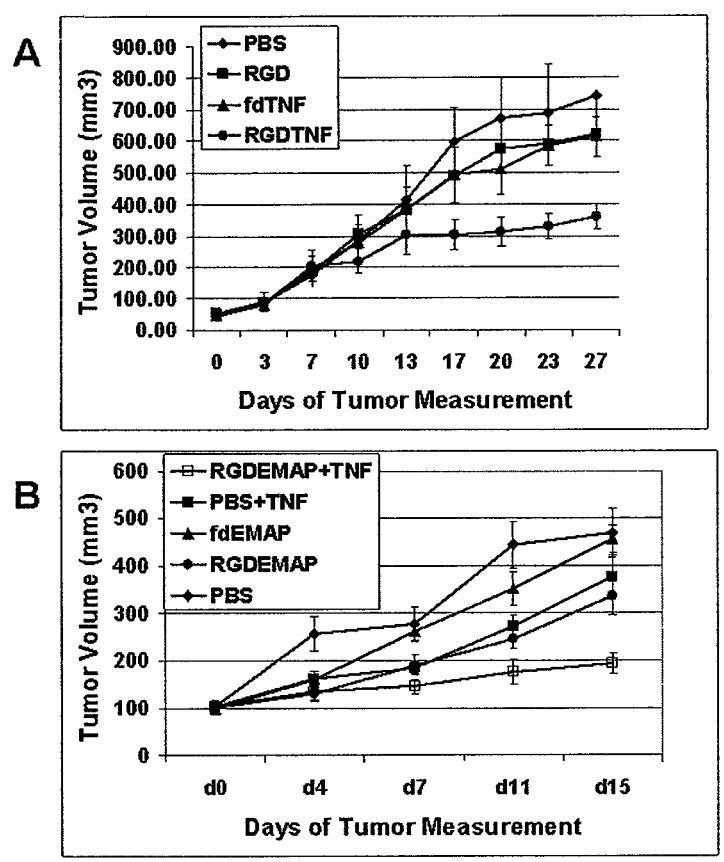
FIGS. 18A-18B Treatment of TNF-α sensitive human melanoma, M21 (FIG. 18A) and TNF-α resistant human melanoma Pmel (FIG. 18B) with AAVP. Nude mice with subcutaneously implanted M21/Pmel tumors were treated with AAVP systemically through tail vein injection and tumor volumes were measured at different time points. The tumor volumes plotted against the different days post treatment.

We analyzed the effect of AAVP on tumor xenografts grown in nude mice in two different tumor models, TNF-α sensitive (M21) and TNF-α resistant (Pmel), to examine treatment efficacy of AAVP expressing TNF-α. Human melanoma M21 tumors, which are sensitive to TNF-α, were grown subcutaneously in nude mice. After tumor development, mice were treated systemically via tail vein injections with various AAVP constructs or PBS. The animals were followed for 27 days. The treatment of the M21 tumors with targeted AAVP expressing TNF-α (RGDTNF-α) showed characteristic central tumor necrosis and tumor shrinkage. On day 27, the final measured time point for the different cohorts, the PBS-treated group had mean tumor volume of 743±383 (±SD) mm$^3$, non-targeted fdTNF group had mean tumor volume of 613±155 (±SD) mm$^3$, null-targeted RGD phage had mean tumor volume of 622±141 (±SD) mm$^3$ and targeted TNFα expressing group had mean tumor volume of 358±98 (±5D) mm$^3$ (p<0.048) (FIG. 18A). The reduction in tumor volume in the RGDTNF-α group was statistically significant starting at day 20.

In a TNF-α-resistant tumor model, human melanoma Pmel tumors were sensitized to the TNF-α effect by pre-treating them with AAVP expressing EMAP-II before administrating TNF-α. In a previous study, we demonstrated that viral vector delivery of EMAP-II can sensitize resistant tumors to the effects of systemically delivered TNF-α. Tumors grown subcutaneously in nude mice were treated systemically with AAVP expressing EMAP-II, followed by systemic treatment with recombinant TNF-α (rTNF-α.). Tumors were followed for 2 weeks after treatment. As shown in the FIG. 18B, mice treated with non-targeted AAVP expressing EMAP-II (fdEMAP) showed similar tumor growth compared to mice treated with PBS alone. Mice treated with either rTNF-α or targeted AAVP expressing EMAP-II (RGDEMAP-II) alone showed very little effect, and were not significantly different than the PBS or fdEMAP-II group. However, mice treated with a combination of the RGD-EMAP-II virus and rTNF-α showed significant reduction in tumor volume (p=0.007).

Example 3

Human Transferrin Peptide Targets the Transferrin/Transferrin Receptor System

Figures 19A, 19B:
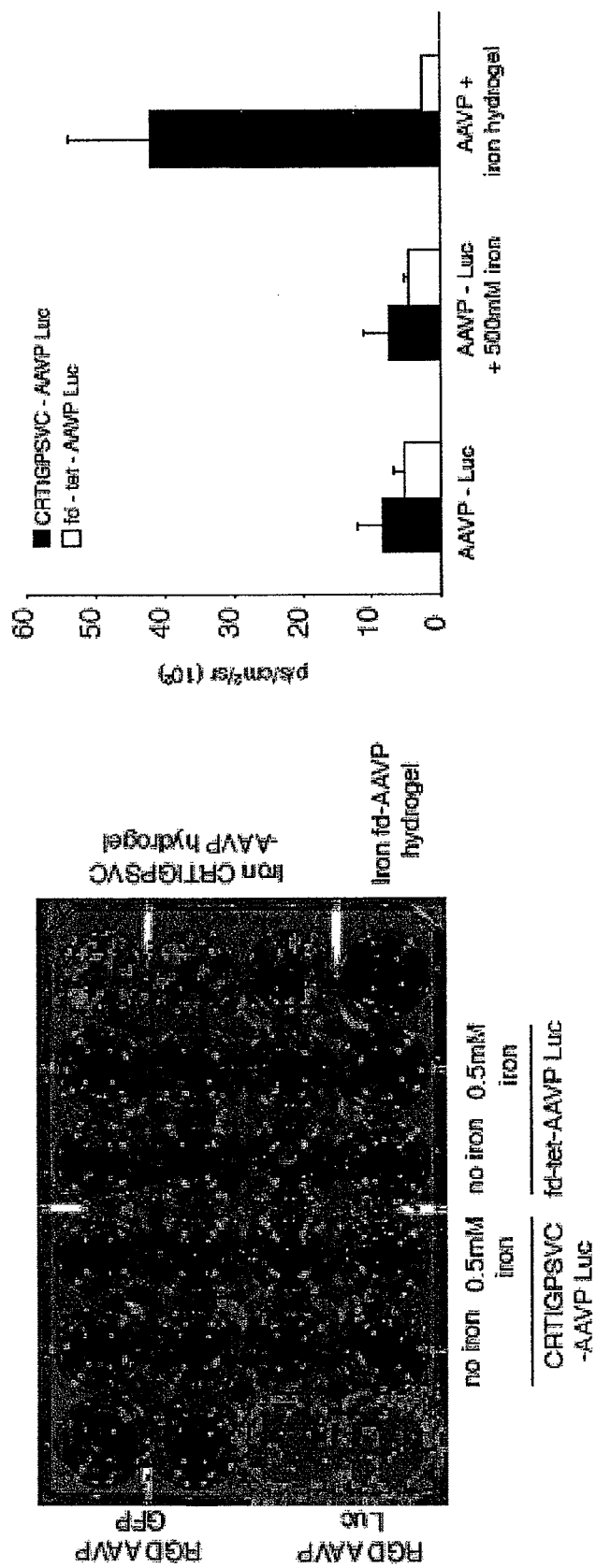
FIGS. 19A-19B Transduction of human glioma cells in culture by CRTIGPSVC (SEQ ID NO:1) AAVP—Luc U87 human-derived glioma cells were seeded onto 24 wells plate at the concentration of 40,000 cells/well and cultured O.N. at 37° C. Next day, cells were incubated with AAVP, according with Nature Method's protocol. RGD-4C AAVP GFP and RGD-4C AAVP Luc were used as positive control for transduction efficiency. The images were taken at day 7. Phage uptake is low but increases dramatically when cells are cultured in Iron AAVP hydrogel (last column of the plate and graphic).

Transduction of human glioma cells in culture by CRTIGPSVC (SEQ ID NO:1) AAVP—Luc U87 human-derived glioma cells were seeded onto 24 wells plate at the concentration of 40,000 cells/well and cultured O.N at 37° C. Next day, cells were incubated with AAVP, according with Nature Method's protocol. RGD-4C AAVP GFP and RGD-4C AAVP Luc were used as positive control for transduction efficiency. The images were taken at day 7. Phage uptake is low but increases dramatically when cells are cultured in Iron AAVP hydrogel (last column of the plate and graphic) (FIGS. 19A-19B). We evaluated the specificity and efficiency of the CRTIGPSVC (SEQ ID NO:1) AAVP—Luc after systemic administration into animals bearing U87 human—derived glioblastoma cells. Luciferase activity was measured after 7 days of phage injection.

REFERENCES

The following references, to the extent that they provide exemplary procedural or other details supplementary to those set forth herein, are specifically incorporated herein by reference.

Alauddin et al., J. Labelled Compds. Radiopharm. 46, 285-289, (2003).
Arap et al., Science 279, 377-380, (1998).
Arap et al., Cancer Cell 6, 275-284, (2004).
Arcone et al., *Nucleic Acids Res.,* 16(8):3195-3207, 1988.
Baichwal and Sugden, *In: Gene Transfer,* Kucherlapati (ed.), NY, Plenum Press, 117-148, 1986. Barbas et al., Phage Display: A Laboratory Manual (New York: Cold Spring Harbor Press), (2001).
Barrow and Soothill, Trends Microbiol. 5, 268-271, (1997).
Blasberg and Tjuvajev, J. Clin. Invest. 111, 1620-1 629, (2003).
Brooks et al., Cell 79, 1157-1 164, (1994).
Chen et al., Chem. Biol. 11, 1081-1091, (2004).
De and Gambhir, FASEB J. 19, 2017-2019, (2005).
Ellerby et al., Nature Med. 5, 1032-1 038, (1999).
Geier et al., Nature 246, 221-223, (1973).
Gelovani and Blasberg, Cancer Cell 3, 327-332, (2003).
Gilliland et al., *Proc. Natl. Acad. Sci. USA,* 77(8):4539-4543, 1980.
Giordano et al., Nature Med. 11, 1249-1253, (2001).
Gossen and Bujard, *Proc. Natl. Acad. Sci. USA,* 89(12):5547-5551, 1992.
Gross and Piwnica-Worms, Cancer Cell 7, 5-15, (2005a).
Gross and Piwnica-Worms, Methods Enzymol. 399, 5 12-530, (2005b).
Hajitou et al., Cancer Res. 61, 3450-3457, (2001).
Hajitou et al., Trends Cardiovasc. Med. In press, (2006).
Hamel et al., Cancer Res. 56, 2697-2702, (1996).
Hara et al., Gene Ther. December; 2(10):784-8, (1995)
Hermonat and Muzyczka, Proc. Nat'l. Acad. Sci. USA 8 1:6466-6470, (1984).
Hood et al., Science 296, 2404-2407, (2002).
Hsiao et al., Dev. Dyn. 220, 323-336, (2001).
Hwu et al., J Immunol 151:4104-15, (1993)
Ivanenkov et al., Targeted delivery of multivalent phage display vectors into mammalian cells. Biochim. Biophys. Acta 1448, 463-472, (1999).
Kageyama et al, *J. Biol. Chem.,* 262(5):2345-2351, 1987.
Kootstra and Verma, Annu. Rev. Pharmacol. Toxicol. 43, 413-439, (2003).
Larocca et al., FASEB J. 13, 727-734, (1999).
Lebkowski et al., Mol. Cell. Biol. 8:3988-3996, (1988).
Lieber et al., J. Virol. 73, 93 14-9324, (1999).
Luker et al., PNAS 10 1, 12288-12293, (2004).
Macejak and Sarnow, *Nature,* 353:90-94, 1991.
Machida, Viral Vectors for Gene Therapy (Totowa, N.J.: Humana Press), (2003).
Marchib et al., Cancer Cell 5, 15 1-162, (2004).
Massoud and Gambhir, Genes Dev. 17, 545-580, (2003).
McCarty et al., Annu Rev. Genet. 38, 819-845, (2004).
Miller et al., Nature Biotechnol. 21, 1040-1046, (2003).
Mizuguchi and Hayakawa, Hum. Gene Ther. 15, 1034-1044, (2004).
Muzyczka, Curr. Top. Microbiol. Immunol. 158:97-129, (1992).
Nakamura et al., Hum. Gene Ther. 13, 613-626, (2002).
Nicolas and Rubenstein, In: Vectors: A survey of molecular cloning vectors and their uses, Rodriguez and Denhardt (Eds.), Stoneham: Butterworth, 493-513, 1988.
Oliviero et al., *EMBO J.,* 6(7):1905-1912, 1987.
Pasqualini et al., Nature Biotechnol. 15, 542-546, (1997).
Pelletier and Sonenberg, *Nature,* 334:320-325, 1988.
Piersanti et al., J. Mol. Med. 82, 467-476, (2004).
Poul and Marks, J. Mol. Biol. 288, 203-21 1, (1999).
Prowse and Baumann, *Mol. Cell. Biol.,* 8(1):42-51, 1988.
Ray et al., Semin. Nucl. Med. 3 1, 3 12-320, (2001).
Remington's Pharmaceutical Sciences, 15th ed., pages 1035-1038 and 1570-1580, Mack Publishing Company, Easton, Pa., 1980.
Ridgeway, In: Vectors: A survey of molecular cloning vectors and their uses, Stoneham: Butterworth, 467-492, 1988.
Ron et al., *Mol Cell Endocrinol.* 21; 74 (3):C97-104, 1990.
Sambrook et al., In: Molecular cloning, Cold Spring Harbor Laboratory Press, Cold Spring Harbor, N.Y., 2001.
Spanjer and Scherphof, Biochim Biophys Acta.; 734(1):40-7, 1983
Shayakhmetov et al., J. Virol. 79, 7478-749 1, (2005).
Sipkins et al., Nature Med. 4, 623-626, (1998).
Souza et al., PNAS 103, 1215-1220, 2006, (2006).
Tai and Laforest, Annu Rev. Biomed. Eng. 7, 255-285, (2005).
Tandle et al., Cytokine 30:347-58, (2005)
Temin, *In: Gene Transfer,* Kucherlapati (ed.), NY, Plenum Press, 149-188, 1986.
Tjuvajev et al., Cancer Res. 58, 4333-4341, (1998).
Tjuvajev et al., Cancer Res. 59, 5 186-5193, (1999).
Tratschin et al., Mol. Cell. Biol. 5(11):3251-3260, (1985).
Trepel et al., Cancer Res. 61, 8 1 10-81 12, (2001).
Uhrbom et al., Nature Med. 10, 1257-1 260, (2004).
Wagner et al., PNAS 89:7934-7938, (1992).
Walensky et al., Science 305, 14 1 1-14.13, (2004).
White et al., Circulation 109, 5 13-5 19, (2004).
Wilson et al., *Mol. Cell. Biol.,* 10(12):6181-6191, 1990.
Xiao et al., J. Virol. 72, 2224-2232, (1998).
Yang et al., J. Virol. 7 1, 923 1-9247, (1997).
Zacher et al., Gene 9, 127-140, (1980).
Zechner et al., *Mol. Cell. Biol.,* 8(6):2394-2401, 1988.

What is claimed is:

1. A method of detecting gene transfer in a subject, wherein the subject has, is suspected of having, or at risk of developing a hyperproliferative disease, the method comprising:
(a) administering a therapeutic adeno-associated viral/phage vector (AAVP) encoding a reporter to a subject having, suspected of having or at risk of developing a pathologic or disease condition; and
(b) evaluating in situ expression of the therapeutic AAVP in a tissue or cell targeted for treatment by detecting the encoded reporter or reporter activity.

2. The method of claim 1, wherein evaluation of AAVP expression is by non-invasive detection of the reporter or an activity of the reporter.

3. The method of claim 1, wherein the reporter is an enzyme.

4. The method of claim 3, wherein the enzyme is a kinase.

5. The method of claim 4, wherein the kinase is thymidine kinase.

6. The method of claim 5, wherein the kinase modifies a compound labeled with a detectable label.

7. The method of claim 6, wherein the detectable label is detectable by fluorescence, chemiluminescence, surface enhanced raman spectroscopy (SERS), magnetic resonance imaging (MRI), computer tomography (CT), or positron emission tomography (PET) imaging.

8. The method of claim 6, wherein the detectably labeled compound is a nucleoside analog.

9. The method of claim 8, wherein the detectably labeled compound is fluorodeoxyglucose (FDG); 2'-fluoro-2'deoxy-1beta-D-arabinofuranosyl-5-ethyl-uracil (FEAU); 5-[$^{123}$I]-2'-fluoro-5-iodo-1β-D-arabinofuranosyl-uracil; 5-[$^{124}$I]-2'-fluoro-5-iodo-1β-D-arabinofuranosyl-uracil; 5-[$^{131}$I]-2'-fluoro-5-iodo-1β-D-arabinofuranosyl-uracil; 5-[$^{18}$F]-2'-fluoro-5-fluoro-1-β-D-arabinofuranosyl-uracil; 2-[$^{11}$I]- and 5-[$^{11}$C]-methyl)-2'-fluoro-5-methyl-1-β-D-arabinofuranosyl-uracil; 2-[$^{11}$C]-2'-fluoro-5-ethyl-1-β-D-arabinofuranosyl-uracil; 5-([$^{11}$C]-ethyl)-2'-fluoro-5-ethyl-1-β-D-arabinofuranosyl-uracil; 5-(2-[$^{18}$F]-ethyl)-2'-fluoro-5-(2-fluoroethyl)-1-β-D-arabinofuranosyl-uracil, 5-[$^{123}$I]-2'-fluoro-5-iodovinyl-1-β-D-arabinofuranosyl-uracil; 5-[$^{124}$I]-2'-fluoro-5-iodovinyl-1-β-D-arabinofuranosyl-uracil; 5-[$^{131}$I]-2'-fluoro-5-iodovinyl-1-β-D-arabinofuranosyl-uracil; 5-[$^{123}$I]-2'-fluoro-5-iodo-1-β-D-ribofuranosyl-uracil; 5-[$^{124}$I]-2'-fluoro-5-iodo-1-β-D-ribofuranosyl-uracil; 5-[$^{131}$I]-2'-fluoro-5-iodo-1-β-D-ribofuranosyl-uracil; 5-[$^{123}$I]-2'-fluoro-5-iodovinyl-1-β-D-ribofuranosyl-uracil; 5-[$^{124}$I]-2'-fluoro-5-iodovinyl-1-β-D-ribofuranosyl-uracil; 5-[$^{131}$I]-2'-fluoro-5-iodovinyl-1-β-D-ribofuranosyl-uracil; or 9-4-[$^{18}$F]fluoro-3-(hydroxymethyl)butyl]guanine.

10. The method of claim 6, wherein the detectably labeled compound comprises a $^{18}$F, $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{109}$Cd, $^{47}$Ca, $^{11}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{153}$Gd, $^{66}$Ga, $^{67}$Ga, $^{68}$Ga, $^{72}$Ga, $^{198}$Au, $^{3}$H, $^{166}$Ho, $^{111}$In, $^{113}$In, $^{115}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{15}$O, $^{191}$Os, $^{109}$Pd, $^{32}$P, $^{33}$P, $^{42}$K, $^{226}$Ra, $^{186}$Re, $^{188}$Re, $^{82}$Rb, $^{153}$Sm, $^{46}$Sc, $^{47}$Sc, $^{72}$Se, $^{75}$Se, $^{105}$Ag, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn, or $^{65}$Zn.

11. The method of claim 6, wherein the detectable label is $^{131}$I, $^{125}$I, $^{123}$I, $^{111}$I, $^{99m}$Tc, $^{90}$Y, $^{186}$Re, $^{188}$Re, $^{32}$P, $^{153}$Sm, $^{67}$Ga, $^{201}$Tl, $^{77}$Br, or $^{18}$F label.

12. The method of claim 1, wherein the AAVP comprises a moiety that selectively targets a tissue or cell targeted for treatment.

13. The method of claim 12, wherein the moiety is encoded by a capsid protein of the AAVP.

14. The method of claim 13, wherein the capsid protein is recombinant capsid protein.

15. The method of claim 14, wherein the recombinant capsid protein comprises a targeting peptide.

16. The method of claim 15, wherein the targeting peptide is a cyclic peptide.

17. The method of claim 15, wherein the targeting peptide is a linear peptide.

18. The method of claim 15, wherein the targeting peptide selectively binds a cell expressing an integrin on the cell surface.

19. The method of claim 18, wherein the integrin is αvβ3 or αvβ5 integrin.

20. The method of claim 15, wherein the targeting peptide comprises an RGD motif.

21. The method of claim 15, wherein the targeting peptide selectively binds a cell expressing a transferrin receptor.

22. The method of claim 21, wherein the peptide comprises an amino acid sequence comprising CRTIGPSVC.

23. The method of claim 1, wherein the hyperproliferative disease is fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

24. The method of claim 1, wherein the reporter gene is operatively coupled a tissue or cell specific promoter.

25. The method of claim 1, wherein evaluating expression comprises administering a label that is selectively metabolized by a cell expressing the AAVP nucleic acid.

26. The method of claim 1, wherein the therapeutic AAVP encodes a second therapeutic gene.

27. The method of claim 26, wherein the second therapeutic gene is tumor suppressor, inhibitory RNA, inhibitory DNA, or prodrug converting enzyme.

\* \* \* \* \*